US011447477B2

(12) United States Patent
Du et al.

(10) Patent No.: US 11,447,477 B2
(45) Date of Patent: Sep. 20, 2022

(54) INDOLEAMINE-2,3-DIOXYGENASE INHIBITOR, THE PREPARATIVE METHOD AND THE USE THEREOF

(71) Applicant: HINOVA PHARMACEUTICALS INC., Sichuan (CN)

(72) Inventors: Wu Du, Sichuan (CN); Chaowu Ai, Sichuan (CN); Yu Li, Sichuan (CN); Kun Wen, Sichuan (CN); Haibin Lv, Sichuan (CN); Wen Ren, Sichuan (CN); Jinyun He, Sichuan (CN); Dekun Qin, Sichuan (CN); Xinghai Li, Sichuan (CN); Yuanwei Chen, Sichuan (CN)

(73) Assignee: HINOVA PHARMACEUTICALS INC., Sichuan (CN)

( * ) Notice: Subject to any disclaimer, the term of this patent is extended or adjusted under 35 U.S.C. 154(b) by 0 days.

(21) Appl. No.: 16/956,581

(22) PCT Filed: Dec. 20, 2018

(86) PCT No.: PCT/CN2018/122247
§ 371 (c)(1),
(2) Date: Jun. 20, 2020

(87) PCT Pub. No.: WO2019/120237
PCT Pub. Date: Jun. 27, 2019

(65) Prior Publication Data
US 2021/0198247 A1 Jul. 1, 2021

(30) Foreign Application Priority Data
Dec. 20, 2017 (CN) .......................... 201711385641.3

(51) Int. Cl.
| A61P 35/00 | (2006.01) |
| A61P 25/00 | (2006.01) |
| A61P 25/22 | (2006.01) |
| A61P 25/24 | (2006.01) |
| A61P 25/28 | (2006.01) |
| A61P 27/12 | (2006.01) |
| A61P 31/18 | (2006.01) |
| A61P 37/02 | (2006.01) |
| C07D 413/12 | (2006.01) |
| C07D 413/14 | (2006.01) |
| A61P 3/00 | (2006.01) |

(52) U.S. Cl.
CPC ............ C07D 413/12 (2013.01); A61P 35/00 (2018.01); C07B 2200/05 (2013.01)

(58) Field of Classification Search
CPC ..... C07D 413/12; C07D 413/14; A61P 35/00; A61P 3/00; A61P 25/00; A61P 25/22; A61P 25/24; A61P 25/28; A61P 27/12; A61P 31/18; A61P 37/02; C07B 2200/05; A61K 31/4245; A61K 31/454; A61K 31/5377

See application file for complete search history.

(56) References Cited

U.S. PATENT DOCUMENTS

2019/0169140 A1* 6/2019 Zhang ................. C07D 271/08
2020/0181131 A1* 6/2020 Wu ........................ A61P 37/06

FOREIGN PATENT DOCUMENTS

| CN | 101212967 A | 7/2008 | |
| CN | 102164902 A | 8/2011 | |
| CN | 105646389 A | 6/2016 | |
| CN | 106565696 A | 4/2017 | |
| CN | 106883194 A * | 6/2017 | |
| CN | 106967005 A | 7/2017 | |
| CN | 107033097 A | 8/2017 | |
| CN | 107176933 A | 9/2017 | |
| CN | 107304191 A | 10/2017 | |
| WO | WO-2006122150 A1 * | 11/2006 | ......... A61K 31/4245 |
| WO | 2010005958 A2 | 1/2010 | |
| WO | 2013174947 A1 | 11/2013 | |
| WO | 2014066834 A1 | 5/2014 | |
| WO | 2016155545 A1 | 10/2016 | |
| WO | 2017106062 A1 | 6/2017 | |
| WO | 2018024208 A1 | 2/2018 | |
| WO | WO-2018196747 A1 * | 11/2018 | ......... A61K 31/4245 |

* cited by examiner

Primary Examiner — John M Mauro
(74) Attorney, Agent, or Firm — Novick, Kim & Lee, PLLC; Allen Xue

(57) ABSTRACT

Provided is a compound represented by formula (I). Also provided are a pharmaceutical composition containing the compound of formula (I) and use of the compound in preparing indoleamine-2,3-dioxygenase (IDO) inhibitor drugs. The compound or the pharmaceutical composition thereof can be used for preparing drugs for preventing and/or treating diseases having pathological features of IDO-mediated tryptophan metabolic pathways.

1 Claim, No Drawings

INDOLEAMINE-2,3-DIOXYGENASE INHIBITOR, THE PREPARATIVE METHOD AND THE USE THEREOF

TECHNICAL FIELD

The present invention belongs to the field of pharmaceutical chemistry, and relates to an indoleamine-2,3-dioxygenase inhibitor, the preparative method and the use thereof.

BACKGROUND ART

Malignant tumor is one of the major diseases threatening human health and life. According to the statistics of the National Health Commission, the incidence of tumor in China's mainland is about 235/100000, and the mortality rate is about 144.3/100000.

Due to the unlimited growth, invasion and metastasis of malignant tumors, three conventional treatment methods (surgery, radiotherapy, and chemotherapy) currently used in clinical can not allow to completely remove or kill tumor cells, so tumor metastasis or recurrence often occurs. Tumor biotherapy is a new therapeutic method that uses modern biotechnology and its related products for prevention and treatment of tumors. Because of its characteristics such as safety, effectiveness, low side effects, and so on, biotherapy has become the fourth mode of tumor treatment except for surgery, radiotherapy, and chemotherapy. It can achieve the anti-tumor effect by inspiring the natural defense mechanism of the host or giving the naturally produced substances with strong targeting.

Indoleamine-2,3-dioxygenase (IDO) is a kind of heme-containing monomer protein, and consisted of 403 amino acid residues, including two folded α-helix domains. The large domain contains catalytic pocket, and the substrate can have hydrophobic and other interactions with IDO in the catalytic pocket. Except for liver, IDO is the only rate-limiting enzyme which can catalyze tryptophan metabolism and make it decompose to a series of metabolites including quinolinic acid by the kynurenine pathway. Another kind of enzymes catalyzing tryptophan metabolism are tryptophan-2,3-dioxygenase, which have similar heme activity sites with IDO, but only about 10% of the amino acid sequences of both enzymes are same. About 95% of free L-tryptophan in human body can be metabolized by the kynurenine pathway, and many kinds of biologically active metabolites are produced, including kynurenine, kynuric acid, 3-hydroxykynurenine, 3-hydroxy-2-aminobenzoic acid, picolinic acid, quinolinic acid, and oxidized coenzyme A, etc. The expression level of IDO was low in normal state, and increased significantly in the process of inflammation or infection. In addition, lipopolysaccharide and cytokines and so on could induce the expression of IDO. In vivo study indicates that except for kynurenine, the intermediate metabolites of tryptophan, 3-hydroxy-2-aminobenzoic acid and quinolinic acid, can also induce apoptosis of T-lymphocyte in in vitro mouse thymocytes. Tumor cells can induce local immunity by consuming local tryptophan and producing metabolites. Meanwhile, the level of local infiltrative T-lymphocytes in tumor decreases significantly. In short, IDO can inhibit the local immunity of tumor via the following ways: (1) Tryptophan depletion mechanism: it is clear that by making IDO overexpress and resulting in the lack of tryptophan necessary for T cell proliferation, the effective proliferation of T cells is affected and leads to the apoptosis of cells; (2) Toxic mechanism of tryptophan metabolites: the metabolites produced by the degradation of tryptophan catalyzed by IDO can inhibit the function of activated T cells and even induce apoptosis of T cells; (3) IDO can inhibit the immune function of activated T cells by inducing the proliferation of regulatory T cells. Therefore, IDO is a potential target for tumor immunotherapy.

The disclosed patent applications of inhibitors for selective inhibition of IDO include WO2010005958, WO2013174947, WO2014066834, WO2016155545, CN201610059454.5, CN2017100610.4, etc. 1-Methyltryptophan is an oral small molecular IDO inhibitor developed by Newlink Genetics, which is used to treat metastatic breast cancers and solid tumors. It is currently in the phase II clinical trial that has continued for a long time. In addition, for a series of oral IDO small molecular inhibitors being developed by Incyte company, INCB-24360 is also undergoing phase III clinical trials, which are mainly used to treat a variety of cancers including myelodysplastic syndrome. However, there is a certain of toxic and stable problems for drug metabolism in clinical trials.

Therefore, in order to realize better effect and purpose of tumor treatment and better meet the market demand, it is urgently needed to develop a new generation of high-efficient and low toxic selective IDO inhibitors.

CONTENT OF THE INVENTION

In order to solve the above technical problems, the present invention provides compounds of formula (I), or optical isomers thereof, or cis- and trans-isomers thereof, or solvates thereof, or pharmaceutically acceptable salts thereof, or pro-drugs thereof, or tautomers thereof, or mesomers thereof, or racemates thereof, or enantiomers thereof, or diastereoisomers thereof, or mixtures thereof, or metabolites thereof, or metabolic precursors thereof:

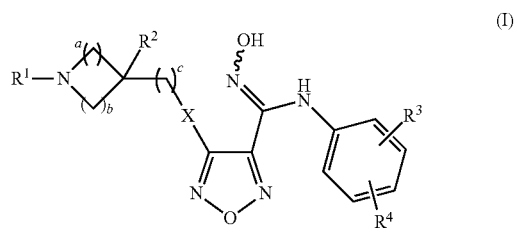

Wherein, X is amino group, oxygen, and sulfur;
$R^1$ is hydrogen, $-(CH_2)_mCOR^5$, $-(CH_2)_mSO_2R^6$, $-(CH_2)_mCOOR^7$, alkyl, haloalkyl, alkoxy, cycloalkyl, substituted cycloalkyl, heterocycloalkyl, substituted heterocycloalkyl, unsaturated heterocyclic group, substituted unsaturated heterocycloalkyl, aryl, substituted aryl, aromatic heterocyclic group, and substituted heteroaryl; m is selected from integers of 0-5;
$R^5$, $R^6$ and $R^7$ are independently of each other selected from alkyl, amino, hydroxy, cycloalkyl, alkoxy, heterocycloalkyl, $-CONR^8R^9$, $-NR^8R^9$, aryl, and aromatic heterocyclic group; $R^8$ and $R^9$ are independently of each other selected from hydrogen, amino, hydroxy, alkyl, alkoxy, cycloalkyl, heterocycloalkyl, aryl, substituted aryl, heteroaryl, substituted heteroaryl, or $R^1$ and $R^9$ are linked together to form a ring;
$R^2$ is hydrogen, alkyl, hydroxyl, amino, alkoxy, alkylamino, and halogen;
$R^3$ and $R^4$ are respectively selected from hydrogen, halogen, cyano, alkyl, cycloalkyl, heterocycloalkyl, alkoxy, amino, carboxyl, aryl, substituted aryl, heteroaryl, and substituted heteroaryl;

Wherein, hydrogen means hydrogen element (H) or isotope deuterium (D);

a is an integer of 0 to 5; b is an integer of 0 to 5; c is an integer of 1 to 5; a and b are not both 0.

Further, said compound has a structure of formula (II):

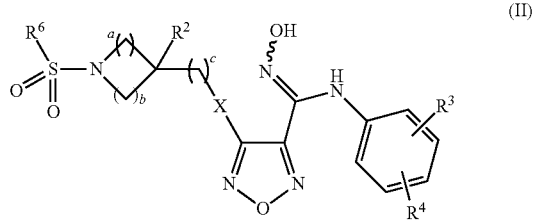

(II)

Wherein, $R^6$ is selected from the group consisting of alkyl, amino, hydroxy, cycloalkyl, alkoxy, heterocycloalkyl, —$CONR^8R^9$, —$NR^8R^9$, aryl, and aromatic heterocyclic group;

$R^1$ and $R^9$ are independently of each other selected from hydrogen, amino, hydroxy, alkyl, alkoxy, cycloalkyl, heterocycloalkyl, aryl, substituted aryl, heteroaryl, substituted heteroaryl, or $R^1$ and $R^9$ are linked together to form a ring;

Further, said compound has a structure of formula (III):

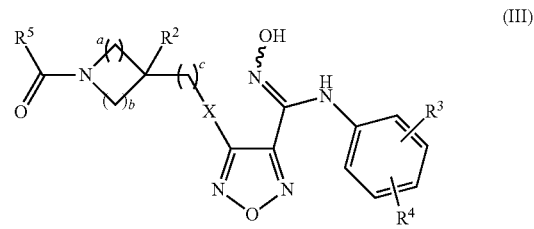

(III)

Wherein, $R^5$ is selected from the group consisting of alkyl, amino, hydroxy, cycloalkyl, alkoxy, heterocycloalkyl, —$CONR^8R^9$, —$NR^8R^9$, aryl, and aromatic heterocyclic group;

$R^8$ and $R^9$ are independently of each other selected from hydrogen, amino, hydroxy, alkyl, alkoxy, cycloalkyl, heterocycloalkyl, aryl, substituted aryl, heteroaryl, substituted heteroaryl, or $R^8$ and $R^9$ are linked together to form a ring.

Further, when a is 0, said compounds have a structure of formula (IV); when b is 0, said compounds have a structure of formula (V):

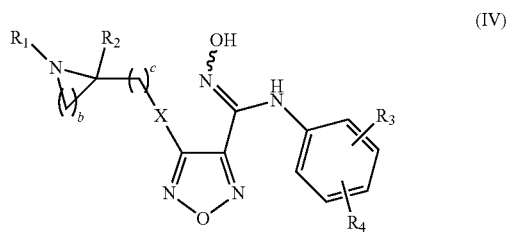

(IV)

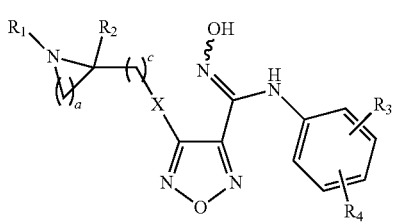

(V)

$R^1$ is hydrogen, $COR^5$, $SO_2R^6$, C1-C8 alkyl, C1-C8 haloalkyl, C1-C8 alkoxy, C3-C8 cycloalkyl, C3-C8 heterocycloalkyl, C3-C8 unsaturated heterocyclic group, aryl, substituted aryl, aromatic heterocyclic group, and substituted heteroaryl;

$R^5$ and $R^6$ are dependently of each other selected from the group consisting of alkyl, hydroxy, C3-C8 cycloalkyl, alkoxy, C3-C8 heterocycloalkyl, —$CONR^8R^9$, —$NR^8R^9$, aryl, and heteroaryl;

$R^8$ and $R^9$ are independently of each other selected from hydrogen, amino, hydroxy, C1-C8 alkyl, C1-C8 alkoxy, C3-C8 cycloalkyl, C3-C8 heterocycloalkyl, aryl, substituted aryl, heteroaryl, and substituted heteroaryl;

$R^2$ is hydrogen, C1-C8 alkyl, hydroxyl, amino, C1-C8 alkoxy, C1-C8 alkylamino, and halogen;

$R^3$ and $R^4$ are respectively selected from hydrogen, halogen, C1-C8 alkyl, C3-C8 cycloalkyl, C3-C8 heterocycloalkyl, C1-C8 alkoxy, amino, carboxyl, aryl, substituted aryl, heteroaryl, and substituted heteroaryl.

Further, when a is 1 and b is 1, said compounds have a structure of formula (VI):

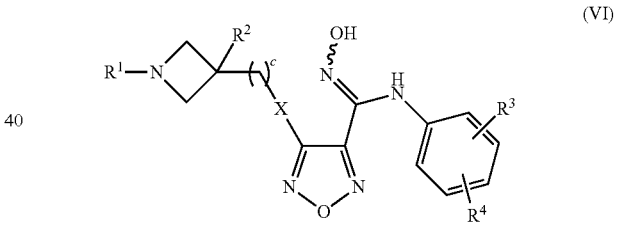

(VI)

$R^1$ is hydrogen, $COR^5$, $SO_2R^6$, C1-C8 alkyl, C1-C8 haloalkyl, C1-C8 alkoxy, C3-C8 cycloalkyl, C3-C8 heterocycloalkyl, C3-C8 unsaturated heterocyclic group, aryl, substituted aryl, aromatic heterocyclic group, and substituted heteroaryl;

$R^5$ and $R^6$ are dependently of each other selected from the group consisting of alkyl, hydroxy, C3-C8 cycloalkyl, alkoxy, C3-C8 heterocycloalkyl, —$CONR^8R^9$, —$NR^8R^9$, aryl, and heteroaryl;

$R^8$ and $R^9$ are independently of each other selected from hydrogen, amino, hydroxy, C1-C8 alkyl, C1-C8 alkoxy, C3-C8 cycloalkyl, C3-C8 heterocycloalkyl, aryl, substituted aryl, heteroaryl, substituted heteroaryl, or $R^8$ and $R^9$ are linked together to form a ring;

$R^2$ is hydrogen, C1-C8 alkyl, hydroxyl, amino, C1-C8 alkoxy, C1-C8 alkylamino, and halogen;

$R^3$ and $R^4$ are respectively selected from hydrogen, halogen, C1-C8 alkyl, C3-C8 cycloalkyl, C3-C8 heterocycloalkyl, C1-C8 alkoxy, amino, carboxyl, aryl, substituted aryl, heteroaryl, and substituted heteroaryl.

Further, said compounds include following compounds, but not limited to these compounds:

2
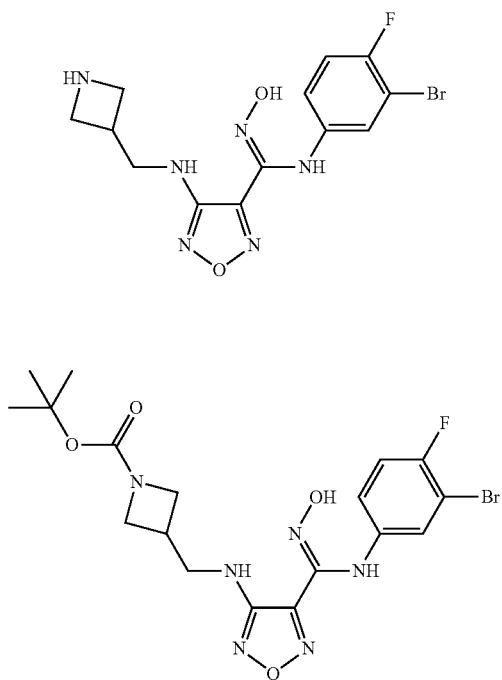
3
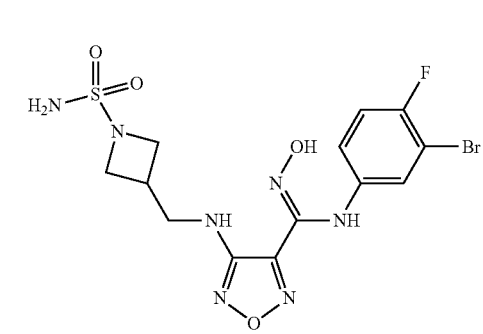
4
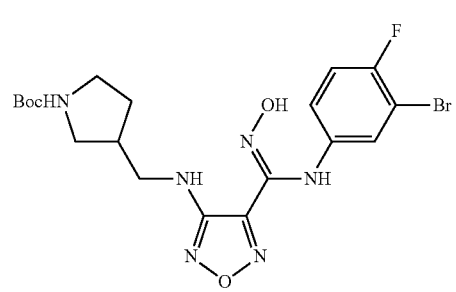
5
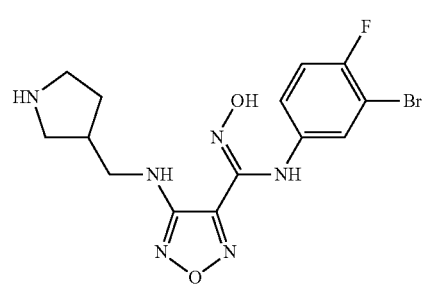
6
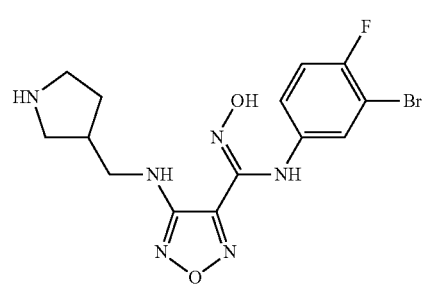
7
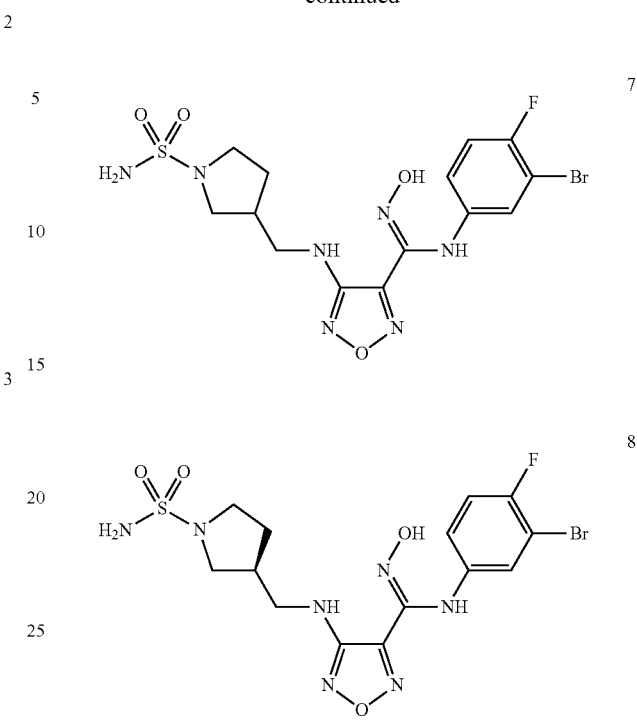
8
9
10
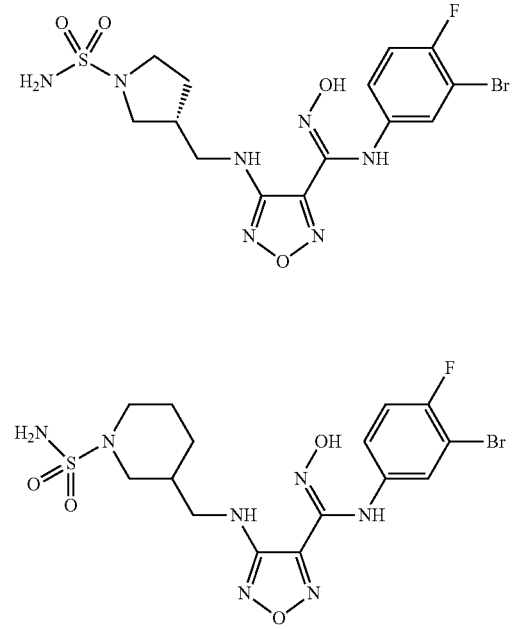
11
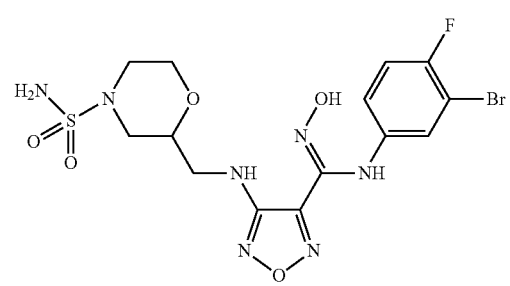

12
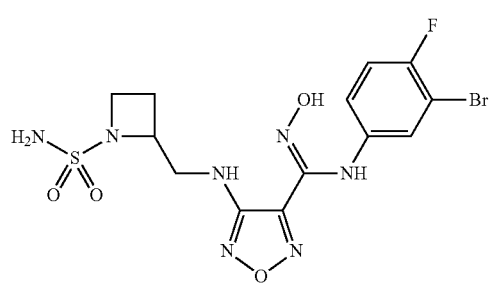
13
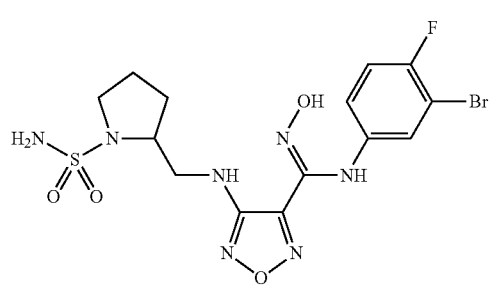
14
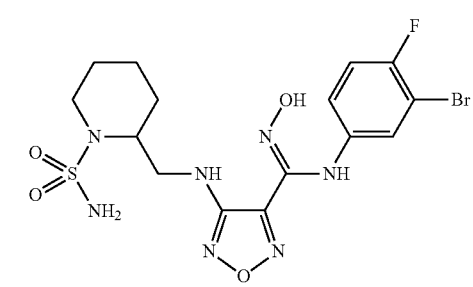
15
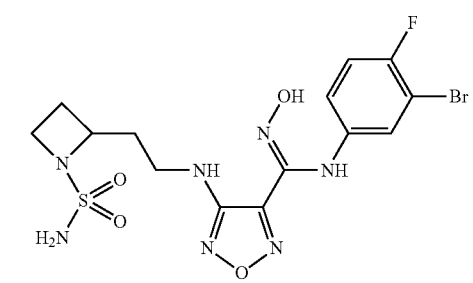
16
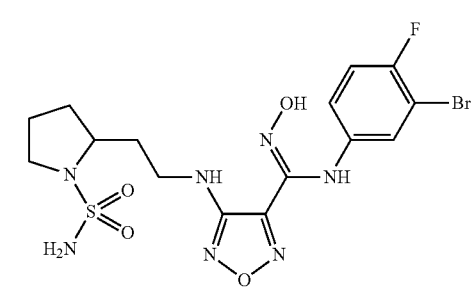
17
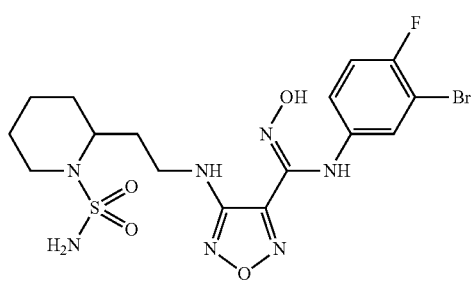
18
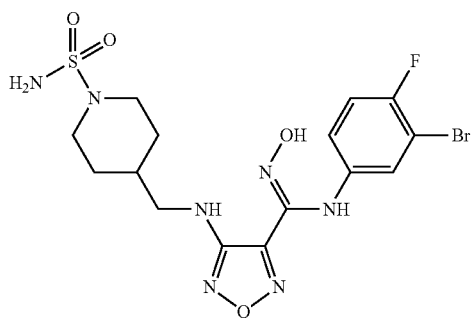
19
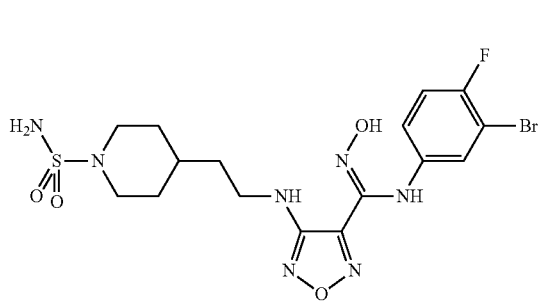
20
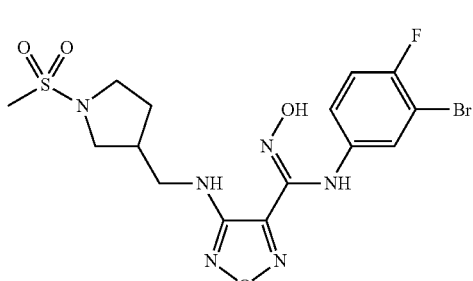
21
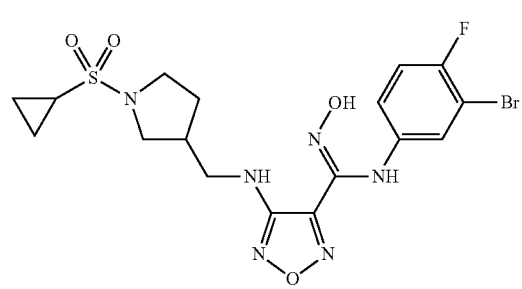

9
-continued
22
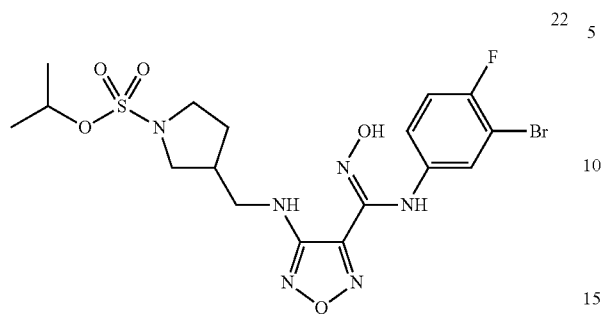
23
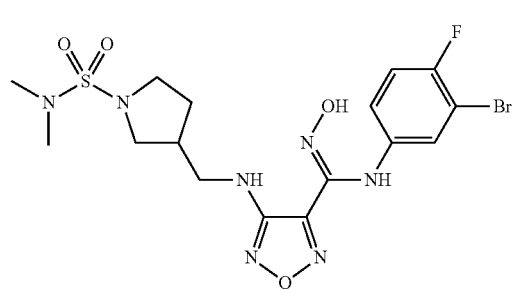
24
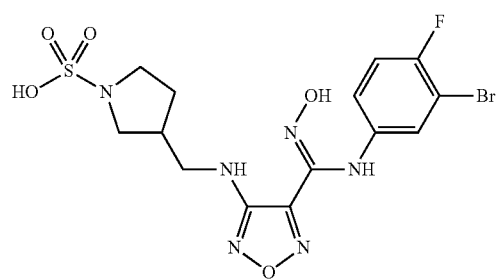
25
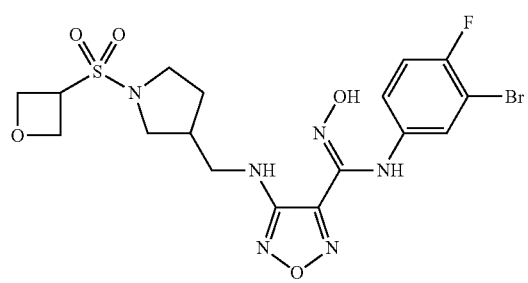
26
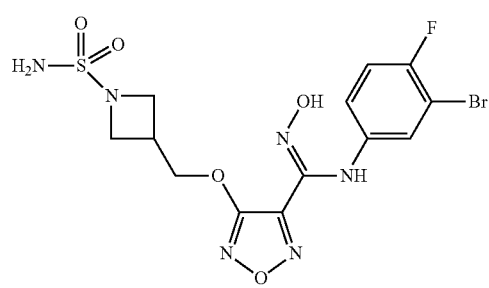
10
-continued
27
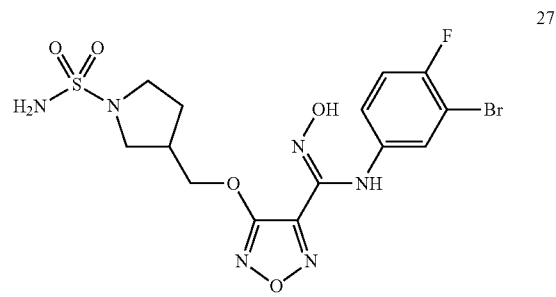
28
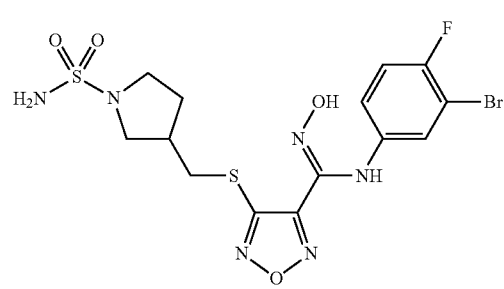
29
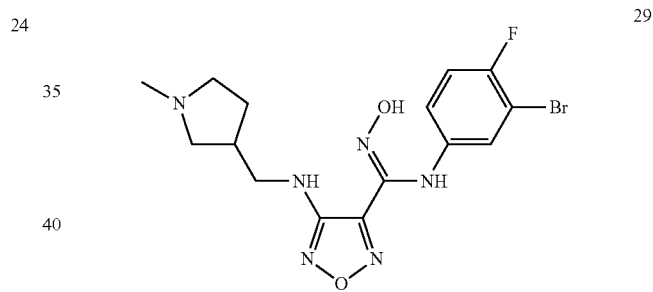
30
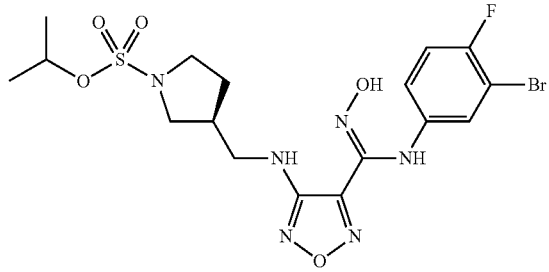
31
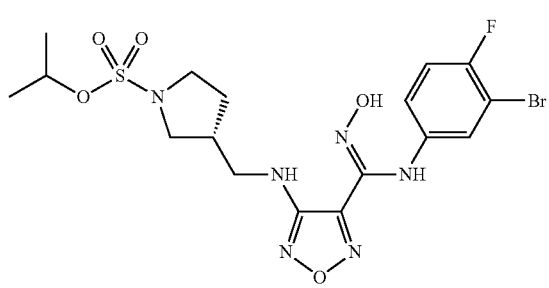

32
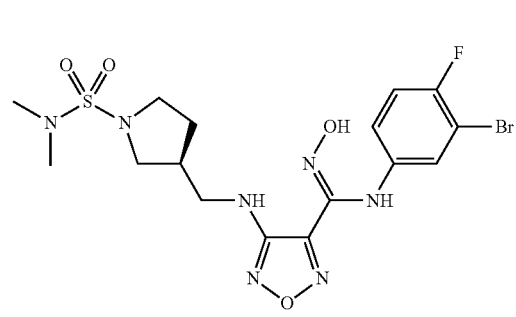
33
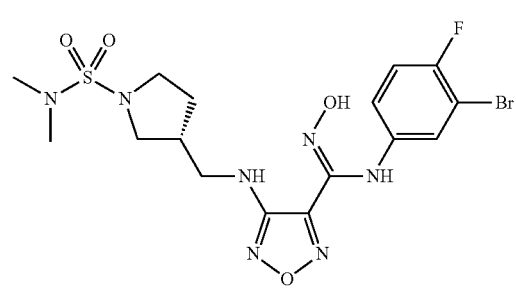
34
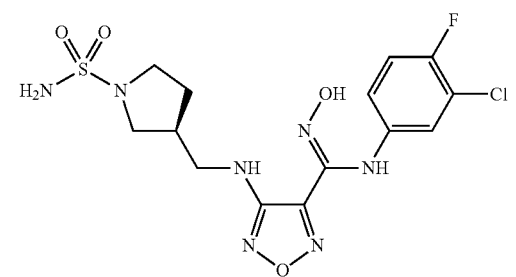
35
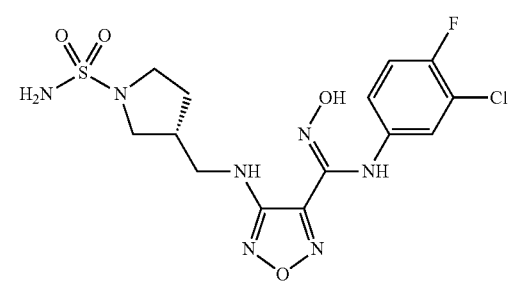
36
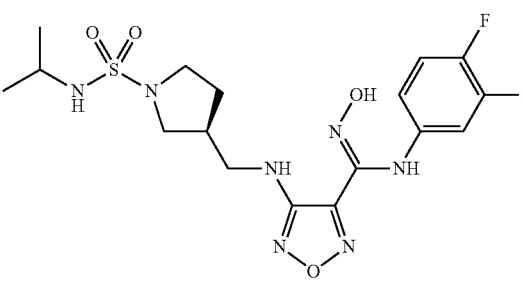
37
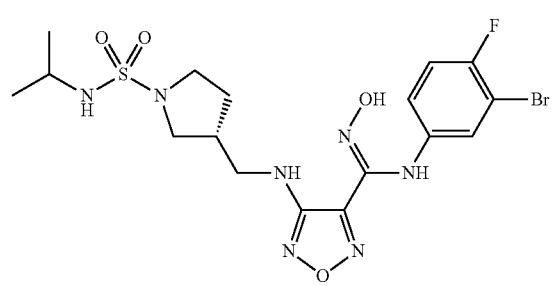
38
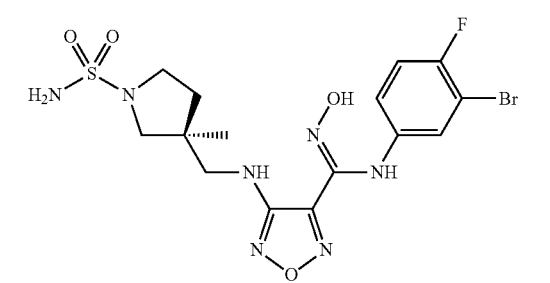
39
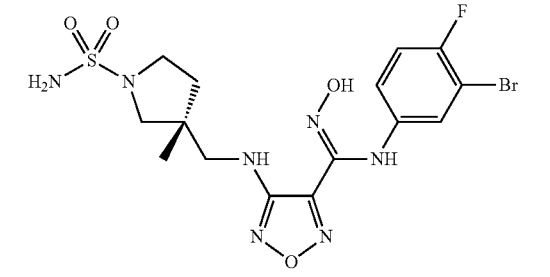
40
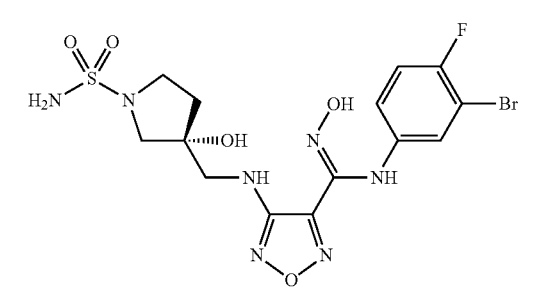
41
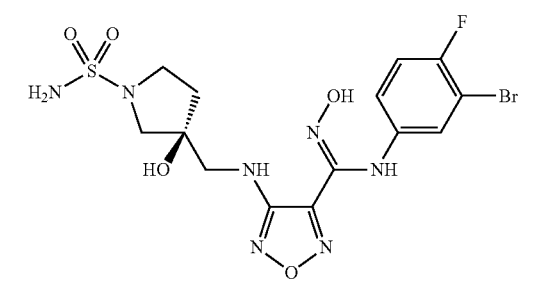

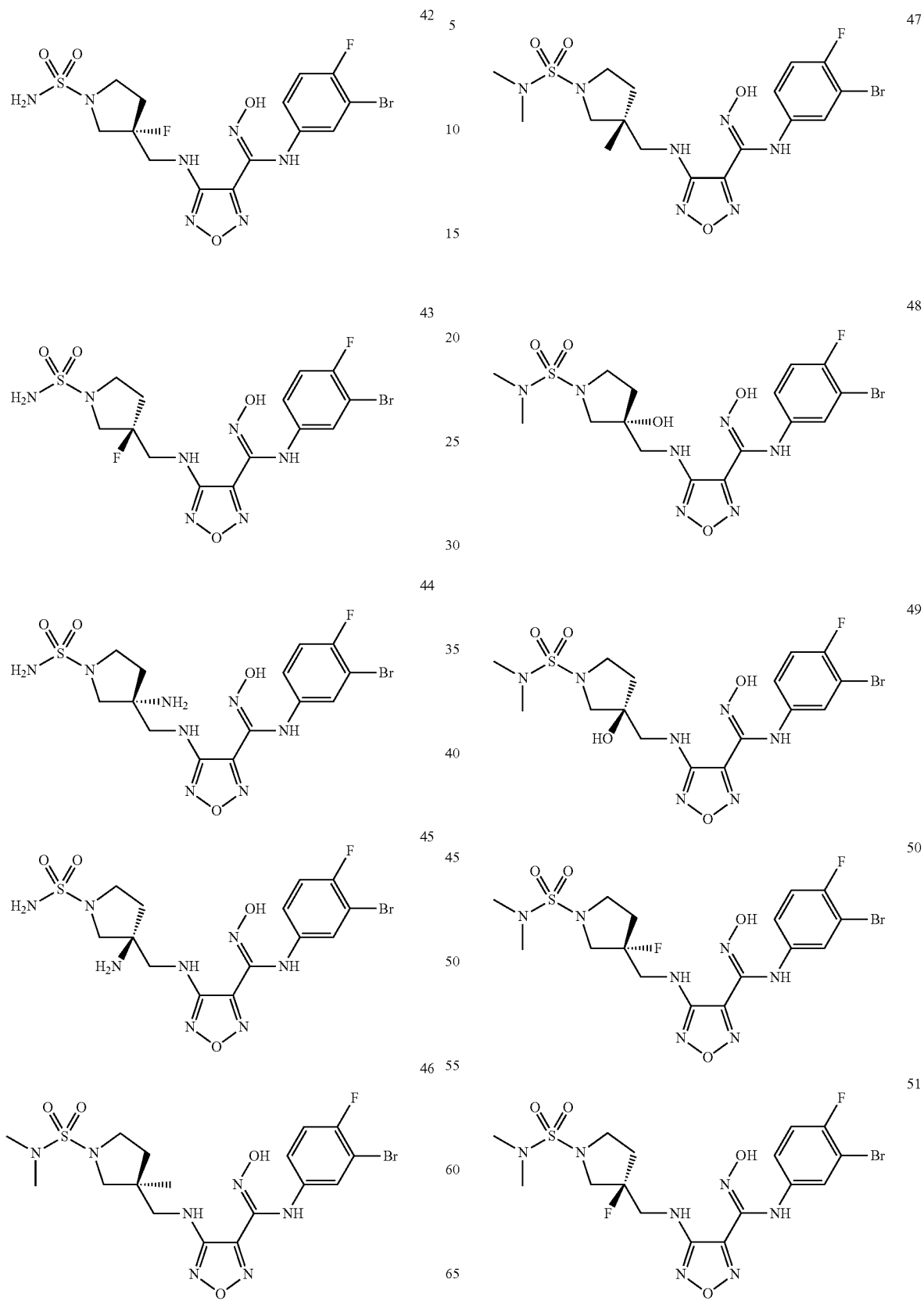

52
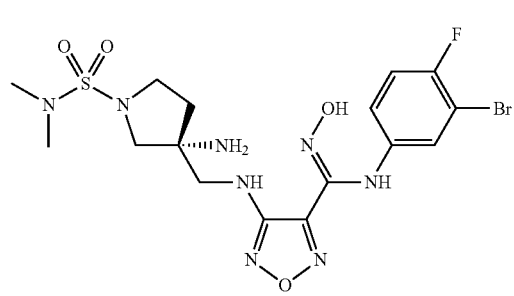
53
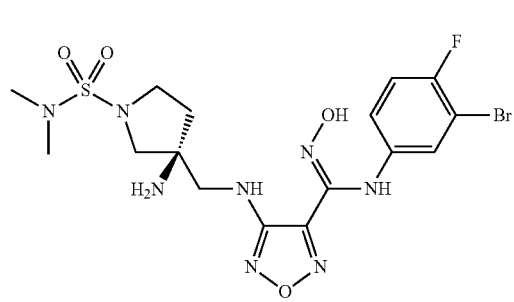
54
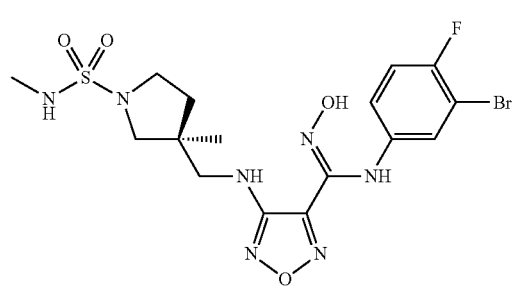
55
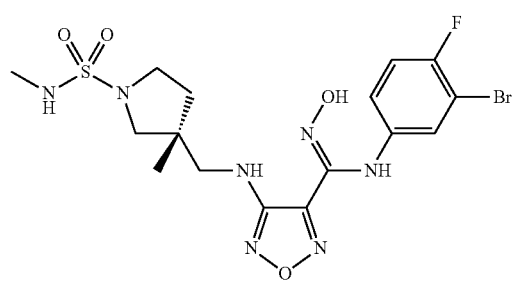
56
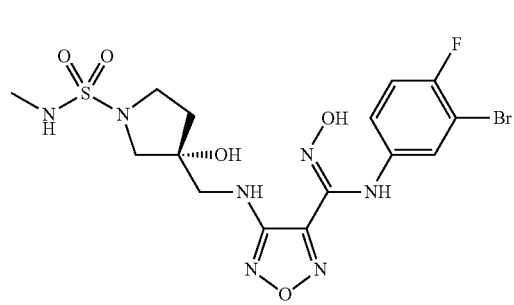
57
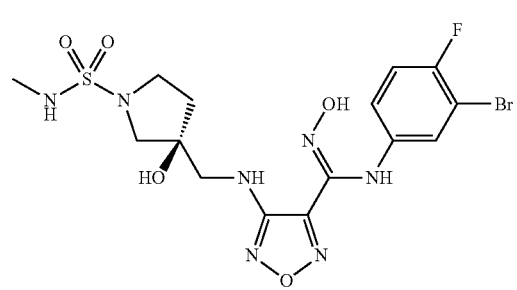
58
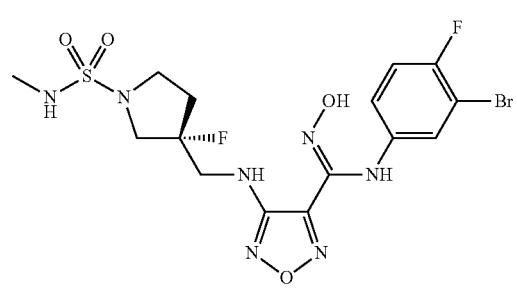
59
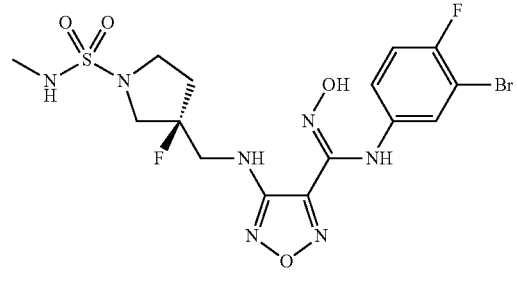
60
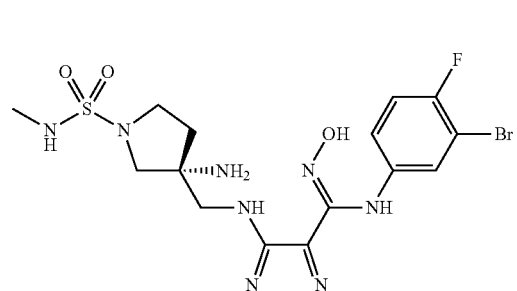
61
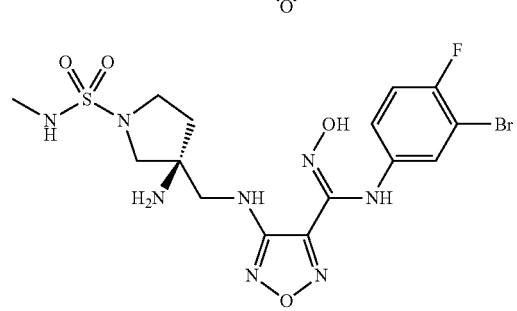

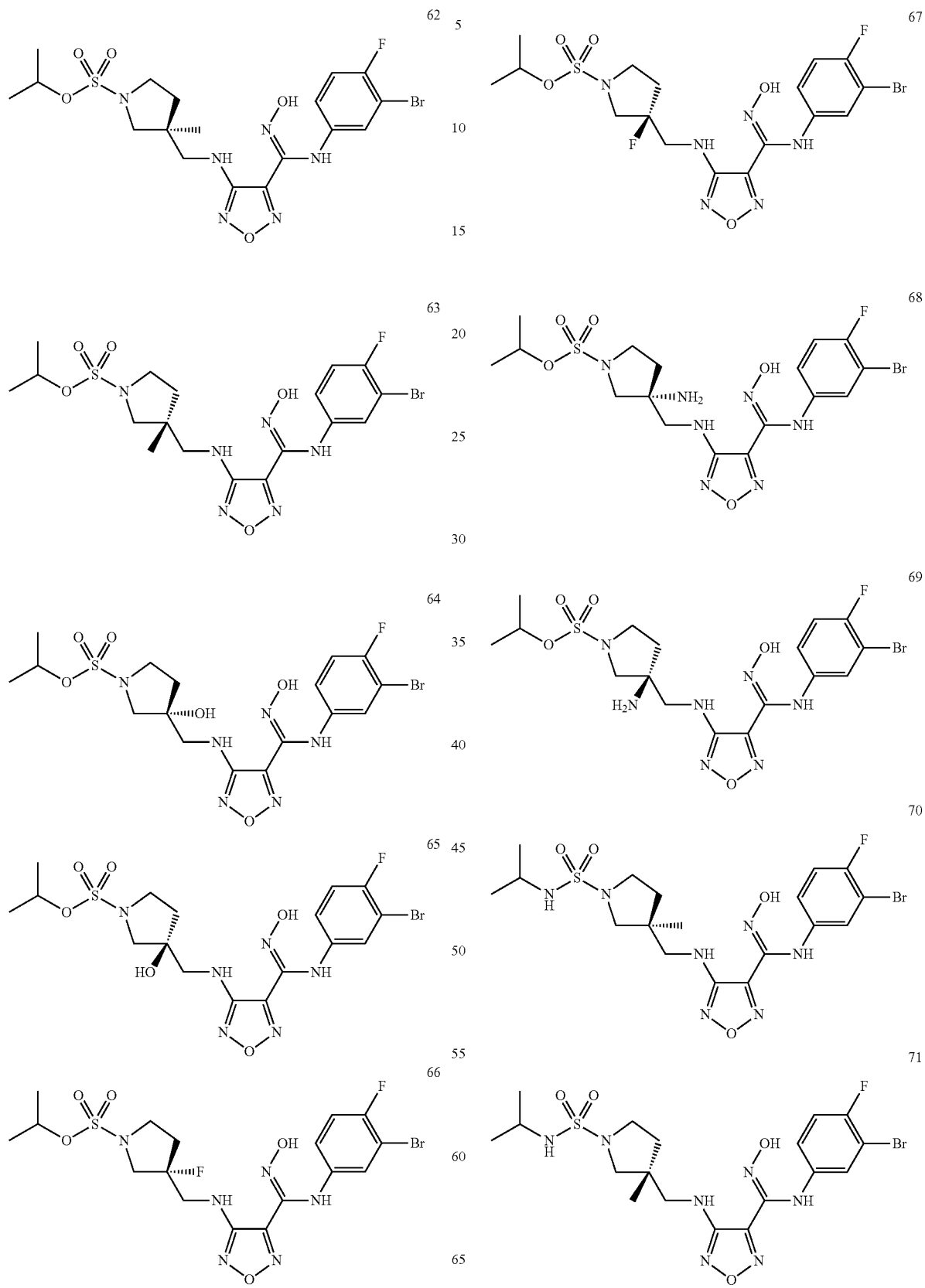

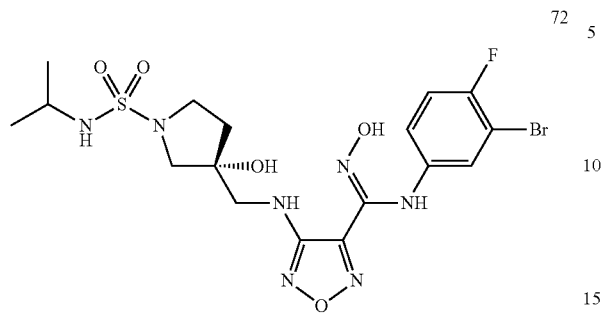
72
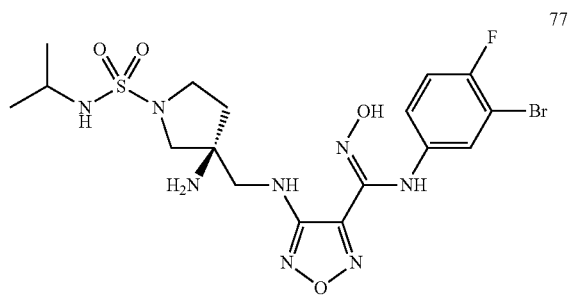
77
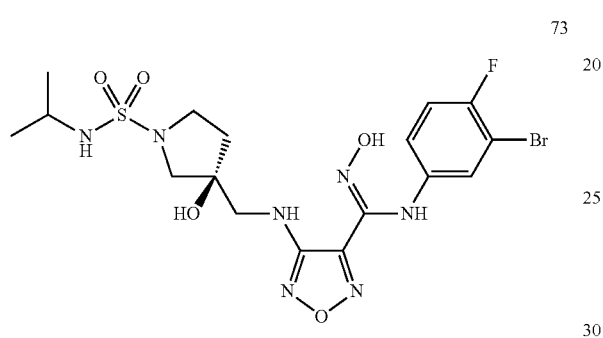
73
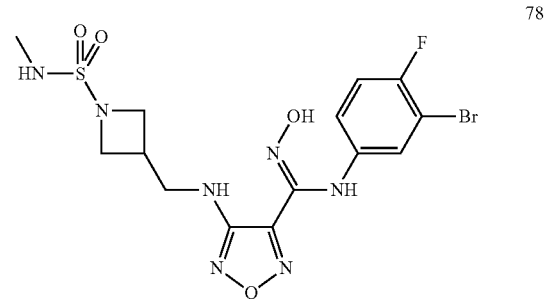
78
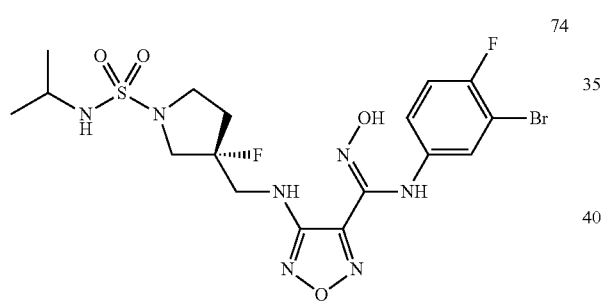
74
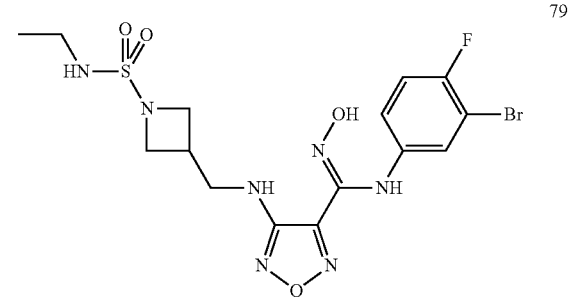
79
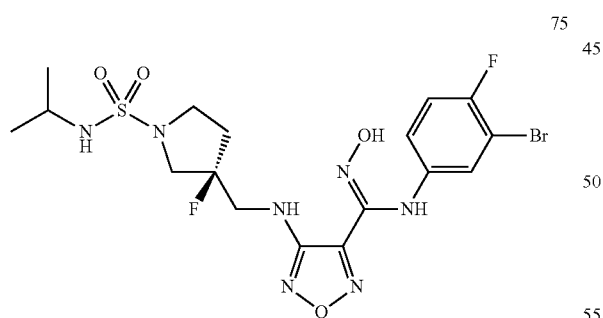
75
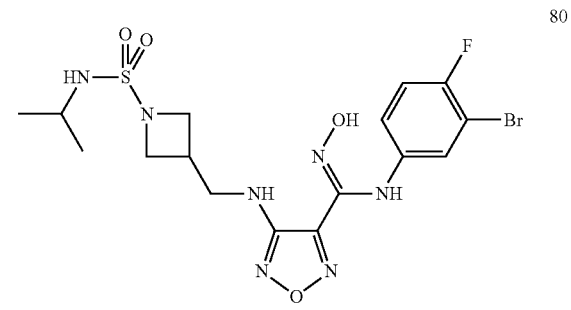
80
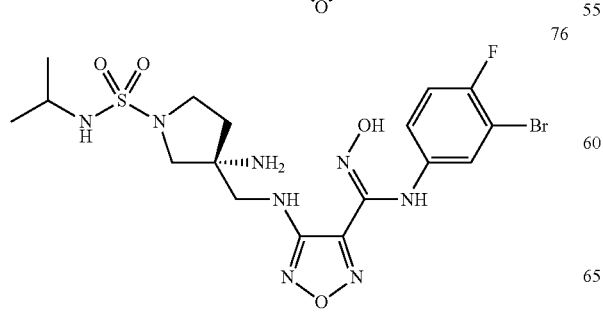
76
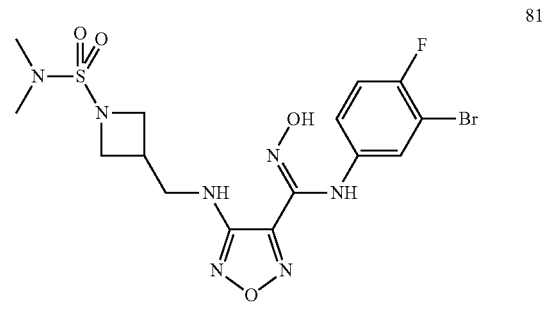
81

| 82 | 87 |
|---|---|
| 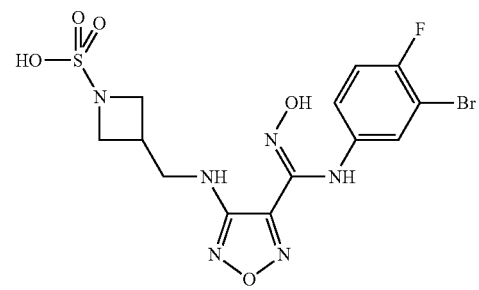 | 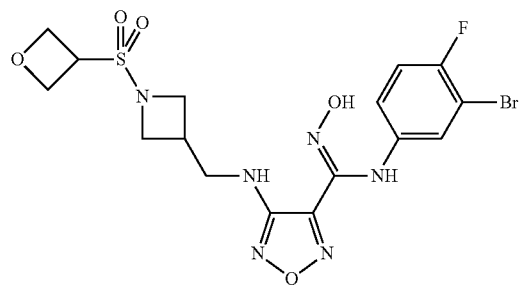 |
| 83 | 88 |
| 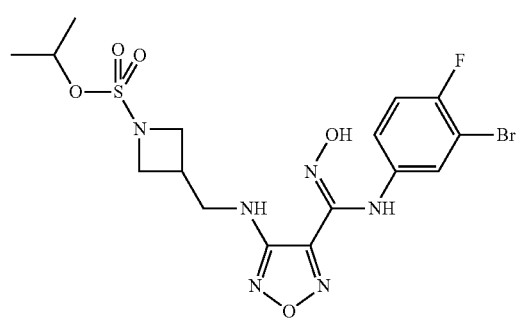 | 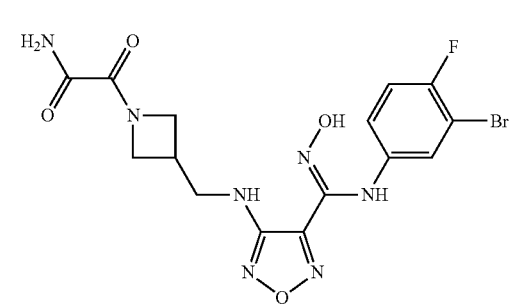 |
| 84 | 89 |
| 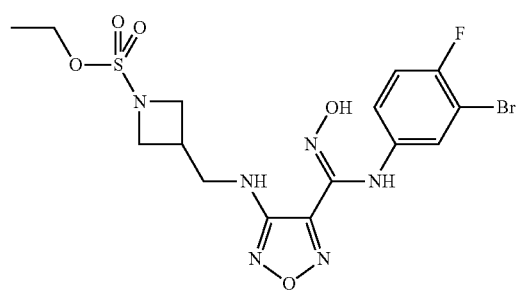 | 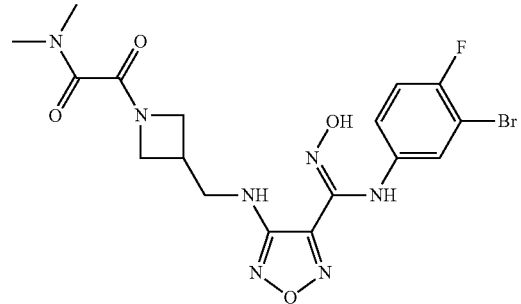 |
| 85 | 90 |
| 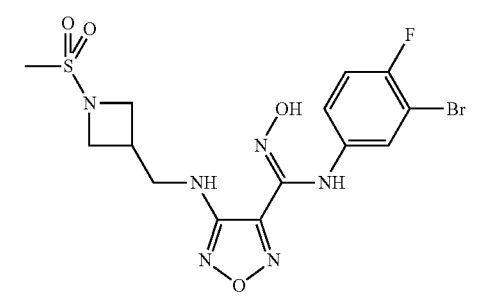 | 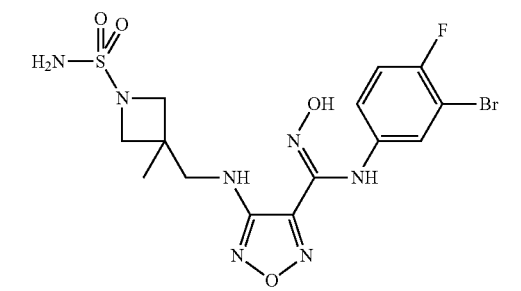 |
| 86 | 91 |
| 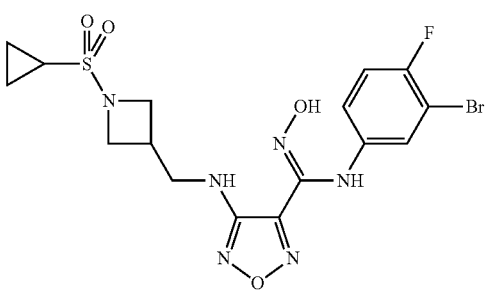 | 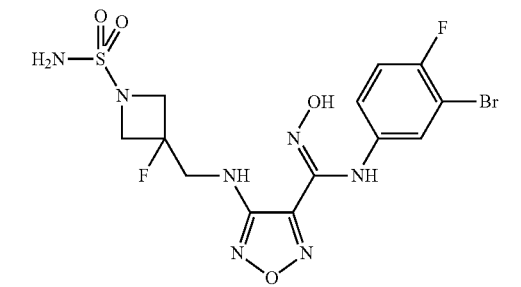 |

92
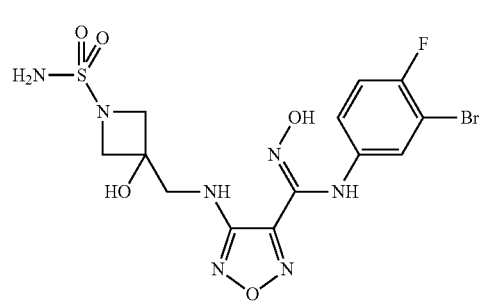
93
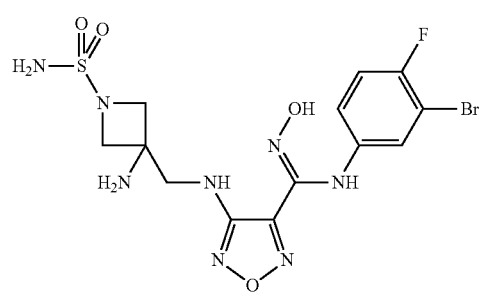
94
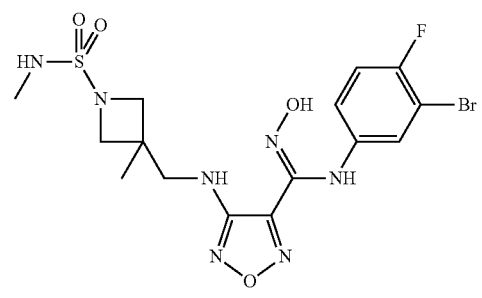
95
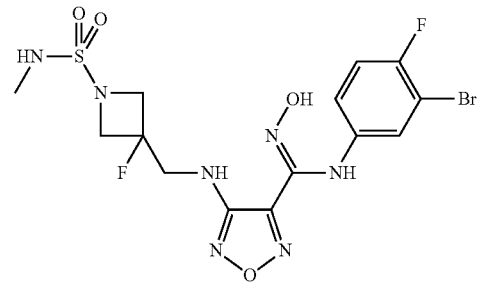
96
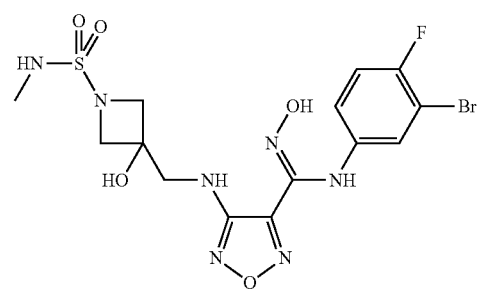
97
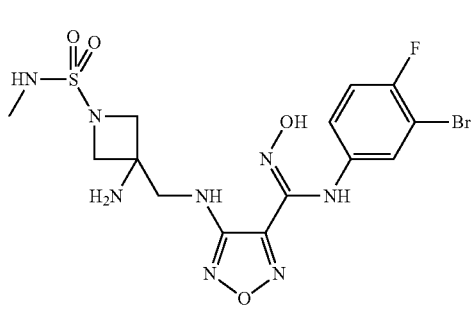
98
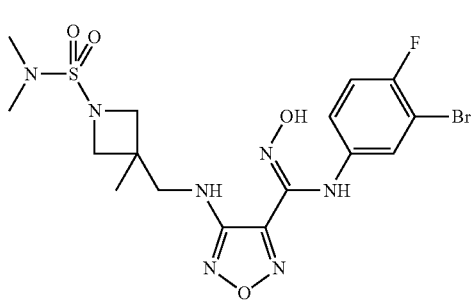
99
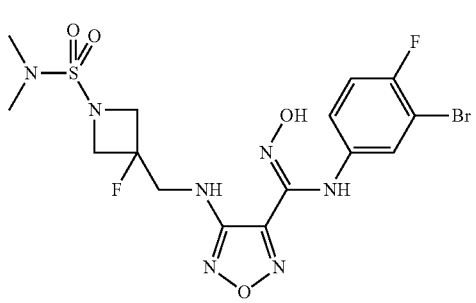
100
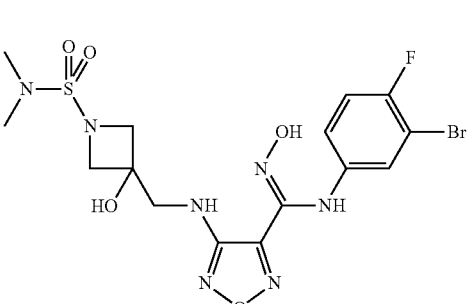
101
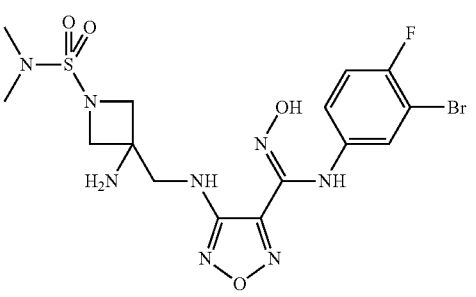

-continued
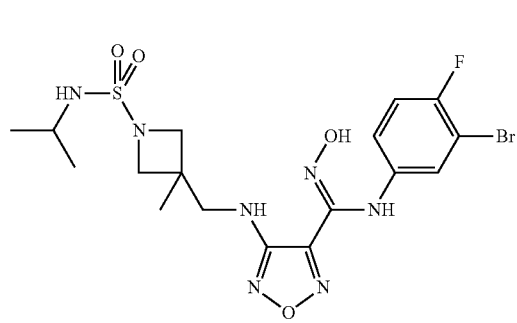
102
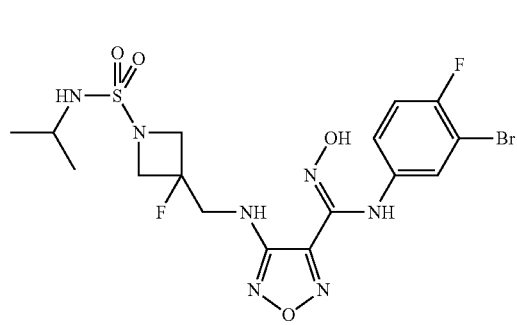
103
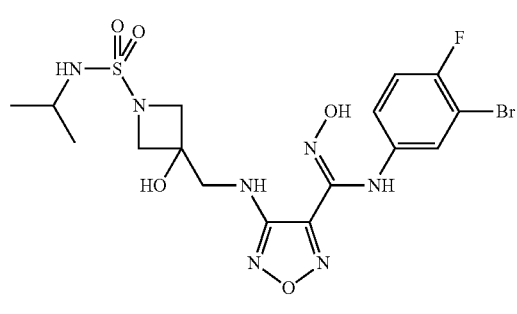
104
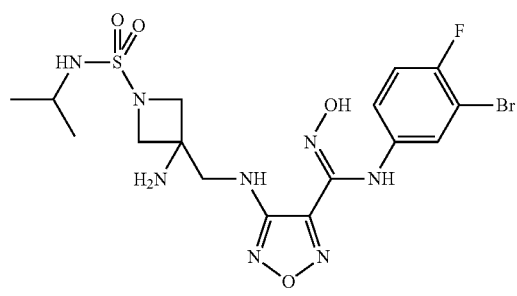
105
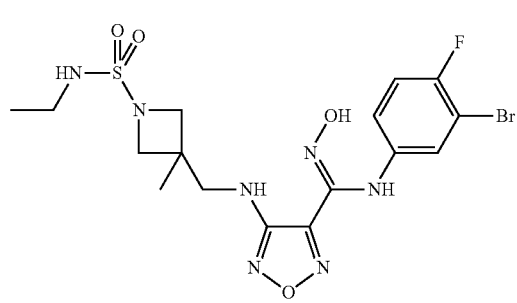
106
-continued
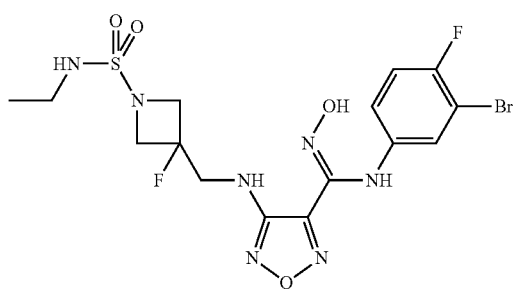
107
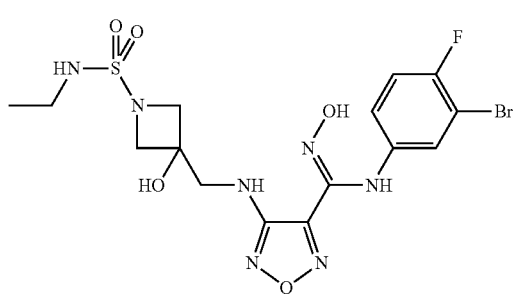
108
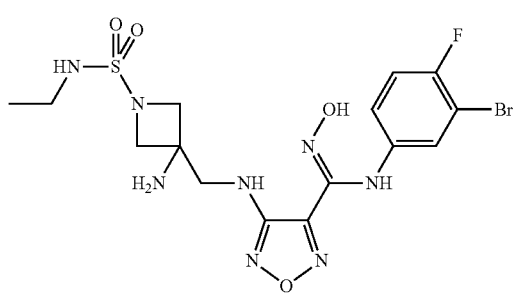
109
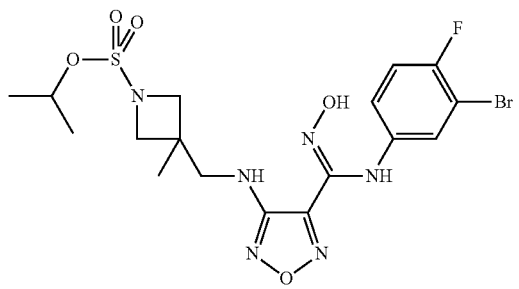
110
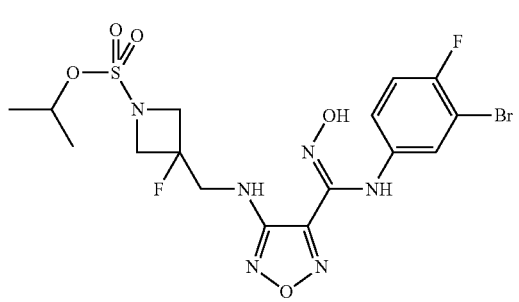
111

112
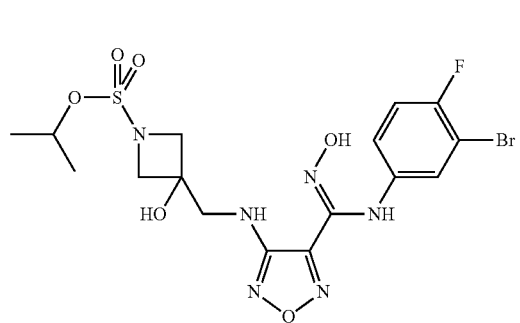
113
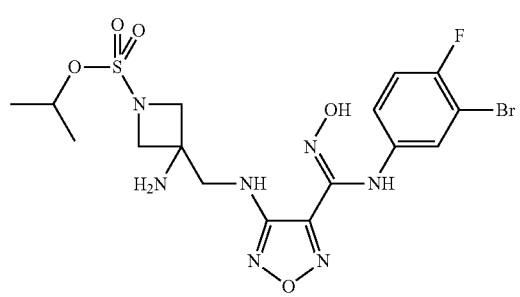
114
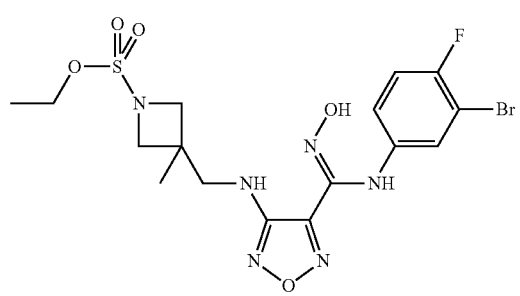
115
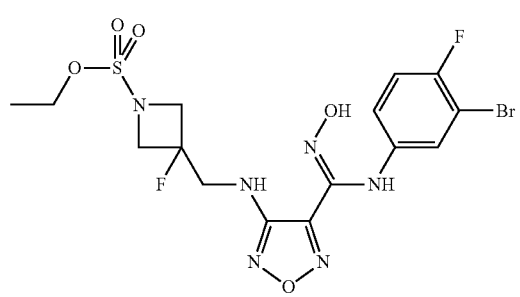
116
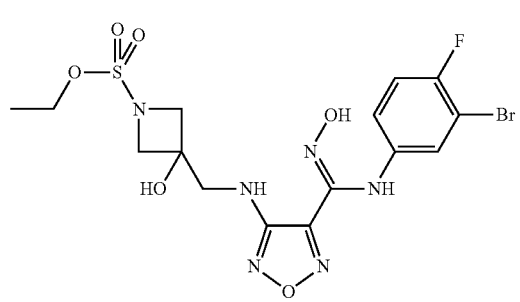
117
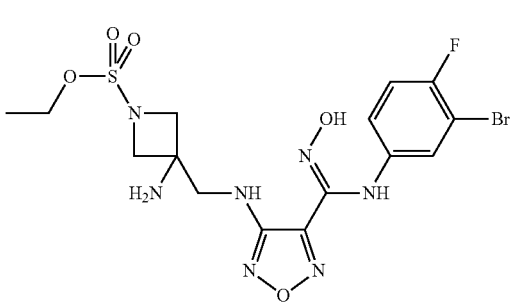
118
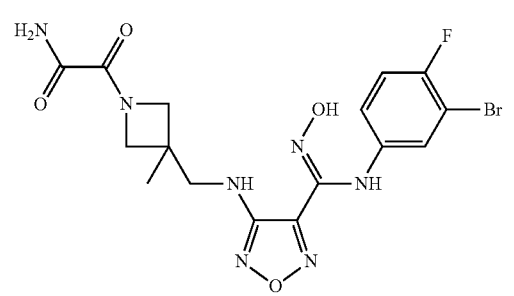
119
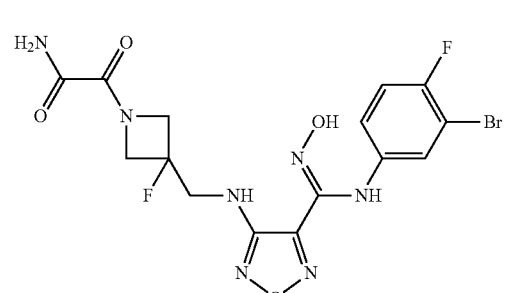
120
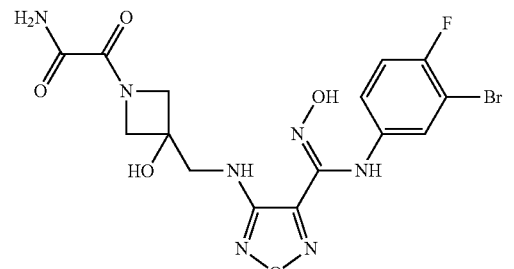
121
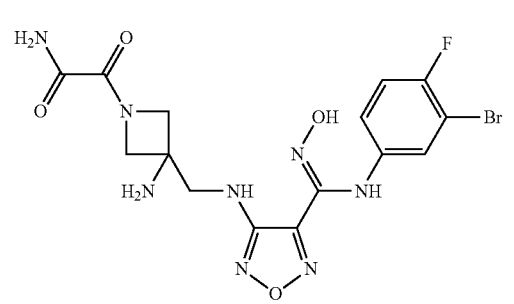

-continued
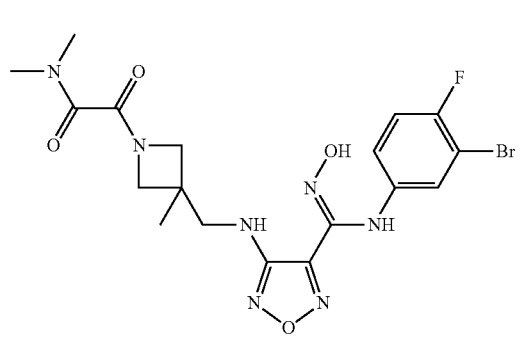 122
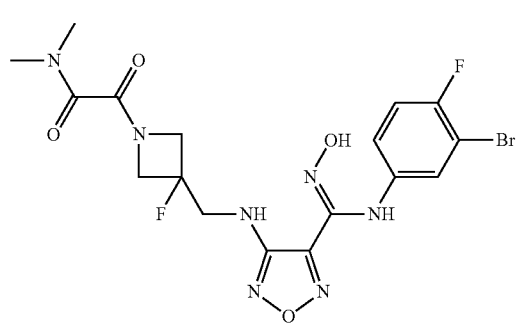 123
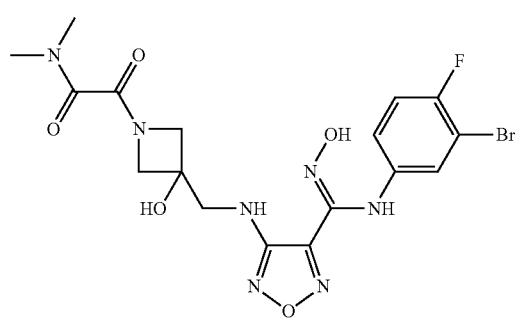 124
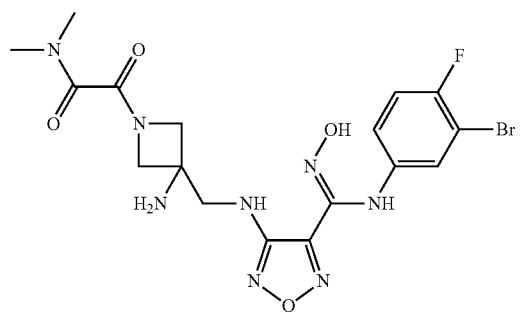 125
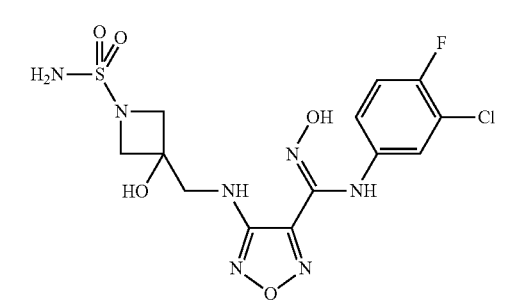 126
-continued
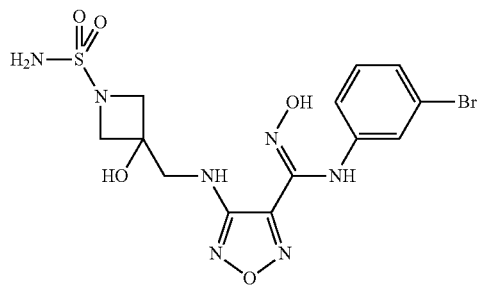 127
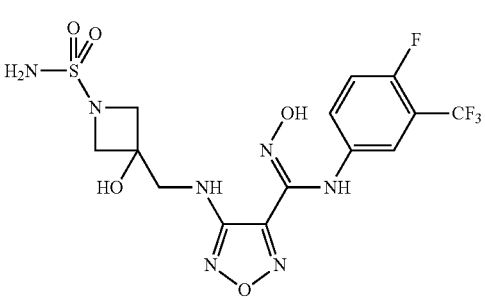 128
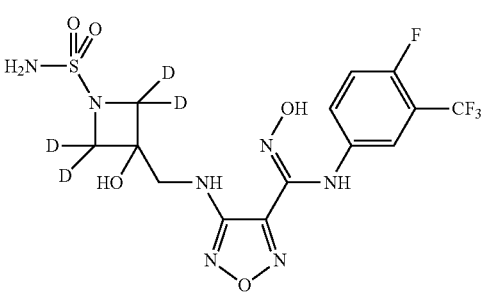 129
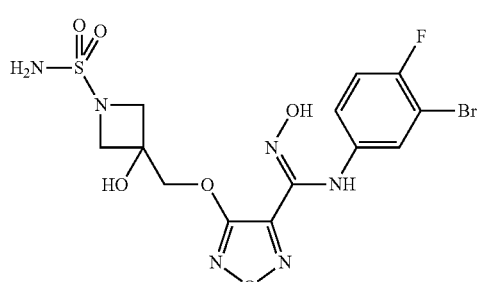 130
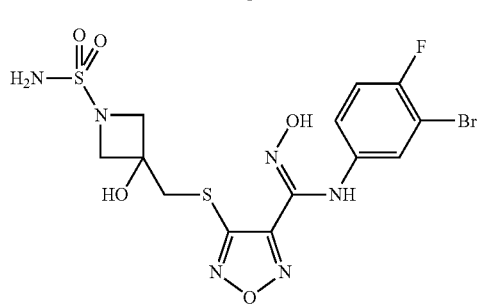 131

132
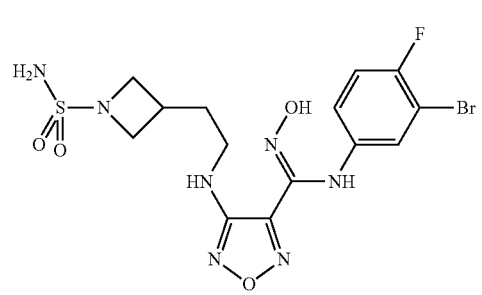
133
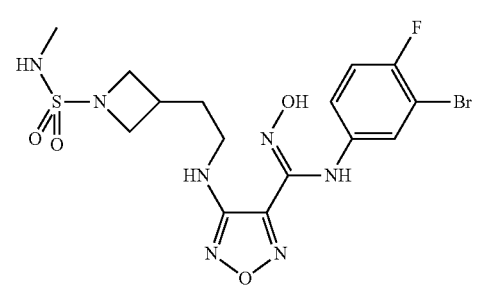
132
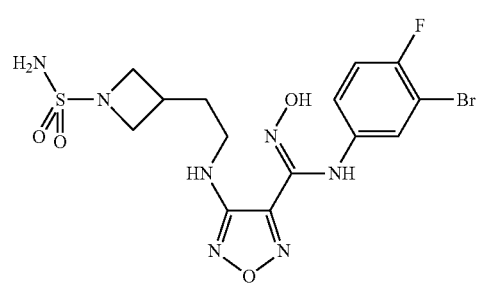
133
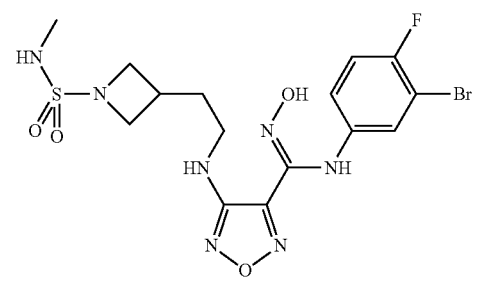
134
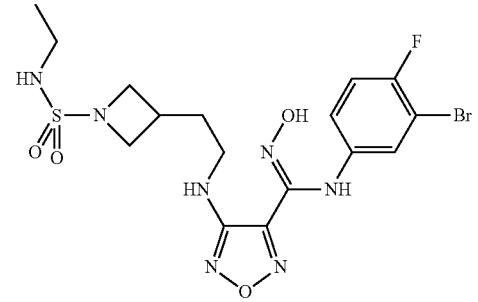
135
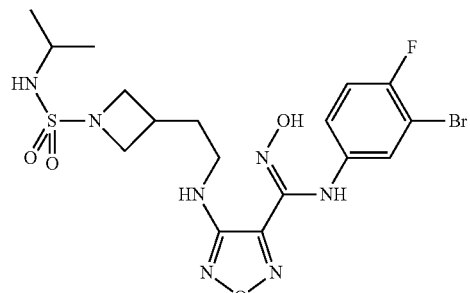
136
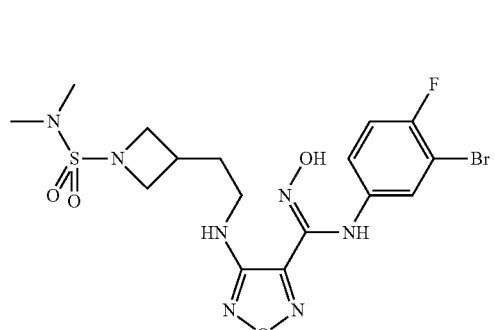
137
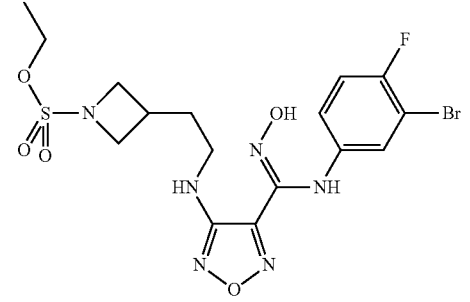
138
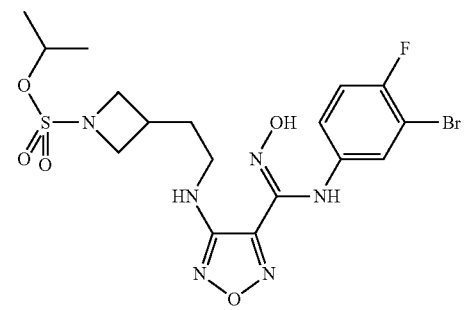
139
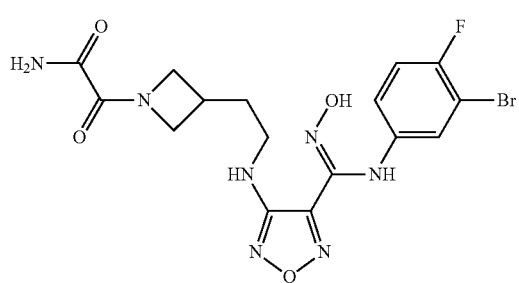

140 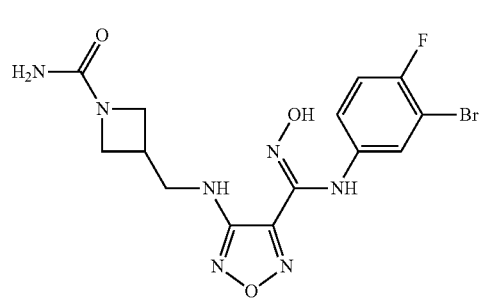
141 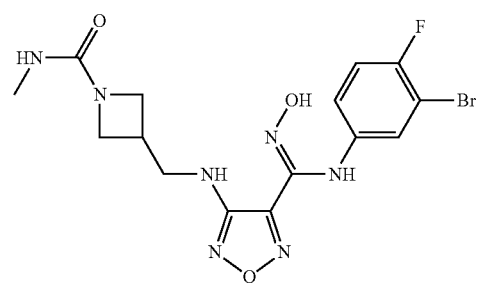
142 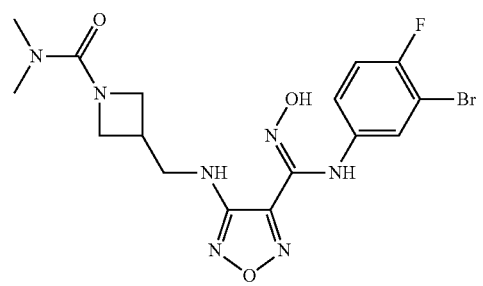
143 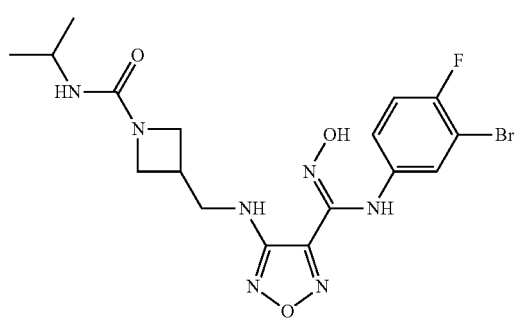
144 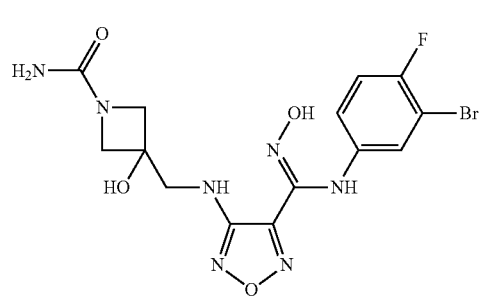
145 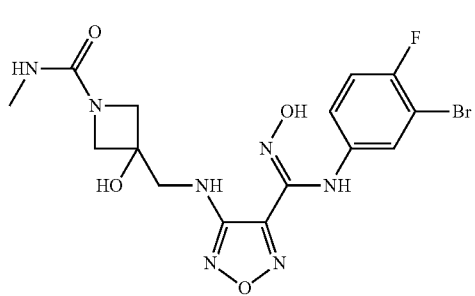
146 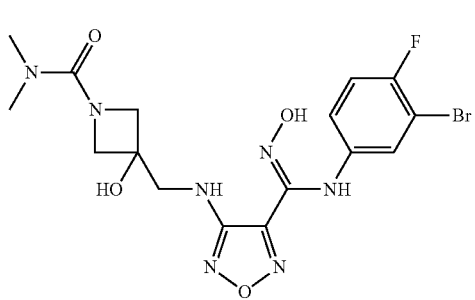
147 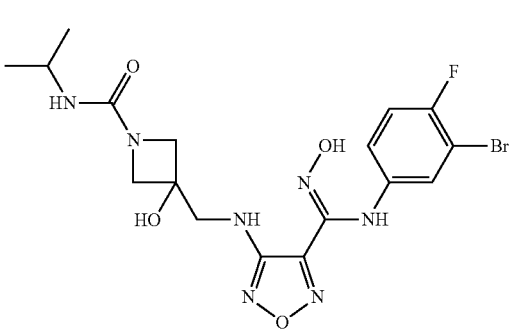
148 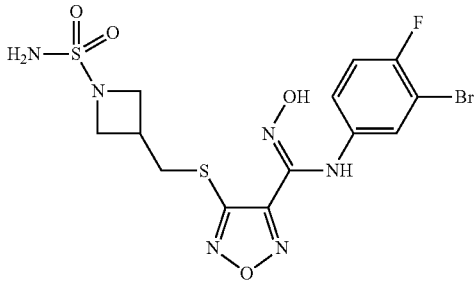
149 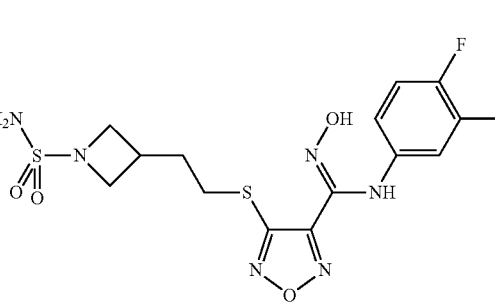

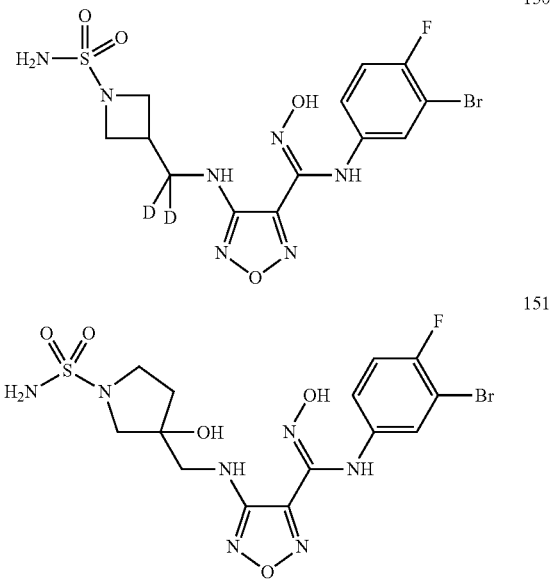

The present invention also provides the use of said compounds, or optical isomers thereof, or cis- and trans-isomers thereof, or solvates thereof, or pharmaceutically acceptable salts thereof, or pro-drugs thereof in the preparation of drugs for the prevention and/or treatment of diseases with pathological characteristics of IDO mediated tryptophan metabolism pathway.

The present invention also provides the use of said compounds, or optical isomers thereof, or cis- and trans-isomers thereof, or solvates thereof, or pharmaceutically acceptable salts thereof, or pro-drugs thereof, or tautomers thereof, or mesomers thereof, or racemates thereof, or enantiomers thereof, or diastereoisomers thereof, or mixtures thereof, or metabolites thereof, or metabolic precursors thereof in the preparation of IDO inhibitors.

Further, the diseases with pathological characteristics of IDO mediated tryptophan metabolism pathway are selected from cancer, myelodysplastic syndrome, Alzheimer's disease, autoimmune disease, depression, anxiety disorder, cataract, psychological disorder and AIDS; in which said cancer is preferably breast cancer, cervical cancer, colon cancer, lung cancer, gastric cancer, rectal cancer, pancreatic cancer, brain cancer, skin cancer, oral cancer, prostate cancer, bone cancer, kidney cancer, ovarian cancer, bladder cancer, liver cancer, fallopian tube tumor, ovarian tumor, peritoneal tumor, stage IV melanoma, solid tumor, glioma, neuroglioblastoma, hepatocyte cancer, and mastoid nephroma.

The present invention also provides a drug combination, characterized in that said drug combination is a formulation prepared by using said compounds, or optical isomers thereof, or cis- and trans-isomers thereof, or solvates thereof, or pharmaceutically acceptable salts thereof as active ingredients, with the addition of pharmaceutically acceptable excipients.

In the present invention, "substitution" means that the hydrogen atom in the molecule is replaced by other different atoms or molecules.

In the present invention, the minimum and maximum values of carbon atom content in the hydrocarbon group are indicated by a prefix, for example, the prefix Ca-b alkyl indicates any alkyl group having "a"~"b" carbon atoms, including straight chain alkyl group and branched chain alkyl group. Therefore, for example, C1-6 alkyl refers to a straight chain alkyl and a branched alkyl containing 1-6 carbon atoms.

In the present invention, halogen refers to fluorine, chlorine, bromine, and iodine.

In the present invention, "cycloalkyl" denotes the saturated or non-aromatic unsaturated ring formed only by carbon atoms.

In the present invention, "heterocycloalkyl" denotes a saturated or non-aromatic unsaturated ring containing at least one heteroatom, in which heteroatom means nitrogen, oxygen and sulfur.

In the present invention, "aryl" denotes the aromatic unsaturated ring formed only by carbon atoms.

In the present invention, in general, "pharmaceutically acceptable" means that carriers, vectors, diluents, excipients and/or salts formed are chemically or physically compatible with other components consisting of a pharmaceutical dosage, and physiologically compatible with the receptor.

Pharmaceutically acceptable excipients of the present invention denote the substances contained in the dosage except for the active ingredients.

IDO inhibitors are a class of drugs that can be used to treat cancer, myelodysplastic syndrome, Alzheimer's disease, autoimmune diseases, depression, anxiety, cataracts, psychological disorders, and AIDS.

The compounds of the present invention show excellent inhibitory activity against IDO enzyme and cells, as well as can be prepared as IDO inhibitors and treat a variety of diseases including tumors. Meanwhile, the compounds have good pharmacokinetic characteristics, and has great application potential in the field of cancer treatment related to IDO inhibition.

Obviously, based on above content of the present invention, according to the common technical knowledge and the conventional means in the field, without department from above basic technical spirits, other various modifications, alternations or changes can further be made.

By following specific examples of said embodiments, above content of the present invention is further illustrated. But it should not be construed that the scope of above subject of the present invention is limited to following examples. The techniques realized based on above content of the present invention are all within the scope of the present invention.

EXAMPLES

Synthesis of Compounds According to the Present Invention

General Synthetic Route:

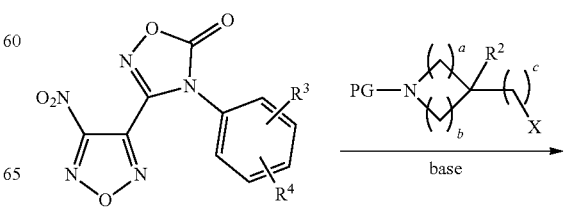

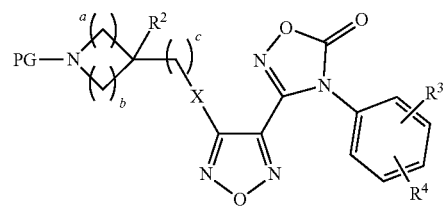
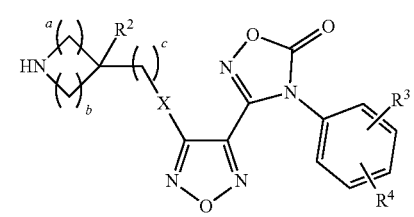
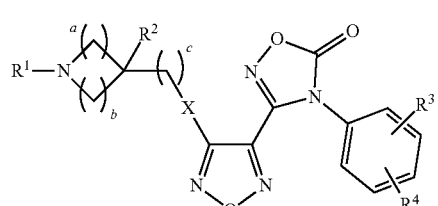
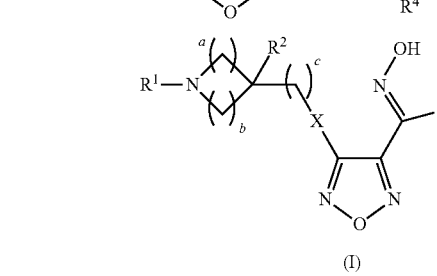
(I)
PG is a protective group, including but not limited to Boc, Fmoc, etc.
Following compounds are prepared.
Example 1: Synthetic Route of N-(3-bromo-4-fluorophenyl)-N'-hydroxyl-4-(((1-sulfamoylpyrrolidin-3-yl)methyl)amino)-1,2,5-oxadiazole-3-formamidine (Compound 7)
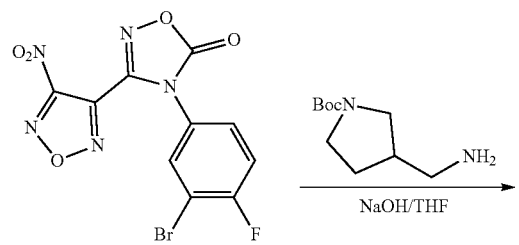
1
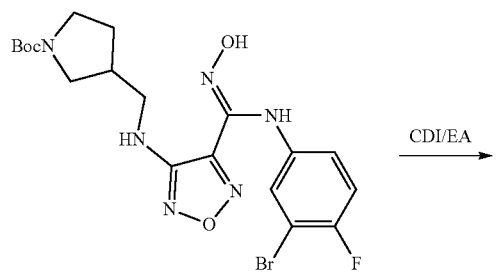
7.1
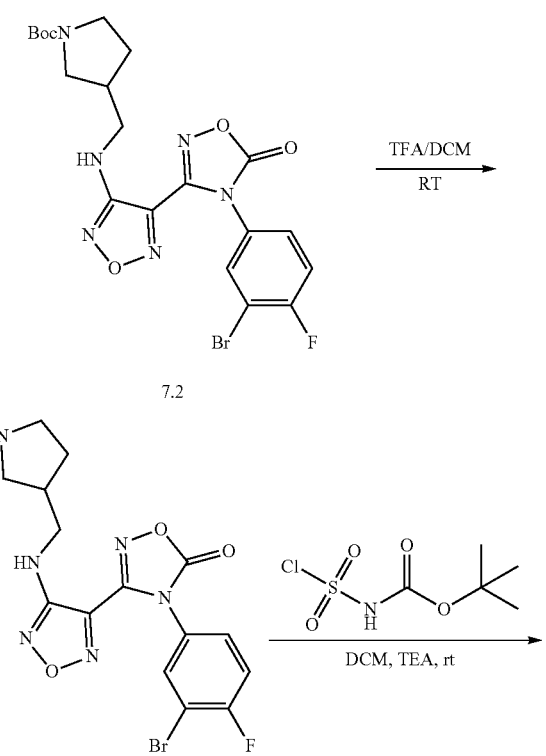
7.2
7.3
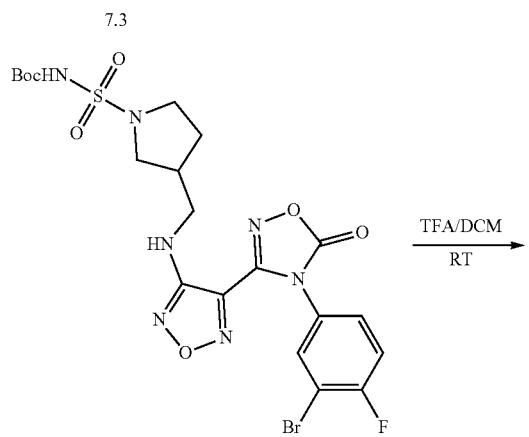
7.4

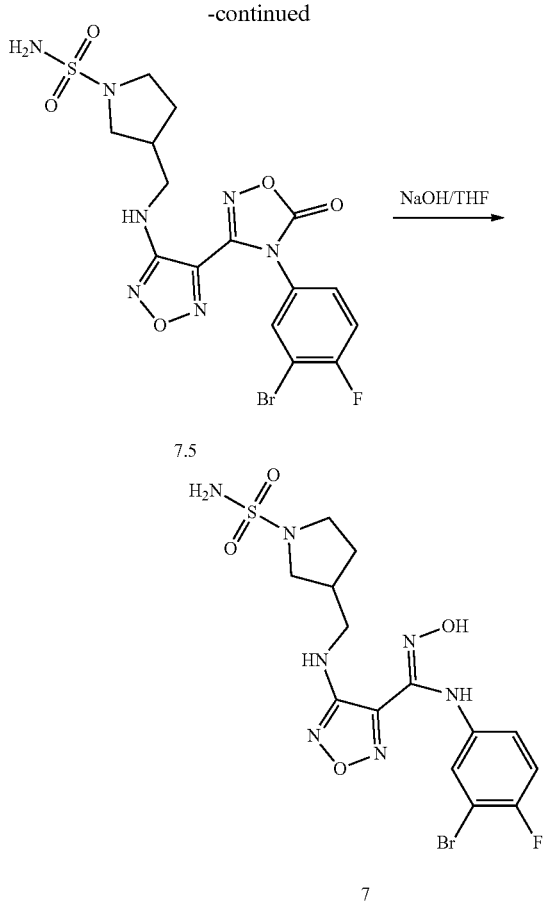

(1) Synthesis of Compound 1

To 380 mL trifluoroacetic acid, was added 3-(4-amino-1,2,5-oxadiazol-3-yl)-4-(3-bromo-4-fluorophenyl)-1,2,4-oxadiazol-5(4H)-one (26 g, 76.01 mmol), then 230 mL hydrogen peroxide solution was added, and the mixture was allowed to react 12 h at the temperature of 55° C.~60° C. After completion of the reaction, the solution was cooled down, poured into 1 L ice water, and the solid precipitated under stirring. After filtration, the solid was washed twice with 100 mL water, and the resultant solid was compound 1. After drying, the solid weighed 13.57 g (brown yellow solid), with a yield of 48%. $^1$HNMR (DMSO-$d_6$, 400 MHz): δ 8.05 (dd, J=2.4, 6.0 Hz, 1H), 7.67 (m, J=2.4, 4.4 Hz, 1H), 7.57 (t, J=8.8, 17.6 Hz, 1H).

(2) Synthesis of Compound 7.1

Compound 1 (312.53 mg, 0.84 mmol) was dissolved in 22.5 mL tetrahydrofuran, to which were successively added 1-tert-butoxycarbonyl-3-(aminomethyl)pyrrolidine (336.47 mg, 1.68 mmol) and 2.25 mL 2.5 M sodium hydroxide solution, and the mixture was stirred for 30 minutes. After completion of the reaction, 50 mL saturated aqueous solution of ammonium chloride was added to the reaction solution, and then extracted with ethyl acetate (50 mL). The resultant organic phase was washed with 0.2 N hydrochloric acid (50 mL), dried with anhydrous sodium sulfate, filtered, and the filtrate was concentrated under reduced pressure to obtain crude product 7.1 (382 mg, yellow solid). The product was directly used in the next step without purification. MS (ESI): m/z 499.1 (M+H)$^+$.

(3) Synthesis of Compound 7.2

Compound 7.1 (379.49 mg, 0.76 mmol) was dissolved in 20 mL ethyl acetate, to which was added N,N-carbonyldiimidazole (184.85 mg, 1.14 mol). The reaction was refluxed 0.5 h under stirring. After completion of the reaction, the solution was cooled, and then washed with 0.2 N aqueous hydrochloric acid (50 mL). The organic phase was dried with anhydrous sodium sulfate, filtered, and the filtrate was concentrated under reduced pressure to obtain the crude product 7.2 (362 mg, yellow solid), that was directly used in the next step without purification. MS (ESI): m/z 525.1 (M+H)$^+$.

(4) Synthesis of Compound 7.3

Compound 7.2 (360 mg, 0.689 mmol) was dissolved in 3 ml dichloromethane, to which was added 1.5 ml trifluoroacetic acid, and the reaction was stirred for 1 h. After completion of the reaction, the reaction solution was concentrated under reduced pressure to obtain the crude title product 7.3 (320 mg, yellow oil). The resultant product was directly used in the next step without purification. MS (ESI): m/z 425.2 (M+H)$^+$ (5) Synthesis of Compound 7.4

Chlorosulfonic acid isocyanate (0.212 g, 1.5 mmol) was dissolved in 5 mL dichloromethane, then cooled to 0° C., to which was added t-butanol (0.115 g, 1.55 mmol). The reaction solution reacted at 0° C. for 1 h, to obtain the reaction solution A. Compound 7.3 (320 mg, 0.752 mmol) was dissolved in 5 mL dichloromethane, and 1.0 mL triethylamine was added, to obtain the reaction solution B. Reaction solution A was added to reaction solution B at 0° C., and the mixture was allowed to react for 1 h at 0° C. After completion of the reaction, the saturated aqueous solution of sodium bicarbonate was added to quench the reaction. The solution was separated, and the organic phase was washed with 0.2 N hydrochloric acid, dried by anhydrous sodium sulfate, filtered. The filtrate was concentrated under reduced pressure, and purified by TLC using the development system of dichloromethane/methanol=10:1, to obtain the product 7.4 (291 mg, white solid). MS (ESI): m/z 604.06 (M+H)$^+$.

(6) Synthesis of Compound 7.5

Compound 7.4 (290 mg, 0.480 mmol) was dissolved in 3 mL dichloromethane, then 1.5 mL trifluoroacetic acid was added, and the mixture was stirred for 1 h. After completion of the reaction, the reaction solution was concentrated under reduced pressure to obtain the crude product 7.5 (265 mg, white solid). The product was directly used in the next step without purification. MS (ESI): m/z 504.01 (M+H)$^+$.

(7) Synthesis of Compound 7

Compound 7.5 (260 mg, 0.516 mmol) was dissolved in 2 mL tetrahydrofuran, and 0.5 mL of 2.0 N sodium hydroxide solution was added at 0° C., then the reaction mixture was stirred for 1 hour. After completion of the reaction, saturated aqueous solution of ammonium chloride (5 mL) was added to the reaction solution, then extracted with ethyl acetate, and the resultant organic phase was dried with anhydrous sodium sulfate and filtered. The filtrate was concentrated under reduced pressure, and purified by TLC using dichloromethane/methanol=10:1 as development solvent, to obtain the title product 7 (185 mg, white solid).

$^1$H NMR (DMSO-$d_6$, 400 MHz): δ 11.46 (s, 1H), 8.92 (s, 1H), 7.19 (t, J=8.4, 17.6 Hz, 1H), 7.12-7.10 (m, 1H), 6.78-6.71 (m, 3H), 6.39-6.37 (m, 1H), 3.27-3.07 (m, 5H), 2.90-2.85 (m, 1H), 2.55-2.51 (m, 1H), 1.94-1.89 (m, 1H), 1.59-1.54 (m, 1H). MS (ESI): m/z 478 (M+H)$^+$.

Compounds of following examples were prepared by a synthetic method similar to above example 1.

Example 2: 4-((Azetidin-3-ylmethyl)amino)-N-(3-bromo-4-fluorophenyl)-N'-hydroxyl-1,2,5-oxadiazole-3-formamidine (Compound 2)

By the synthetic method similar to that of example 1, using compound 1 and t-butanol 3-(aminomethyl)azetidin-1-formate as starting material, compound of example 2 was prepared.

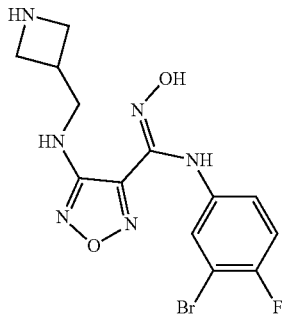 [SMILES: O/N=C(\Nc1ccc(F)c(Br)c1)c1nonc1NCC1CNC1]

$^1$H NMR (DMSO-d$_6$, 400 MHz): δ 8.93 (s, 1H), 7.19 (t, J=8.8, 17.2 Hz, 1H), 7.11-7.09 (m, J=2.8, 6.0 Hz, 1H), 6.77-6.75 (m, J=3.2, 4.8 Hz, 1H), 6.48 (m, 1H), 3.89 (t, J=8.8, 17.6 Hz, 2H), 3.65 (t, J=7.2, 16.4 Hz, 2H), 3.51-3.35 (m, 3H), 3.02 (m, 1H). MS (ESI): m/z 385 (M+H)$^+$.

Example 3: t-Butyl 3-(((4-(N-(3-bromo-4-fluorophenyl)-N'-hydroxylformamidinyl)-1,2,5-oxadiazole-3-yl)amino)methyl)azetidin-1-formate (Compound 3)

By the synthetic method similar to that of example 1, using compound 1 and t-butanol 3-(aminomethyl)azetidin-1-formate as starting material, compound of example 3 was prepared.

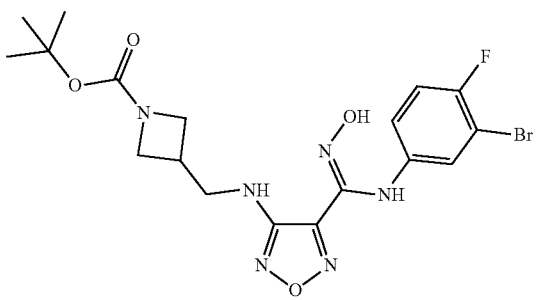 [SMILES: CC(C)(C)OC(=O)N1CC(CNc2nonc2/C(=N/O)Nc2ccc(F)c(Br)c2)C1]

$^1$H NMR (400 MHz, DMSO-d$_6$): δ 11.42 (s, 1H), 8.93 (s, 1H), 7.18 (t, J=8.8, 17.6 Hz, 1H), 7.12-7.10 (m, J=2.4, 6.0 Hz, 1H), 6.77-6.73 (m, 1H), 6.40 (t, J=6.0, 12.0 Hz, 1H), 3.86 (t, J=8.0, 16.0 Hz, 2H), 3.53 (m, 2H), 3.54-3.37 (m, 2H), 2.79-2.76 (m, 1H), 1.37 (m, 9H). MS (ESI): m/z (M+H)$^+$ 485.1.

Example 4: N-(3-Bromo-4-fluorophenyl)-N'-hydroxyl-4-(((1-sulfamoylazetidin-3-yl)methyl)amino)-1,2,5-oxadiazole-3-formamidine (Compound 4)

By the synthetic method similar to that of example 1, using compound 3 as starting material, compound of example 4 was prepared.

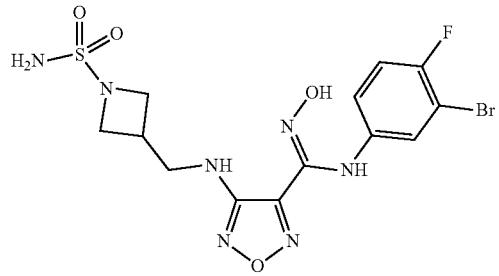 [SMILES: NS(=O)(=O)N1CC(CNc2nonc2/C(=N/O)Nc2ccc(F)c(Br)c2)C1]

$^1$H NMR (DMSO-d$_6$, 400 MHz): δ 11.43 (s, 1H), 8.93 (m, 1H), 7.19-7.0 (m, 2H), 6.91 (m, 2H), 6.84-6.77 (m, 1H), 6.40 (m, 1H), 3.75-3.41 (m, 8H), 2.74 (m, 1H). MS (ESI): m/z 464.2 (M+H)$^+$.

Example 5: t-Butyl 3-(((4-(N-(3-bromo-4-fluorophenyl)-N'-hydroxylformamidinyl)-1,2,5-oxadiazole-3-yl)amino)methyl)azetidin-1-formate (Compound 5)

By the synthetic method similar to that of example 1, using compound 1 and t-butanol 3-(aminomethyl)azetidin-1-formate as starting material, compound of example 5 was prepared.

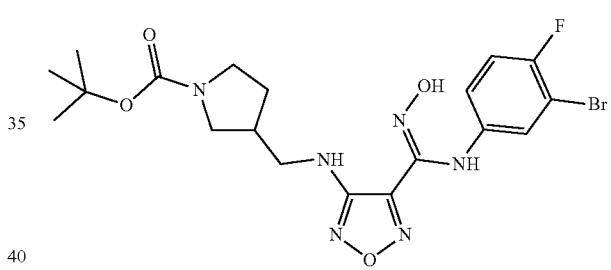

MS (ESI): m/z (M+H)$^+$ 499.1.

Example 6: N-(3-Bromo-4-fluorophenyl)-N'-hydroxyl-4-((azacyclopentan-3-ylmethyl)amino)-1,2,5-oxadiazole-3-formamidine (Compound 6)

By the synthetic method similar to that of example 1, using compound 1 and t-butanol 3-(aminomethyl)azacyclopentan-1-formate as starting material, compound of example 6 was prepared.

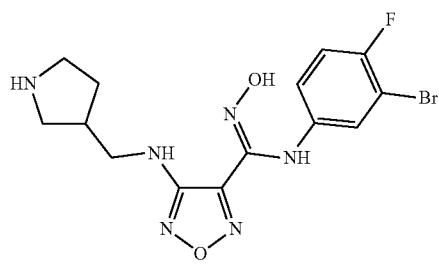 [SMILES: O/N=C(\Nc1ccc(F)c(Br)c1)c1nonc1NCC1CCNC1]

MS (ESI): m/z (M+H)$^+$ 399.

Example 7: N-(3-bromo-4-fluorophenyl)-N'-hydroxyl-4-(((1-sulfamoylpyrrolidine-3-yl)methyl)amino)-1,2,5-oxadiazole-3-formamidine By the synthetic method similar to that of example 1, using compound 1 and t-butanol 3-(aminomethyl)azacyclopentan-1-formate as starting material, compound of example 7 was prepared.

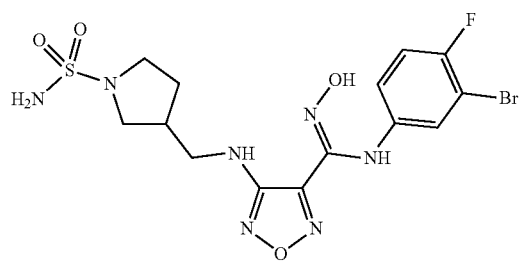 [SMILES: NS(=O)(=O)N1CCC(CNc2nonc2/C(=N/O)Nc2ccc(F)c(Br)c2)C1]

$^1$H NMR (DMSO-d$_6$, 400 MHz): δ 11.46 (s, 1H), 8.92 (s, 1H), 7.19 (t, J=8.4, 17.6 Hz, 1H), 7.12-7.10 (m, 1H), 6.78-6.71 (m, 3H), 6.39-6.37 (m, 1H), 3.27-3.07 (m, 5H), 2.90-2.85 (m, 1H), 2.55-2.51 (m, 1H), 1.94-1.89 (m, 1H), 1.59-1.54 (m, 1H). MS (ESI): m/z 478 (M+H)$^+$.

Example 8: (S)—N-(3-Bromo-4-fluorophenyl)-N'-hydroxyl-4-(((1-sulfamoylpyrrolidine-3-yl)methyl)amino)-1,2,5-oxadiazole-3-formamidine Compound 8)

By the synthetic method similar to that of example 1, using compound 1 and (S)-t-butanol 3-(aminomethyl)azacyclopentan-1-formate as starting material, compound of example 8 was prepared.

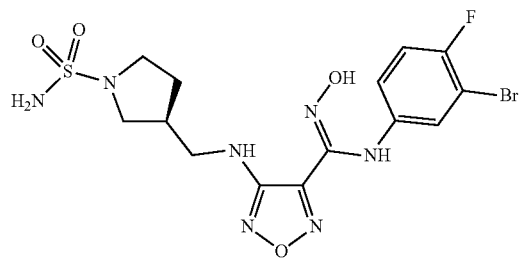 [SMILES: NS(=O)(=O)N1CC[C@@H](CNc2nonc2/C(=N/O)Nc2ccc(F)c(Br)c2)C1]

MS (ESI): m/z (M+H)$^+$478.

Example 9: (R)—N-(3-bromo-4-fluorophenyl)-N'-hydroxyl-4-(((1-sulfamoylpyrrolidine-3-yl)methyl)amino)-1,2,5-oxadiazole-3-formamidine (Compound 9)

By the synthetic method similar to that of example 1, using compound 1 and (R)-t-butanol 3-(aminomethyl)azacyclopentan-1-formate as starting material, compound of example 9 was prepared.

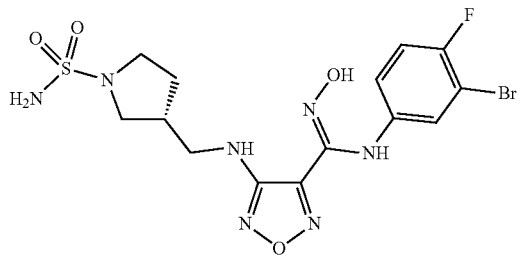 [SMILES: NS(=O)(=O)N1CC[C@H](CNc2nonc2/C(=N/O)Nc2ccc(F)c(Br)c2)C1]

MS (ESI): m/z (M+H)$^+$ 478.

Example 10: N-(3-bromo-4-fluorophenyl)-N'-hydroxyl-4-(((1-sulfamoylpiperidin-3-yl)methyl)amino)-1,2,5-oxadiazole-3-formamidine (Compound 10)

By the synthetic method similar to that of example 1, using compound 1 and t-butanol 3-(aminomethyl)azetidin-1-formate as starting material, compound of example 10 was prepared.

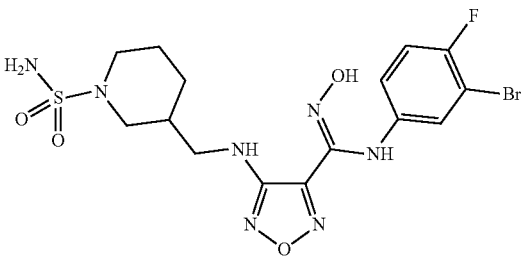 [SMILES: NS(=O)(=O)N1CCCC(CNc2nonc2/C(=N/O)Nc2ccc(F)c(Br)c2)C1]

$^1$HNMR (400 Hz, DMSO-d$_6$): δ 11.459 (1H, s), 8.902 (1H, s), 7.204-7.160 (1H, t, J=8.8 Hz), 7.133-7.111 (1H, dd, J=6.2 Hz, 2.6 Hz), 6.774-6.734 (1H, m), 6.705 (2H, s), 6.290-6.260 (1H, t, J=6.0 Hz), 3.426-3.389 (1H, m), 3.345-3.294 (1H, m), 3.154-3.122 (2H, m), 2.544-2.523 (1H, m), 2.324-2.271 (1H, t, J=10.6 Hz), 1.958-1.880 (1H, m), 1.754-1.702 (1H, m), 1.660-1.620 (1H, m), 1.482-1.433 (1H, m), 1.049-0.952 (1H, m). MS (ESI): m/z 492 (M+H)$^+$.

Example 11: N-(3-bromo-4-fluorophenyl)-N'-hydroxyl-4-(((4-sulfamoylmorpholin-2-yl)methyl)amino)-1,2,5-oxadiazole-3-formamidine (11)

By the synthetic method similar to that of example 1, using compound 1 and t-butanol 2-(aminomethyl)morpholin-4-formate as starting material, compound of example 11 was prepared.

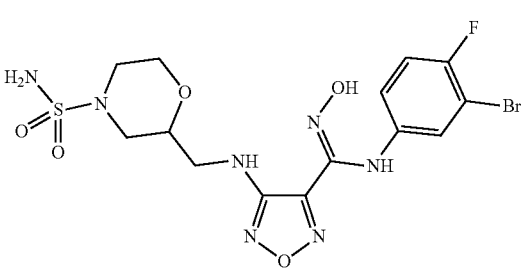 [SMILES: NS(=O)(=O)N1CCOC(CNc2nonc2/C(=N/O)Nc2ccc(F)c(Br)c2)C1]

MS (ESI): m/z (M+H)$^+$494.

Example 12: N-(3-Bromo-4-fluorophenyl)-N'-hydroxyl-4-(((1-sulfamoylazetidine-2-yl)methyl)amino)-1,2,5-oxadiazole-3-formamidine (12)

By the synthetic method similar to that of example 1, using compound 1 and t-butanol 2-(aminomethyl)azetidin-1-formate as starting material, compound of example 12 was prepared.

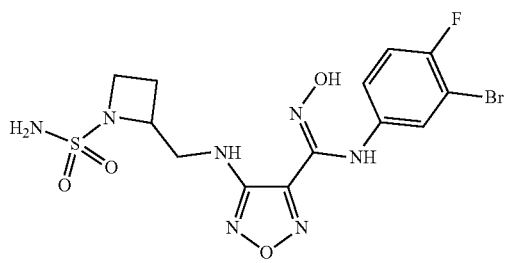 [SMILES: NS(=O)(=O)N1CCC1CNc1nonc1/C(=N/O)Nc1ccc(F)c(Br)c1]

¹H NMR (DMSO-d₆, 400 MHz): δ 11.54 (s, 1H), 8.88 (s, 1H), 7.21-7.16 (t, J=8.8 Hz, 1H), 7.14-7.12 (dd, J=6.2, 2.6 Hz, 1H), 6.98 (s, 2H), 6.81-6.77 (m, 1H), 6.29-6.26 (t, J=5.8 Hz, 1H), 4.30-4.22 (m, 1H), 3.73-3.66 (m, 1H), 3.53-3.48 (m, 1H), 3.46-3.43 (m, 2H), 2.11-2.02 (m, 2H). MS (ESI): m/z (M+H)⁺ 464.

Example 13: N-(3-Bromo-4-fluorophenyl)-N'-hydroxyl-4-(((1-sulfamoylazacyclopentan-2-yl)methyl)amino)-1,2,5-oxadiazole-3-formamidine (13)

By the synthetic method similar to that of example 1, using compound 1 and t-butanol 2-(aminomethyl)azacyclopentan-1-formate as starting material, compound of example 13 was prepared.

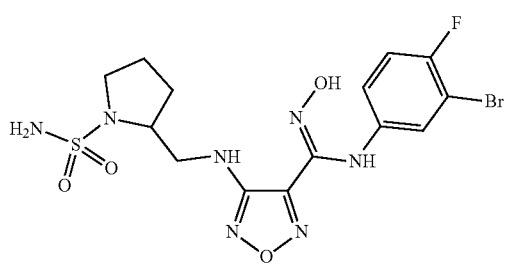 [SMILES: NS(=O)(=O)N1CCCC1CNc1nonc1/C(=N/O)Nc1ccc(F)c(Br)c1]

¹H NMR (DMSO-d₆, 400 MHz): δ 11.51 (s, 1H), 8.88 (s, 1H), 7.18 (t, J=8.8, 17.6 Hz, 1H), 7.13-7.11 (m, 1H), 6.80-6.76 (m, 3H), 6.20 (t, J=6.0, 12.4 Hz, 1H), 3.85-3.83 (m, 1H), 3.37-3.34 (m, 1H), 3.29-3.19 (m, 3H), 1.86-1.82 (m, 3H), 1.71-1.68 (m, 1H). MS (ESI): m/z 478.1 (M+H)⁺.

Example 14: N-(3-bromo-4-fluorophenyl)-N'-hydroxyl-4-(((1-sulfamoylazacyclohexane-2-yl)methyl)amino)-1,2,5-oxadiazole-3-formamidine (14)

By the synthetic method similar to that of example 1, using compound 1 and t-butanol 2-(aminomethyl)azacyclohexane-1-formate as starting material, compound of example 14 was prepared.

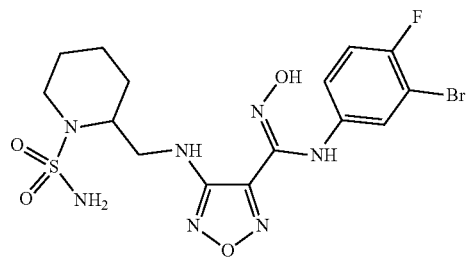 [SMILES: NS(=O)(=O)N1CCCCC1CNc1nonc1/C(=N/O)Nc1ccc(F)c(Br)c1]

¹HNMR (400 Hz, DMSO-d₆): δ 11.4 (1H, s), 8.87 (1H, s), 7.18-7.14 (1H, t, J=8.8 Hz), 7.13-7.11 (1H, t, J=3.4 Hz), 6.78-6.74 (1H, m), 6.66 (2H, s), 6.19-6.16 (1H, m), 4.07-4.02 (1H, m), 3.56-3.50 (2H, m), 3.44-3.37 (1H, m), 3.01-2.95 (1H, m), 1.57-1.49 (6H, m). MS (ESI): m/z (M+H)⁺ 492.

Example 15: N-(3-bromo-4-fluorophenyl)-N'-hydroxyl-4-((2-(1-sulfamoylazetidine-2-yl)ethyl)amino)-1,2,5-oxadiazole-3-formamidine (15)

By the synthetic method similar to that of example 1, using compound 1 and t-butanol 2-(aminoethyl)azetidin-1-formate as starting material, compound of example 15 was prepared.

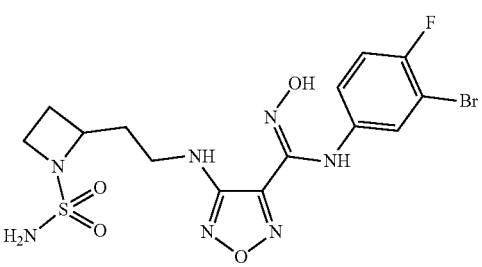 [SMILES: NS(=O)(=O)N1CCC1CCNc1nonc1/C(=N/O)Nc1ccc(F)c(Br)c1]

MS (ESI): m/z (M+H)⁺ 478.

Example 16: N-(3-bromo-4-fluorophenyl)-N'-hydroxyl-4-((2-(1-sulfamoylazacyclopentan-2-yl)ethyl)amino)-1,2,5-oxadiazole-3-formamidine (16)

By the synthetic method similar to that of example 1, using compound 1 and t-butanol 2-(aminoethyl)azacyclopentan-1-formate as starting material, compound of example 16 was prepared.

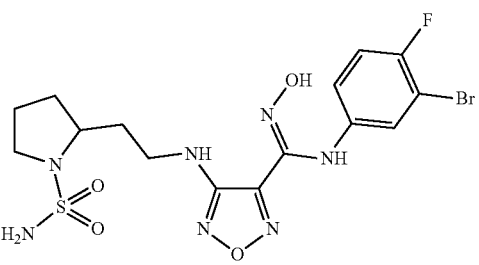 [SMILES: NS(=O)(=O)N1CCCC1CCNc1nonc1/C(=N/O)Nc1ccc(F)c(Br)c1]

¹H NMR (DMSO-d₆, 400 MHz): δ 11.44 (s, 1H), 8.89 (s, 1H), 7.19 (t, J=8.8, 17.6 Hz, 1H), 7.12-7.11 (m, 1H), 6.78-6.73 (m, 3H), 6.17-6.14 (m, 1H), 3.65-3.64 (m, 1H), 3.28-3.22 (m, 3H), 3.17-3.13 (m, 1H), 1.94-1.58 (m, 6H). MS (ESI): m/z (M+H)$^+$ 492.

Example 17: N-(3-bromo-4-fluorophenyl)-N'-hydroxyl-4-((2-(1-sulfamoylazacyclohexane-2-yl)ethyl)amino)-1,2,5-oxadiazole-3-formamidine (17)

By the synthetic method similar to that of example 1, using compound 1 and t-butanol 2-(aminoethyl)azacyclohexan-1-formate as starting material, compound of example 17 was prepared.

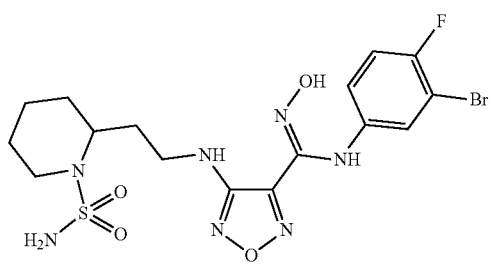 [SMILES: NS(=O)(=O)N1CCCCC1CCNc1nonc1/C(=N/O)Nc1ccc(F)c(Br)c1]

$^1$H NMR (DMSO-d$_6$, 400 MHz): δ 11.45 (s, 1H), 8.90 (s, 1H), 7.18 (t, J=8.8, 17.6 Hz, 1H), 7.11-7.09 (m, 1H), 6.78-6.67 (m, 3H), 6.20-6.17 (m, 1H), 3.30-3.20 (m, 2H), 2.25-2.23 (m, 1H), 1.72-1.69 (m, 1H), 1.53-1.46 (m, 4H), 1.49-1.46 (m, 1H). MS (ESI): m/z (M+H)$^+$ 506.2.

实施例 18: N-(3-bromo-4-fluorophenyl)-N'-hydroxyl-4-(((1-sulfamoylazacyclohexane-4-yl)methyl)amino)-1,2,5-oxadiazole-3-formamidine (18)

By the synthetic method similar to that of example 1, using compound 1 and t-butanol 4-(aminoethyl)azacyclohexan-1-formate as starting material, compound of example 18 was prepared.

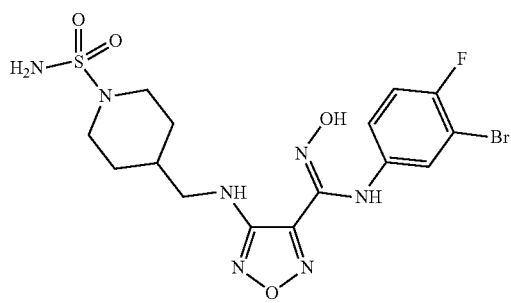 [SMILES: NS(=O)(=O)N1CCC(CNc2nonc2/C(=N/O)Nc2ccc(F)c(Br)c2)CC1]

$^1$H NMR (DMSO-d$_6$, 400 MHz): δ 11.43 (s, 1H), 8.92 (s, 1H), 7.19 (t, J=8.8, 17.6 Hz, 1H), 7.13-7.11 (m, 1H), 6.79-6.76 (m, 1H), 6.70 (s, 2H), 6.29 (t, J=6.0, 11.6 Hz, 1H), 3.47-3.44 (m, 2H), 3.11-3.08 (m, 2H), 2.49-2.42 (m, 2H), 1.68-1.65 (m, 3H), 1.23-1.17 (m, 2H). MS (ESI): m/z (M+H)$^+$ 492.

Example 19: N-(3-bromo-4-fluorophenyl)-N'-hydroxyl-4-((2-(1-sulfamoylazacyclohexane-4-yl)ethyl)amino)-1,2,5-oxadiazole-3-formamidine (19)

By the synthetic method similar to that of example 1, using compound 1 and t-butanol 4-(aminoethyl)azacyclohexan-1-formate as starting material, compound of example 19 was prepared.

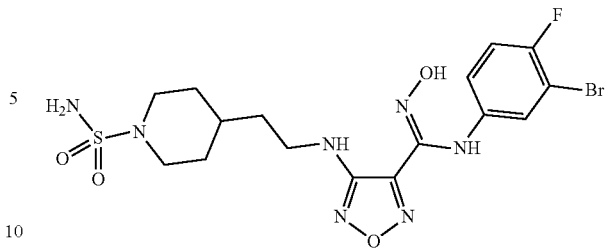

$^1$H NMR (DMSO-d$_6$, 400 MHz): δ 11.44 (s, 1H), 8.91 (s, 1H), 7.19 (t, J=8.4, 16.8 Hz, 1H), 7.11 (m, 1H), 6.78-6.68 (m, 3H), 6.17 (m, 1H), 3.44-3.42 (m, 2H), 3.24-3.23 (m, 2H), 2.47-2.44 (m, 2H), 1.77-1.74 (m, 2H), 1.50-1.49 (m, 2H), 1.19-1.17 (m, 3H). MS (ESI): m/z (M+H)$^+$ 506.2.

Example 20: N-(3-bromo-4-fluorophenyl)-N'-hydroxyl-4-(((1-methylsulfonylazacyclopentan-3-yl)methyl)amino)-1,2,5-oxadiazole-3-formamidine (20)

By the synthetic method similar to that of example 1, using compound 1 and t-butanol 3-(aminoethyl)azacyclopentan-1-formate as starting material, compound of example 20 was prepared.

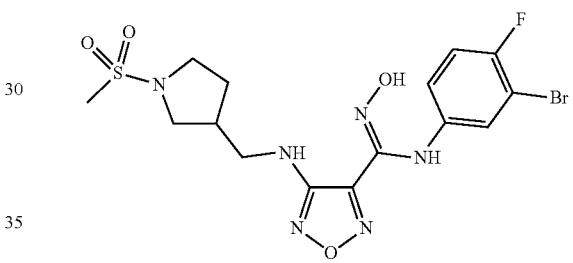

$^1$H NMR (400 MHz, DMSO-d$_6$) δ 11.44 (s, 1H), 8.92 (s, 1H), 7.21-7.16 (t, J=8.8 Hz, 1H), 7.12-7.10 (m, 1H), 6.79-6.75 (m, 1H), 6.41-6.38 (t, J=5.8 Hz, 1H), 3.37-3.28 (m, 2H), 3.25-3.22 (m, 2H), 3.21-3.18 (m, 1H), 2.99-2.94 (dd, J=10.0, 6.8 Hz, 1H), 2.89 (s, 3H), 2.60-2.55 (m, 1H), 1.99-1.94 (m, 1H), 1.66-1.59 (m, 1H). MS (ESI): m/z (M+H)$^+$ 477.

Example 21: N-(3-bromo-4-fluorophenyl)-N'-hydroxyl-4-(((1-cyclopropylsulfonylazacyclopentan-3-yl)methyl)amino)-1,2,5-oxadiazole-3-formamidine (21)

By the synthetic method similar to that of example 1, using compound 1 and t-butanol 3-(aminomethyl)azacyclopentan-1-formate as starting material, compound of example 21 was prepared.

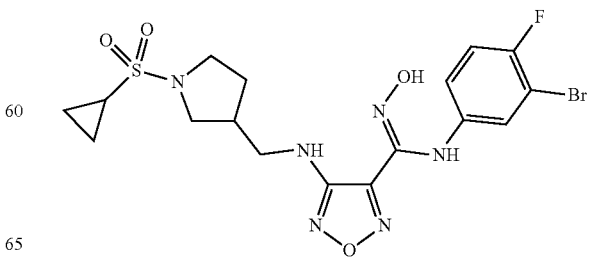

¹H NMR (400 MHz, DMSO-d₆): δ 11.45 (s, 1H), 8.93 (s, 1H), 7.19 (t, J=8.8, 17.6 Hz, 1H), 7.12-7.11 (m, 1H), 6.78-6.76 (m, 1H), 6.41 (m, 1H), 3.34-3.23 (m, 4H), 3.06-3.02 (m, 1H), 2.70-2.57 (m, 3H), 1.66-1.63 (m, 1H), 1.19-1.16 (m, 1H), 0.96-0.94 (m, 1H). MS (ESI): m/z (M+H)⁺ 503.

Example 22: (Z)—N-(3-bromo-4-fluorophenyl)-4-(((1-(N,N-methylsulfonyl)pyrrolidinyl-3-yl)methyl)amino)-N'-hydroxyl-1,2,5-oxadiazol-3-carboxyoximide (Compound 23)

Compound 23 was prepared by the method similar to that of example 1.

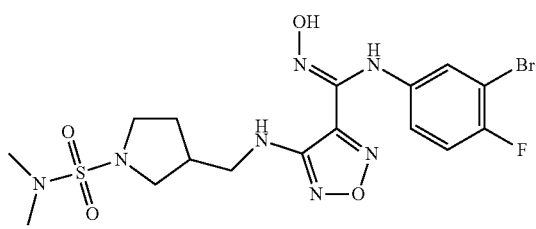 [SMILES: CN(C)S(=O)(=O)N1CCC(CNc2nonc2/C(=N/O)Nc2ccc(F)c(Br)c2)C1]

¹H NMR (400 MHz, DMSO-d₆) δ 11.44 (s, 1H), 8.92 (s, 1H), 7.18 (t, J=8.7 Hz, 1H), 7.11 (d, J=3.5 Hz, 1H), 6.78 (s, 1H), 6.39 (s, 1H), 3.27-3.17 (m, 5H), 3.00-2.91 (m, 1H), 2.74 (s, 1H), 2.73 (s, 6H), 1.62 (dd, J=12.2, 7.9 Hz, 1H), 1.36 (m, 2H). LC/MS (ESI+) calcd for C₁₆H₂₁BrFN₇O₄S ([M+H]⁺) m/z: 506.1; found 506.0.

Example 23: (Z)—N-(3-Bromo-4-fluorophenyl)-N'-hydroxyl-4-((1-sulfamoylpyrrolidin-3-yl)methoxyl)-1,2,5-oxadiazol-3-formamidine (Compound 27)

Compound 27 was prepared by the method similar to that of example 1.

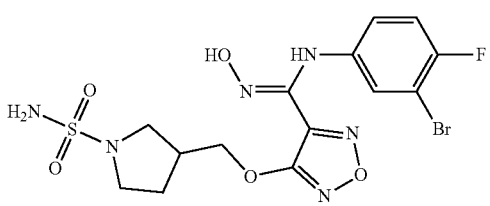 [SMILES: NS(=O)(=O)N1CCC(COc2nonc2/C(=N/O)Nc2ccc(F)c(Br)c2)C1]

¹H NMR (400 MHz, DMSO-d₆) δ 11.44 (s, 1H), 9.07 (s, 1H), 7.17 (t, J=8.7 Hz, 1H), 7.11 (dd, J=6.0, 2.7 Hz, 1H), 6.78 (s, 2H), 6.72-6.65 (m, 1H), 4.17 (t, J=7.6 Hz, 2H), 3.26-3.21 (m, 1H), 3.16-3.08 (m, 2H), 2.88 (dd, J=10.2, 6.5 Hz, 1H), 1.89 (dd, J=12.6, 5.3 Hz, 1H), 1.52 (dq, J=14.8, 7.4 Hz, 1H), 0.95 (t, J=7.1 Hz, 1H). LC/MS (ESI+) m/z, 479 (M+H⁺).

Example 24: N-(3-Bromo-4-fluorophenyl)-N'-hydroxyl-4-(((1-sulfamoylpyrrolidin-3-yl)methyl)thioether)-1,2,5-oxadiazol-3-amidine (Compound 28)

Compound 28 was prepared by the method similar to that of example 1.

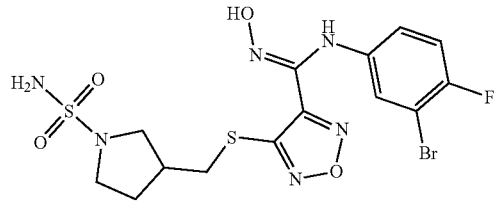 [SMILES: NS(=O)(=O)N1CCC(CSc2nonc2/C(=N/O)Nc2ccc(F)c(Br)c2)C1]

¹H NMR (400 MHz, DMSO-d₆) δ 11.75 (s, 1H), 9.02 (s, 1H), 7.19 (t, J=8.7 Hz, 1H), 7.09 (dd, J=5.9, 2.5 Hz, 1H), 6.78 (s, 2H), 6.74-6.65 (m, 1H), 3.27 (ddd, J=25.3, 15.6, 10.7 Hz, 4H), 3.13 (dd, J=17.1, 7.7 Hz, 1H), 2.93 (dd, J=9.8, 7.3 Hz, 1H), 2.65-2.56 (m, 1H), 2.04 (dd, J=12.0, 4.9 Hz, 1H), 1.67 (dd, J=12.3, 7.9 Hz, 1H). LC/MS (ESI+) calcd for C₂₃H₂₄ClN₃O₂ (M+H⁺) m/z, 496.0; found: 496.0.

Example 25: (Z)—N-(3-Bromo-4-fluorophenyl)-4-(((1-(cyclopropylsulfonyl)azido-3-yl)methyl)amino)-N'-hydroxyl-1, 2, 5-oxadiazol-3-carboxyoximide (Compound 86)

Compound 86 was prepared by the method similar to that of example 1.

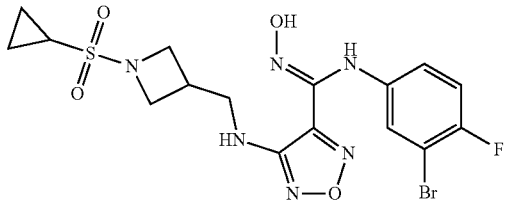 [SMILES: O=S(=O)(C1CC1)N1CC(CNc2nonc2/C(=N/O)Nc2ccc(F)c(Br)c2)C1]

¹H NMR (400 MHz, DMSO-d₆): δ 11.40 (s, 1H), 8.94 (s, 1H), 7.19 (t, J=8.4, 17.2 Hz, 1H), 7.12-7.10 (m, 1H), 6.75-6.71 (m, 1H), 6.47 (t, J=5.6, 11.6 Hz, 1H), 3.93-3.89 (m, 2H), 3.66-3.63 (m, 2H), 3.44-3.38 (m, 2H), 2.86-2.83 (m, 1H), 2.75-2.71 (m, 1H), 1.03-0.99 (m, 1H), 0.92-0.89 (m, 1H). LC/MS (ESI⁺) C₁₆H₁₈BrFN₆O₄S (M+H⁺) m/z, 489.

Example 26: (Z)—N-(3-bromo-4-fluorophenyl)-4-(3-fluoro-1-sulfadiazin-3-yl)methyl)amino)-N'-hydroxyl 1, 2, 5-oxadiazol-3-carboxyoximide (Compound 91)

Compound 91 was prepared by the method similar to that of example 1.

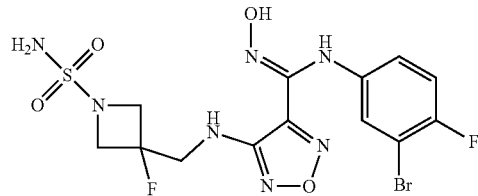 [SMILES: NS(=O)(=O)N1CC(F)(CNc2nonc2/C(=N/O)Nc2ccc(F)c(Br)c2)C1]

¹H NMR (CD₃OD, 400 MHz): δ 7.17-7.15 (m, 1H), 7.09-7.05 (m, 1H), 6.89-6.85 (m, 1H), 3.99-3.95 (m, 4H), 3.85-3.80 (m, 2H). LC/MS (ESI+) m/z, 482 (M+H⁺).

Example 27: (Z)—N-(3-bromo-4-fluorophenyl)-N'-hydroxyl-4-(3-hydroxyl-1-sulfadiazin-3-yl)methyl)amino)-1,2,5-oxadiazol-3-carboxyoxime (Compound 127)

Compound 127 was prepared by the method similar to that of example 1.

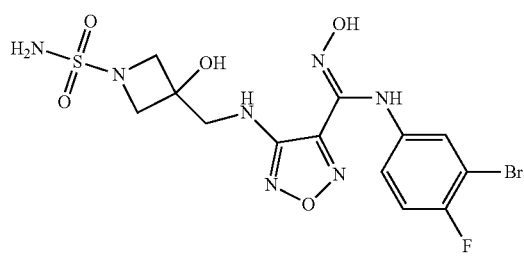 [SMILES: NS(=O)(=O)N1CC(O)(CNc2nonc2/C(=N/O)Nc2ccc(F)c(Br)c2)C1]

$^1$H NMR (DMSO-d$_6$, 400 MHz): δ 11.62 (s, 1H), 8.90 (s, 1H), 7.21-7.12 (m, 2H), 6.98 (s, 2H), 6.82-6.78 (m, 1H), 6.14-6.12 (m, 2H), 3.65-3.59 (m, 4H), 3.52-3.51 (m, 2H). LC/MS (ESI+) m/z, 480 (M+H$^+$).

Example 28: (Z)—N-(3-bromo-4-fluorophenyl)-N'-hydroxyl-4-((2-(1-sulfamoylazetidin-3-yl)ethyl)amino)-1,2,5-oxadiazol-3-formamidine (Compound 132)

Compound 132 was prepared by the method similar to that of example 1.

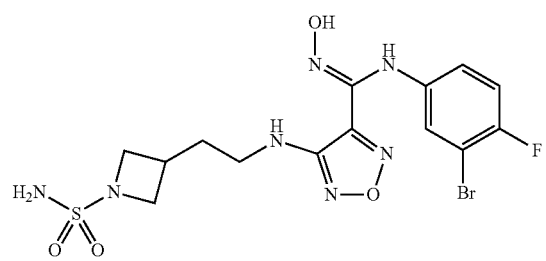 [SMILES: NS(=O)(=O)N1CC(CCNc2nonc2/C(=N/O)Nc2ccc(F)c(Br)c2)C1]

$^1$H NMR (400 MHz, DMSO-d$_6$) δ 11.45 (s, 1H), 8.93 (s, 1H), 7.20 (t, J=8.8 Hz, 1H), 7.12 (dd, J=6.0, 2.7 Hz, 1H), 6.78 (s, 1H), 6.22 (s, 1H), 3.75 (t, J=8.0 Hz, 2H), 3.60 (d, J=6.6 Hz, 1H), 3.42-3.38 (m, 2H), 3.18 (d, J=6.4 Hz, 2H), 1.82 (d, J=7.0 Hz, 2H), 1.77 (dd, J=6.8, 3.3 Hz, 2H). LC/MS (ESI+) m/z, 478 (M+H$^+$).

Example 29: (Z)—N-(3-bromo-4-fluorophenyl)-N'-hydroxyl-4-(((1-carbamoylazetidin)-3-methyl)amino)-1,2,5-oxadiazol-3-formamidine (Compound 140)

Compound 140 was prepared by the method similar to that of example 1.

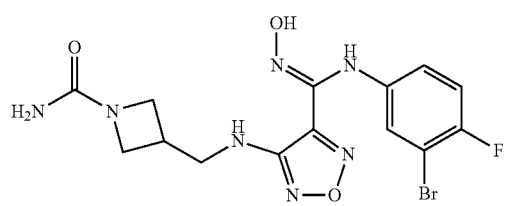 [SMILES: NC(=O)N1CC(CNc2nonc2/C(=N/O)Nc2ccc(F)c(Br)c2)C1]

$^1$H NMR (400 MHz, DMSO-d$_6$) δ 11.54 (s, 1H), 9.00 (s, 1H), 7.27 (t, J=8.8 Hz, 1H), 7.19 (dd, J=6.1, 2.7 Hz, 1H), 6.84 (m, 1H), 6.46 (d, J=5.9 Hz, 1H), 5.90 (s, 2H), 3.89 (t, J=8.1 Hz, 2H), 3.57 (dd, J=8.1, 5.2 Hz, 2H), 3.47 (dd, J=12.3, 5.8 Hz, 2H), 2.84 (m, 1H). LC/MS (ESI+) calcd for C$_{14}$H$_{15}$BrFN$_7$O$_3$ ([M+H]$^+$) m/z 428.0; found 428.0.

Example 30: (Z)—N-(3-Bromo-4-fluorophenyl)-N'-hydroxyl-4-(((1-carbamoylazetidin)-3-methyl)thiol)-1,2,5-oxadiazol-3-formamidine (Compound 148)

Compound 148 was prepared by the method similar to that of example 1.

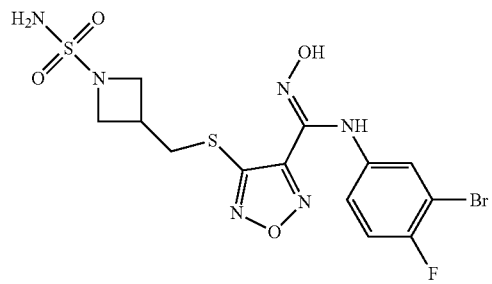 [SMILES: NS(=O)(=O)N1CC(CSc2nonc2/C(=N/O)Nc2ccc(F)c(Br)c2)C1]

$^1$H NMR (400 MHz, DMSO-d$_6$) δ 11.76 (s, 1H), 8.99 (s, 1H), 7.17 (t, J=8.8 Hz, 1H), 7.07 (dd, J=6.0, 2.4 Hz, 1H), 6.92 (s, 2H), 6.71 (m, 1H), 3.82 (t, J=8.0 Hz, 2H), 3.52 (m, 2H), 3.40 (d, J=7.2 Hz, 1H), 2.87 (m, 1H). LC/MS (ESI+) calcd for C$_{13}$H$_{14}$BrFN$_6$O$_4$S$_2$ ([M+H]$^+$) m/z 481.0; found 481.0.

Example 31: (Z)—N-(3-bromo-4-fluorophenyl)-N'-hydroxyl-4-((2-(1-sulfamoylazetidin-3-yl)ethyl)thio)-1,2,5-oxadiazol-3-formamidine (Compound 149)

Compound 149 was prepared by the method similar to that of example 1.

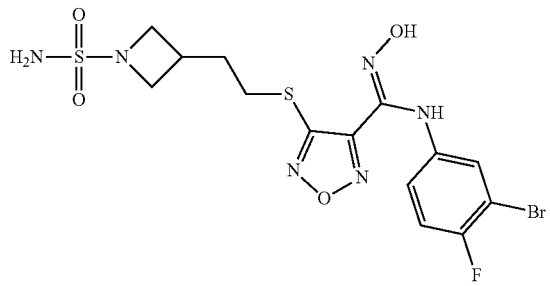 [SMILES: NS(=O)(=O)N1CC(CCSc2nonc2/C(=N/O)Nc2ccc(F)c(Br)c2)C1]

$^1$H NMR (400 MHz, DMSO-d$_6$) δ 11.72 (s, 1H), 9.01 (s, 1H), 7.19 (t, J=8.8 Hz, 1H), 7.07 (dd, J=6.0, 2.7 Hz, 1H), 6.88 (s, 2H), 6.71-6.67 (m, 1H), 6.52 (s, 1H), 3.76 (t, J=8.0 Hz, 2H), 3.45-3.40 (m, 2H), 3.13 (t, J=7.2 Hz, 2H), 1.98 (d, J=7.1 Hz, 2H). LC/MS (ESI+) Calcd for C$_{14}$H$_{16}$BrFN$_6$O$_4$S$_2$ (M+H$^+$) m/z, 496.0; Found, 497.0.

Example 32: (Z)—N-(3-bromo-4-fluorophenyl)-N'-hydroxyl-4-(((1-sulfadiazin-3-yl)methyl-D2)amino)-1,2,5-oxadiazol-3-carboxyoximide (Compound 150)

Compound 150 was prepared by the method similar to that of example 1.

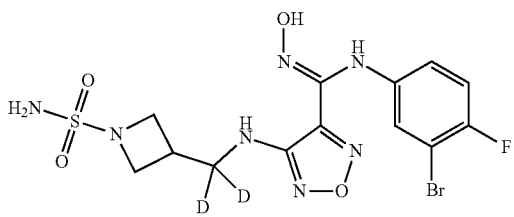 [SMILES: [2H]C([2H])(Nc1nonc1/C(=N/O)Nc1ccc(F)c(Br)c1)C1CN(S(N)(=O)=O)C1]

$^1$H NMR (CD$_3$OD, 400 MHz): δ 7.03-7.01 (m, 1H), 6.97-6.93 (m, 1H), 6.76-6.72 (m, 1H), 3.80-3.76 (m, 2H), 3.51-3.48 (m, 2H), 2.78-2.75 (m, 1H). LC/MS (ESI+) m/z, 466 (M+H$^+$).

The beneficial effect of the present invention is elucidated by the following experimental examples: The use of the present invention will be further described by the following biological experimental examples, but that does not mean to limit the application scope of the present invention.

Experimental Example 1: Determination of the Inhibitory Activity of the Compound According to the Present Invention Against Human IDO1 Protease 1) Experimental Materials and Apparatus:
IDO1 (His-tag) enzyme (BPS Bioscience)
L-tryptophan (Sigma)
Methylene blue (Sigma)
Catalase originated from the liver of cattle (Sigma)
L-ascorbic acid (Sigma)
Glycerol (Sigma)
Potassium dihydrogen phosphate solution (Sigma)
Tween 20 (Sigma)
Automatic sampling platform Liquid handler (Bravo & Echo)
Microplate Reader SpectraMax M5e (Molecular Devices)
2) Test Method of Compounds: The Compounds are Determined by Absorbance Test Method:

The tested compounds and the reference compounds are dissolved in DMSO to prepare a high concentration of storage solution. The stock solution of reference compound was diluted with DMSO to prepare a 100× solution. In the first column of the working plate, 8 µL above tested compounds and 8 µL 100× reference compound were respectively added as the highest concentration, and then the highest concentrations were subjected to three times dilution to obtain 11 concentrations and prepare 100× solution. 0.5 µL solution was transferred from the above plate to the detection plate. To each well was added 0.5 µL 100× compound solution. For HPE and ZPE control wells, 0.5 µL 100% DMSO was added.

25 µL 2×IDO1 (His-tag) enzyme solution (containing L-ascorbic acid, methylene blue, and catalase) was added to each well. 25 µL reaction solution without IDO1 (His-tag) enzyme was added into HPE control well. The test plate was centrifugated at 1000 rpm for 1 minute to mix well. Then, the test plate was incubated at room temperature for 30 minutes. 25 µL above 2× substrate (L-tryptophan) solution was added to each well. The test plate was centrifugated at 1000 rpm for 1 minute to mix well. The detection plate was placed on ELISA (SpectraMax M5e), the temperature was set at 25° C., and the absorbance (OD value) was measured at 320 nm every 10 minutes till 60 minutes.

Calculating the increase ratio of absorbance: the slope of the absorbance increase curve from 10 min to 60 min is derived from SpectralMax M5e. The inhibition coefficient of compound was calculated: the inhibition ratio of compound=(the absorbance increase ratio of ZPE control well−the absorbance increase ratio of compound well)/(the absorbance increase ratio of ZPE control well−the absorbance increase ratio of HPE control well)×100. Results was analyzed by Prism 5.0.

3) Results: IC$_{50}$ Values of the Compounds According to the Present Invention Against the Activity of Human IDO1 Protease are Shown in Table 1.

TABLE 1

| The inhibitory activity of compounds against human IDO1 protease. | |
|---|---|
| Compound No. | IC$_{50}$ (nM) |
| 2 | 182 |
| 3 | 430 |
| 4 | 55 |
| 5 | 276 |
| 6 | 88 |
| 7 | 59 |
| 8 | 112 |
| 9 | 84 |
| 10 | 254 |
| 11 | 206 |
| 12 | 133 |
| 13 | 214 |
| 14 | 279 |
| 16 | 151 |
| 18 | 114 |
| 19 | 119 |
| 20 | 79 |
| 21 | 141 |
| 23 | 183 |
| 24 | 69 |
| 25 | 96 |
| 26 | 340 |
| 27 | 628 |
| 28 | 107 |
| 29 | 173 |
| 78 | 69 |
| 81 | 142 |
| 85 | 115 |
| 86 | 167 |
| 89 | 183 |
| 91 | 128 |
| 92 | 64 |
| 150 | 81 |
| 151 | 101 |

Conclusion: the compound of the present invention has obvious inhibitory effect on the activity of human IDO1 protease.

Experimental Example 2: Determination of Inhibition of Compounds According to the Present Invention on IDO Protease in HeLa Cells 1) Experimental Materials and Apparatus
HeLa cells (ATCC, Cat. No. CCL-2)
γ interferon IFNγ (R&D, Cat. No. 285-IF-100)
DMEM High Glucose media (Invitrogen, Cat. No. 11965-084)
Fetal bovine serum FBS (Invitrogen, Cat. No. 10100-147)
Trypsin-EDTA (0.050%)(Invitrogen, Cat. No. 25300-054)

Phosphate buffer solution PBS, pH 7.4 (Invitrogen, Cat. No. 10010023)
Penicillin-Streptomycin (P/S) (Invitrogen, Cat. No. 15070063)
L-tryptophan (Trp) (Sigma, Cat. No. T8941)
L-kynurenine (Kyn) (Sigma, Cat. No. K8625)
N'-diformylkynurenine (NFK) (J&K, Cat. No. F700490)
3-Nitro-L-tyrosine (J&K, Cat. No. N0905)
Acetonitrile (Sigma, Cat. No. 34851)
Dimethylsulfoxide DMSO (Sigma, Cat. No. D8418)
Inhibitor INCB024360 (Selleckchem, Cat. No. S7910)
Inhibitor INCB024360-analog (MedKoo, Cat. No. 205493)
Inhibitor NLG919 (Selleckchem, Cat. No. S7111)
96 well transparent flat bottom polystyrene cell culture plate (Corning, Cat #3599)
96 well V-bottom polypropylene plate (PE, Cat #6008290)
96 well U-shaped bottom polypropylene plate (PE, Cat. No. 6008390)
Multidrop™ distribution box with small metal tip (Thermo, Cat. No. 24073295)
Multidrop™ distribution box of standard tube with metal tip (Thermo, Cat. No. 24072670)
Automatic filling platform (Agilent)
Multidrop™ Combi automatic liquid separator (Thermo)
Centrifugal machine (Eppendorf)
Cell incubator (Thermo)
Cell counter (Thermo)
RapidFire Mass system (Agilent)

2) Experimental Method for Compound Assay

The compound (compounds 4, 8, 9, 78, 91 of the present invention) was dissolved in DMSO to prepare a solution with a concentration of 3 mM, and then 15 μL of the compound solution is added to a 96 well plate, and serially diluted by 3 times dilution to obtain 10 points. 2 μL compound solution or DMSO (for HPE/ZPE) was transferred to a new 96 well plate. HeLa cell suspension was seeded into the cell culture plate with a density of $1\times10^4$ cells/well. For HPE control well, the cell culture medium for detection was DMEM, including 10% FBS, 1% P/S, and 122 μM Trp; for ZPE control well and the compound wells, the cell culture medium was DMEM, including 10% FBS, 1% P/S, 122 M Trp, and 25 ng/ml IFNγ. 192 μL detection medium prepared as above was added to a 96 well plate. 78 μL DMEM was added to the compound plate and thoroughly mixed, and then 8 μL compound solution diluted with DMEM was transferred to the 96 well plate containing the detection medium. The cell culture plate was taken out, and the cell culture medium was discarded, then 100 μL compound solution mentioned above was transferred to the cell culture plate. The cell culture plate was moved into the cell incubator and kept for 48 hours. When detected, the cell culture plate was taken out, and 50 μL supernatant was transferred to a new 96 well plate, to which was added 200 μL acetonitrile, and the plate was mixed well. The plate was centrifugated at 4° C. for 20 minutes (rotatory speed being 4000 rpm), and 40 μL supernatant was transferred to another 96 well plate, to which was further added 360 μL deionized water containing 2 g/mL internal reference (3-nitro-L-tyrosine). The plate was fully mixed, and then the sample was detected by RapidFire/MS system. The standards of L-tryptophan (Trp) and L-kynurenine (Kyn) were dissolved in water to obtain a concentration of 10 mM, and the standard curve was performed by three times dilution. The inhibitory ratio was calculated by obtained data, and the $IC_{50}$ curve was completed by processing the resultant data with Graphpad Prism5 software.

3) Results

The inhibitory activities of the compounds according to the present invention against IDO protease in HeLa cells were determined by above tests, and the $IC_{50}$ values measured is shown in Table 2

TABLE 2

The inhibitory activities of the compounds according to the present invention against IDO protease in HeLa cells.

| Compound No. | $IC_{50}$ (nM) |
|---|---|
| 4 | 5 |
| 8 | 17 |
| 9 | 15 |
| 78 | 13 |
| 91 | 74 |
| 132 | 10 |
| 140 | 75 |
| 148 | 14 |
| 149 | 18 |
| 150 | 9 |

The results showed that the compounds of the present invention have significant inhibitory activities on IDO protease in HeLa cells, in which the inhibitory activities of compounds 4 and 91 are excellent and can treat cervical cancer.

Experimental Example 3: Pharmacokinetics of Compounds of the Present Invention in Mice 1) Experimental Materials and Apparatus:

LC-20AD HPLC system (SHIMADZU, Japan)
API4000 Triple quadrupole mass spectrometer (Applied Biosystem, USA)
PhenixWinnolin Pharmacokinetic software (Version 6.3, Certara, USA)
High speed freezing centrifuge (Thermo Fisher Scientific)
Analytical balance (SECURA225D-1CN)
Experimental animals: ICR mice (Chengdu Dashuo Experimental Animal Co., Ltd)
DMA (Sigma)
CMC-Na (Chengdu Kelong Chemical Co., Ltd)
Heparin (Chengdu Kelong Chemical Co., Ltd)

2) Experimental Methods and Results 5 mg compound was accurately weighed (compound 4 of the present invention, and INCB-24360, a reference compound in clinical phase III), and the corresponding solvent was added to the final volume 10 mL, then mixed with aid of ultrasonic vortex. A solution at concentration of 0.5 mg/mL was prepared. 0.2 ml of the final solution prepared was taken out and stored at −20° C. for concentration determination. Nine healthy adult ICR mice (20-30 g) were fasted overnight (free drinking water) and then administrated at a dosage of 0.2 mL/10 g by gavage. Prior to administration and 0.5, 1, 2, 4, 6, 8, 12, 24 h after administration, 0.1 mL blood was collected from the posterior orbital venous plexus and centrifuged at 4° C. for 5 min to separate the plasma, which was preserved at −20° C. for testing. Then the concentrations of tested compounds in the plasma were determined by LC/MS/MS.

TABLE 3

Pharmacokinetic parameters of the compound of the present invention

| | Pharmacokinetic experiments in mice (PO, 10 mpk) | | | | |
|---|---|---|---|---|---|
| Compound | Peak time $t_{max}$ (h) | Blood concentration $C_{max}$ (ng/mL) | Curve area AUC (ng*h/mL) | Half time $t_{1/2}$ (h) | Retention time $MRT_{inf}$ (h) |
| INCB24360 | 0.5 | 992 | 1808 | 1.4 | 2.03 |
| 4 | 0.5 | 1085 | 1764 | 5.06 | 3.28 |

PK of compound 4 and the reference compound incb-24360 in clinical phase III have been compared in mice. Comparing with the reference compound, the compound of the present invention has a longer half-life time and obvious improvement in pharmacokinetics, with significant difference.

The compounds of the present invention show excellent inhibitory activity against IDO enzyme and cells, as well as good pharmacokinetics, and thus has great application potential in the field of cancer treatment related to IDO inhibition.

The invention claimed is:

1. A compound, an optical isomer thereof, a cis- or trans-isomer thereof, a solvate thereof, a pharmaceutically acceptable salt thereof, a prodrug thereof, a tautomer thereof, a mesomer thereof, a racemate thereof, an enantiomer thereof, a diastereoisomer thereof, or a mixture thereof, wherein the compound is selected from:

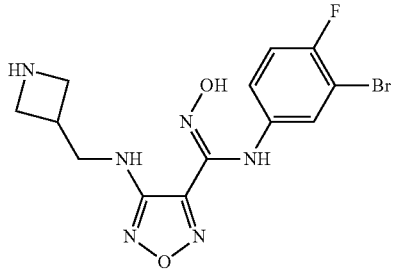

2

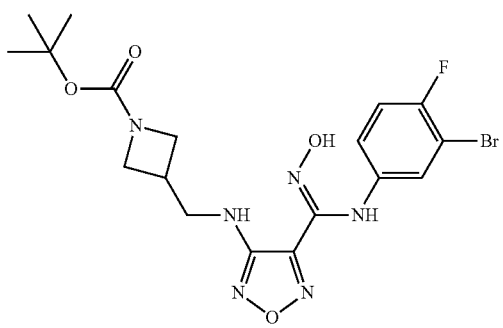

3

-continued

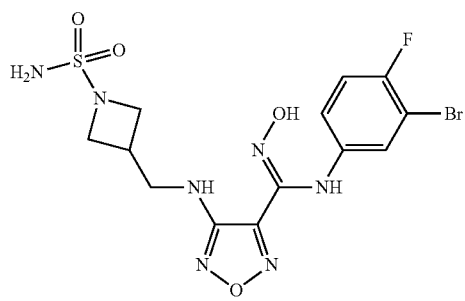

4

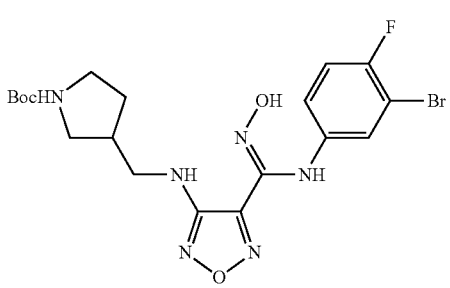

5

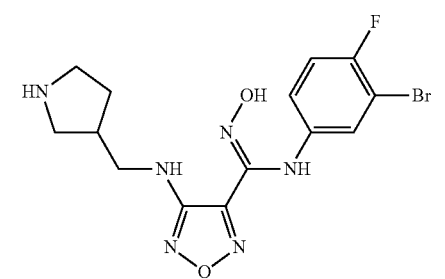

6

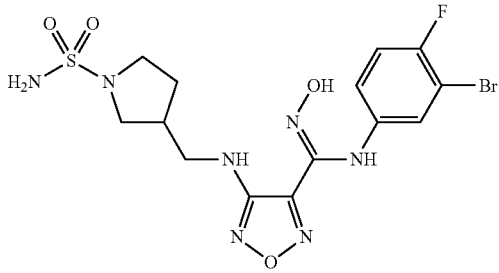

7

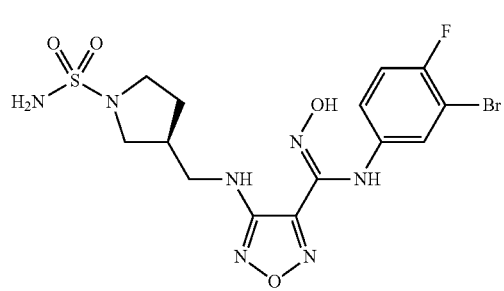
8
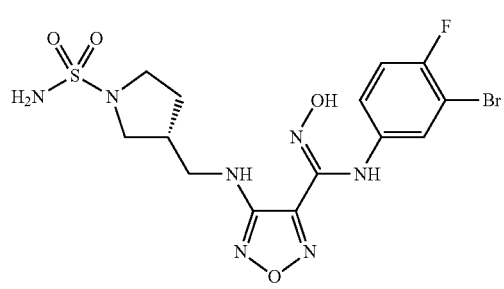
9
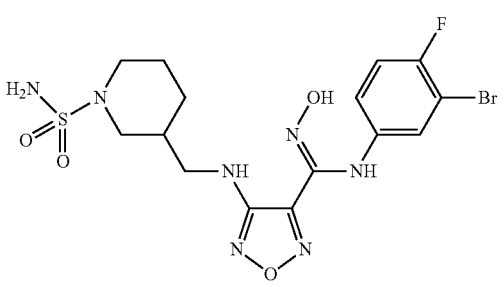
10
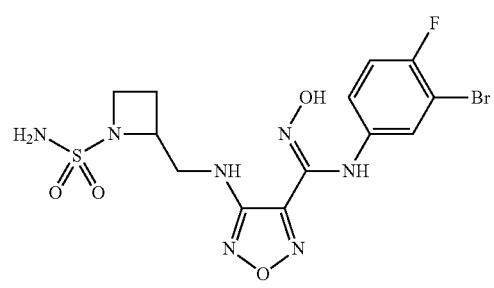
12
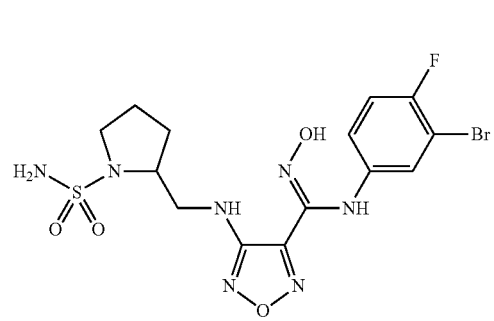
13
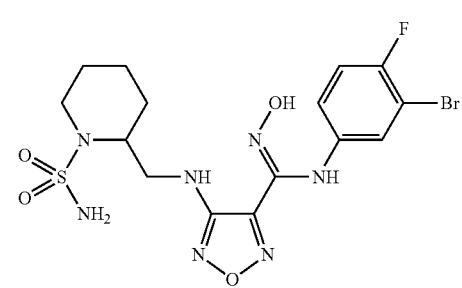
14
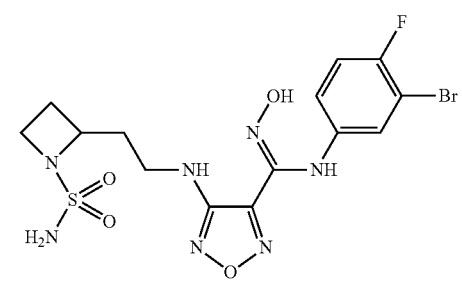
15
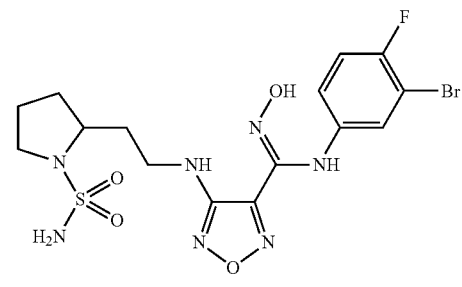
16
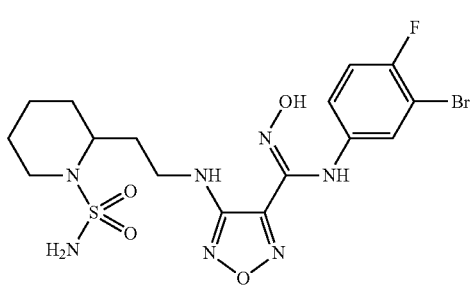
17
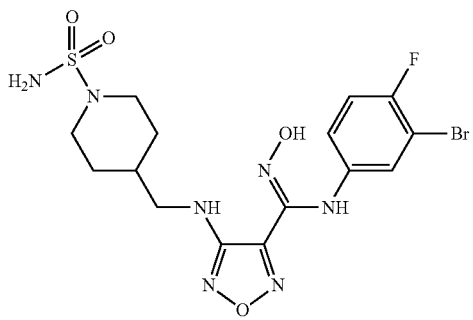
18

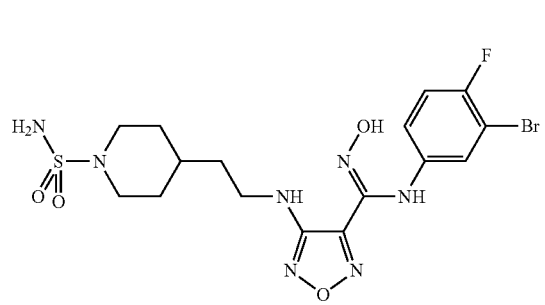
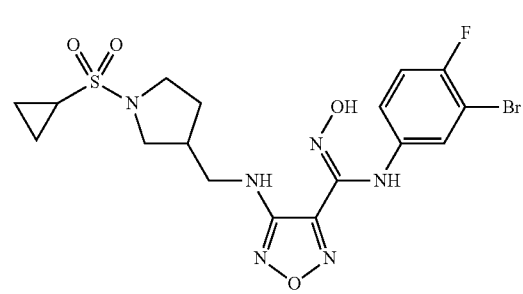
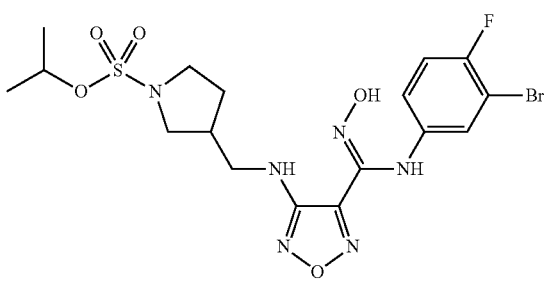
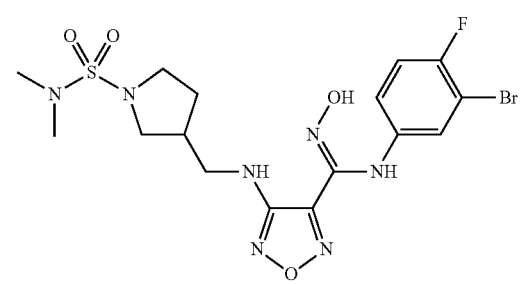
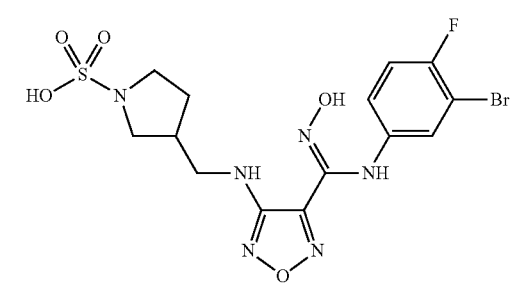
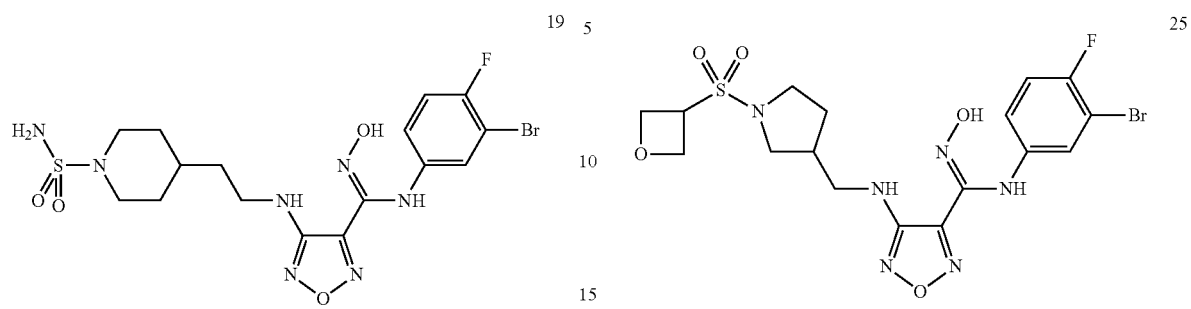
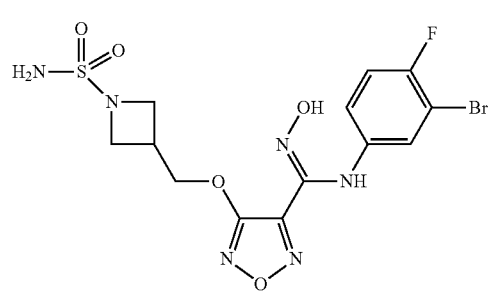
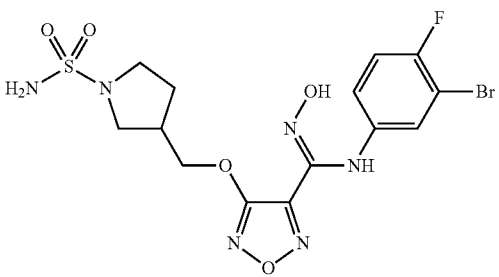
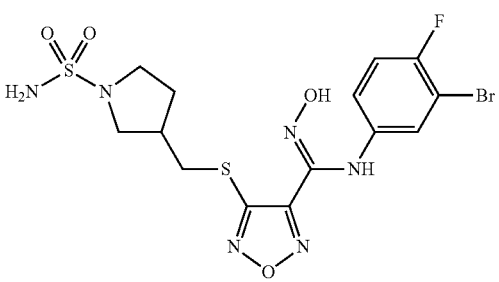
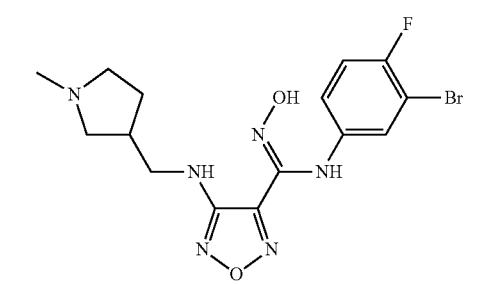

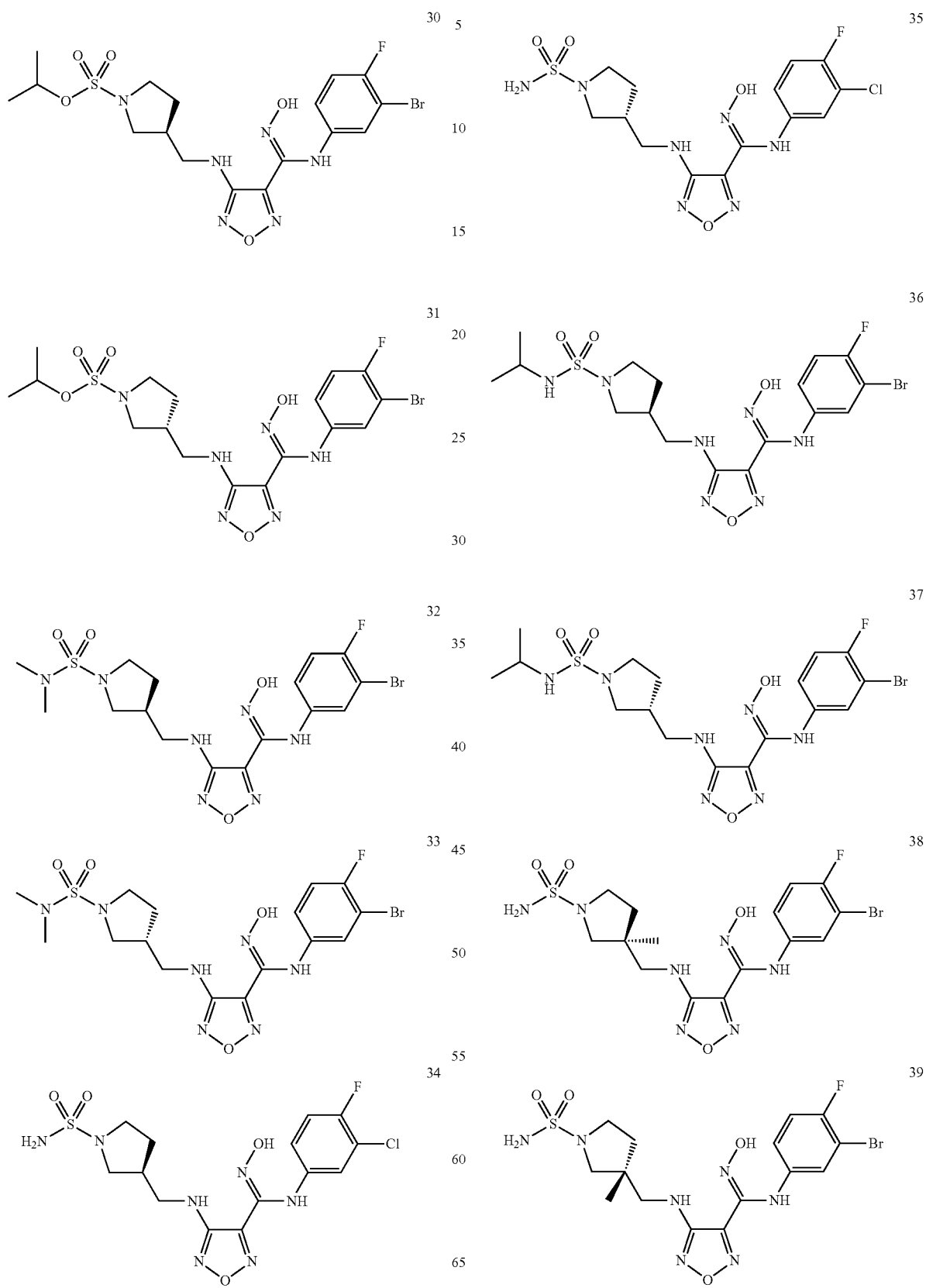

| 65 -continued | 66 -continued |
|---|---|
| 40 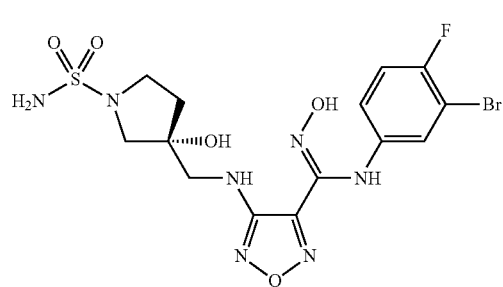 | 45 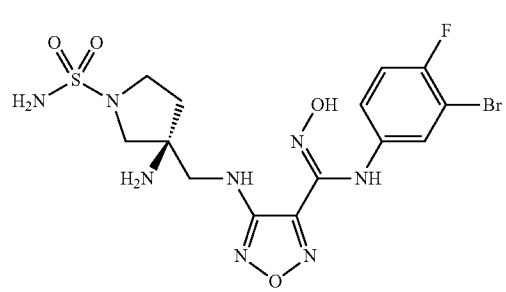 |
| 41 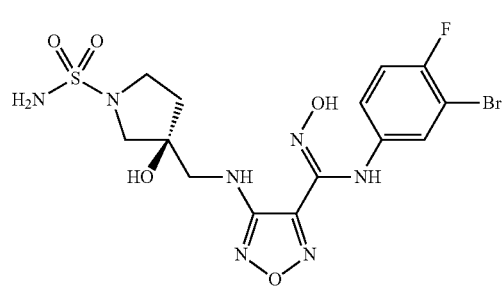 | 46 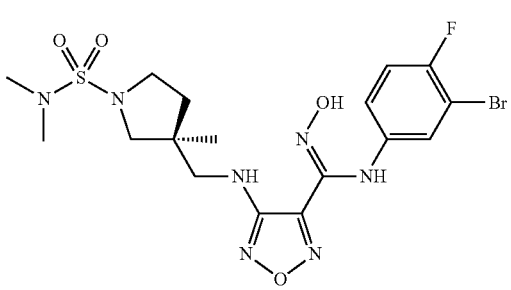 |
| 42 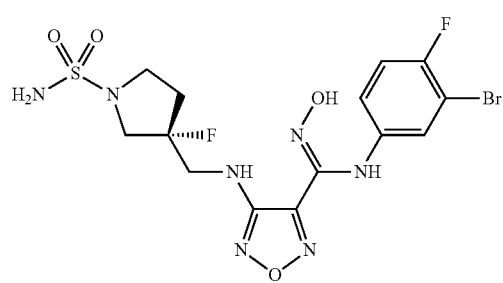 | 47 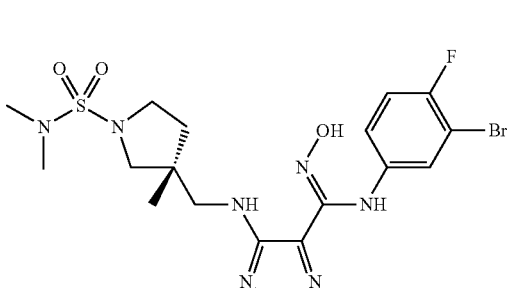 |
| 43 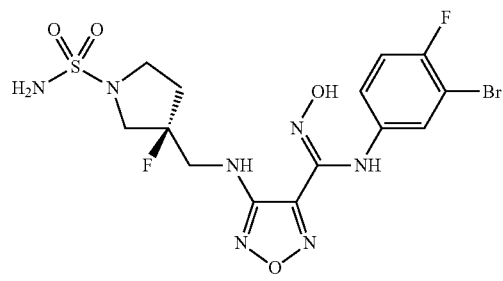 | 48 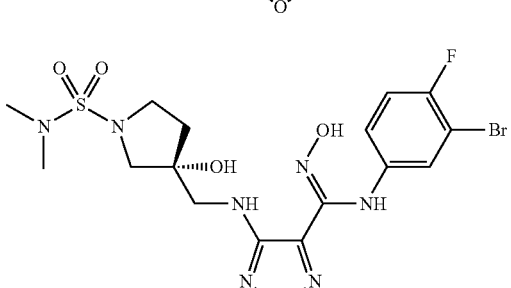 |
| 44 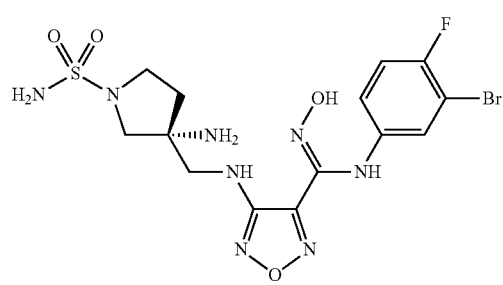 | 49 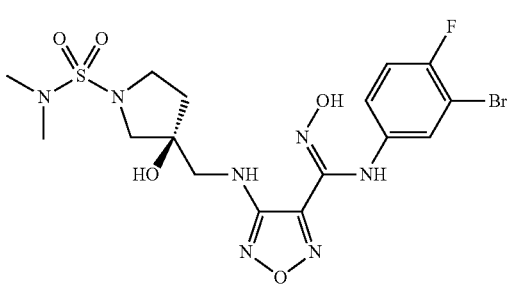 |

50
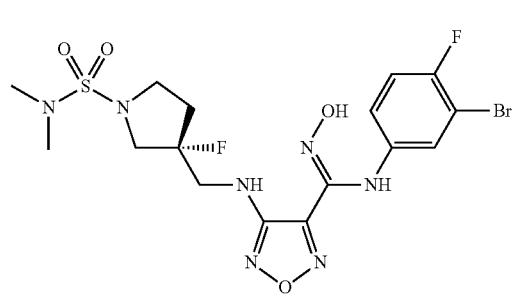
51
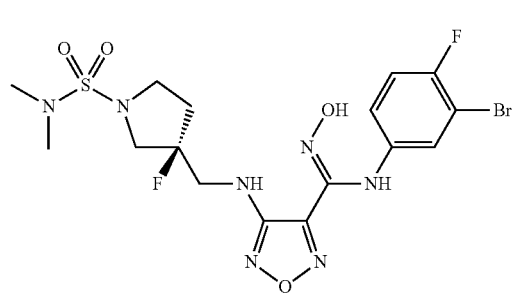
52
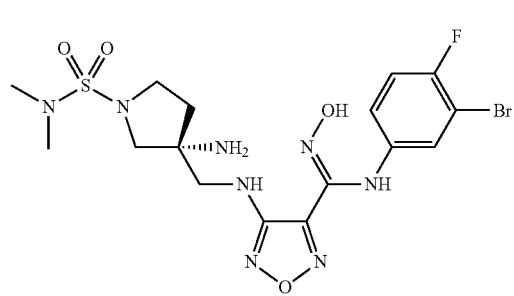
53
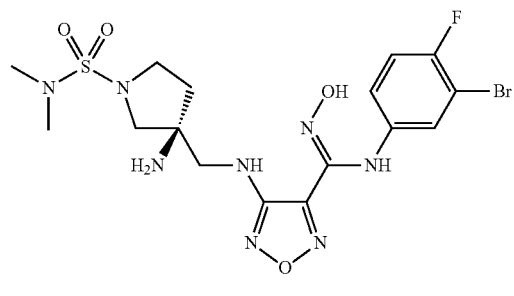
54
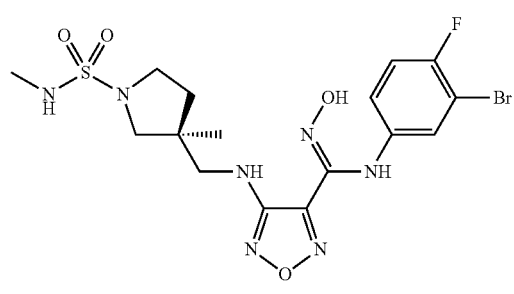
55
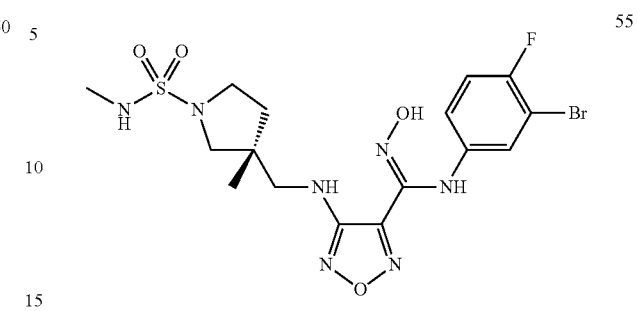
56
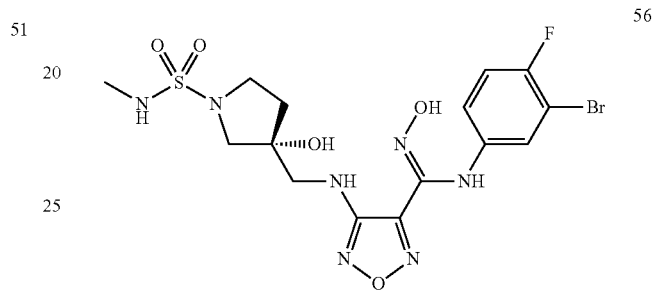
57
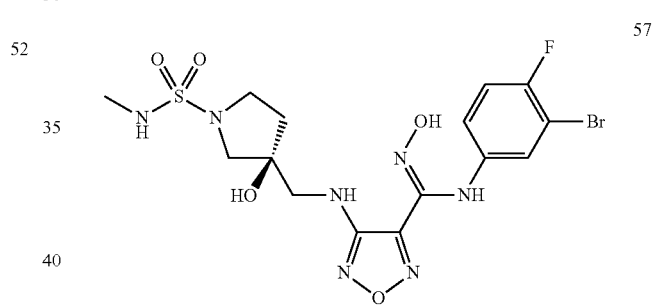
58
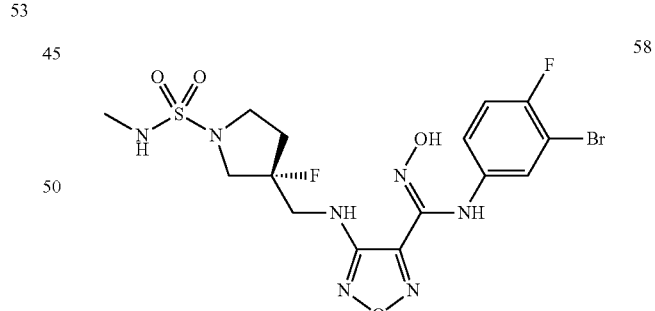
59
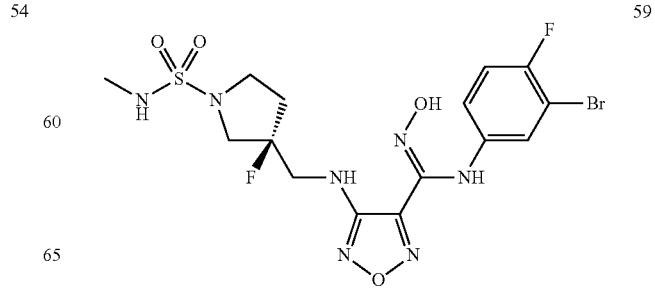

60
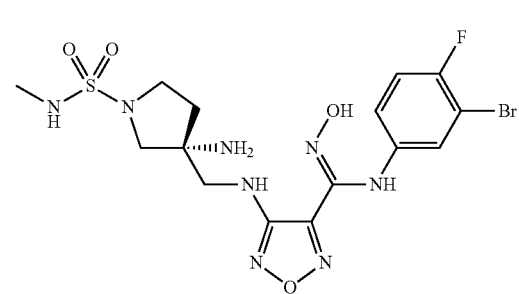
61
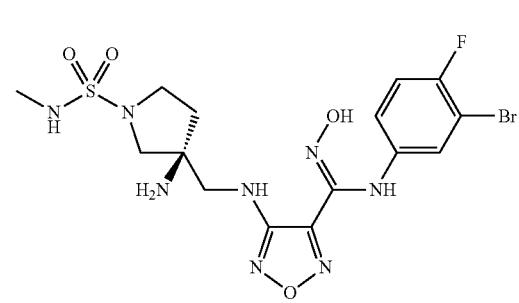
62
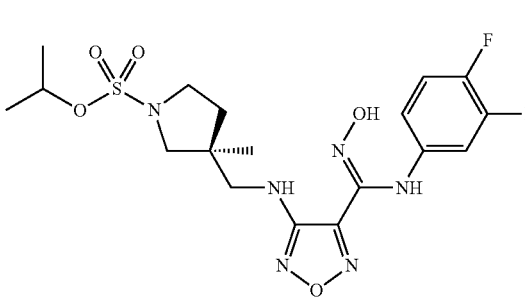
63
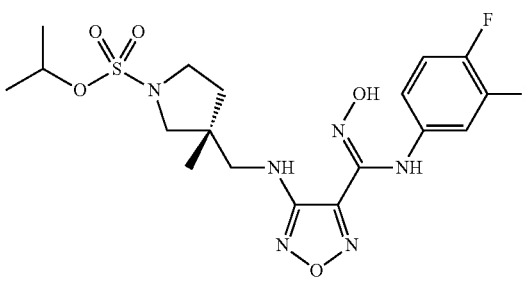
64
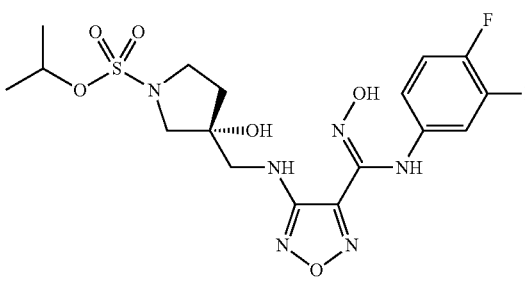
65
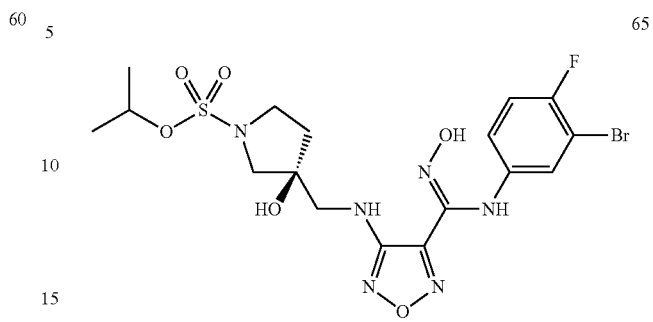
66
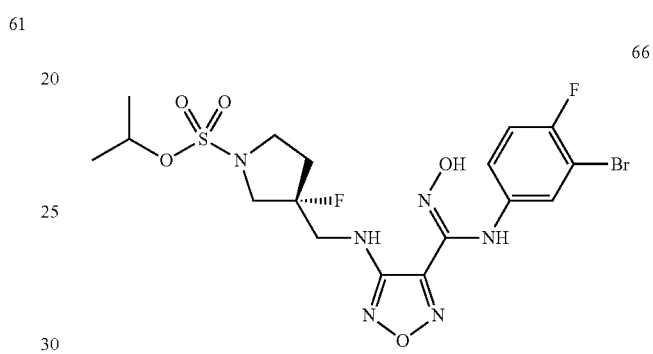
67
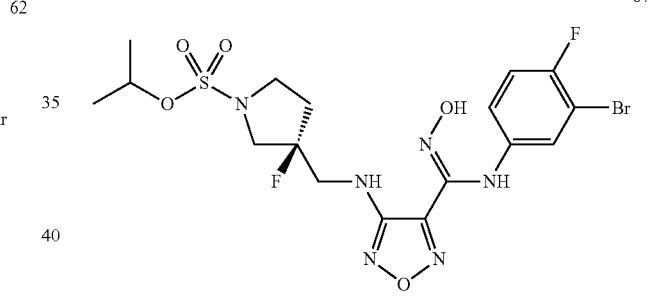
68
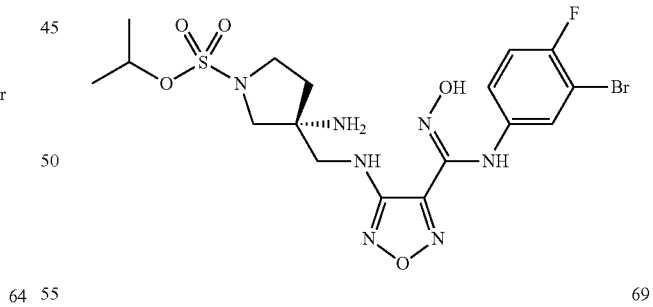
69
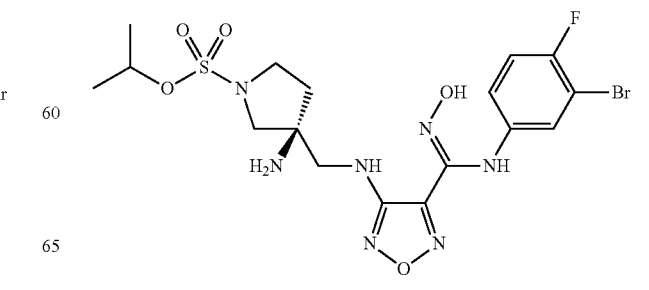

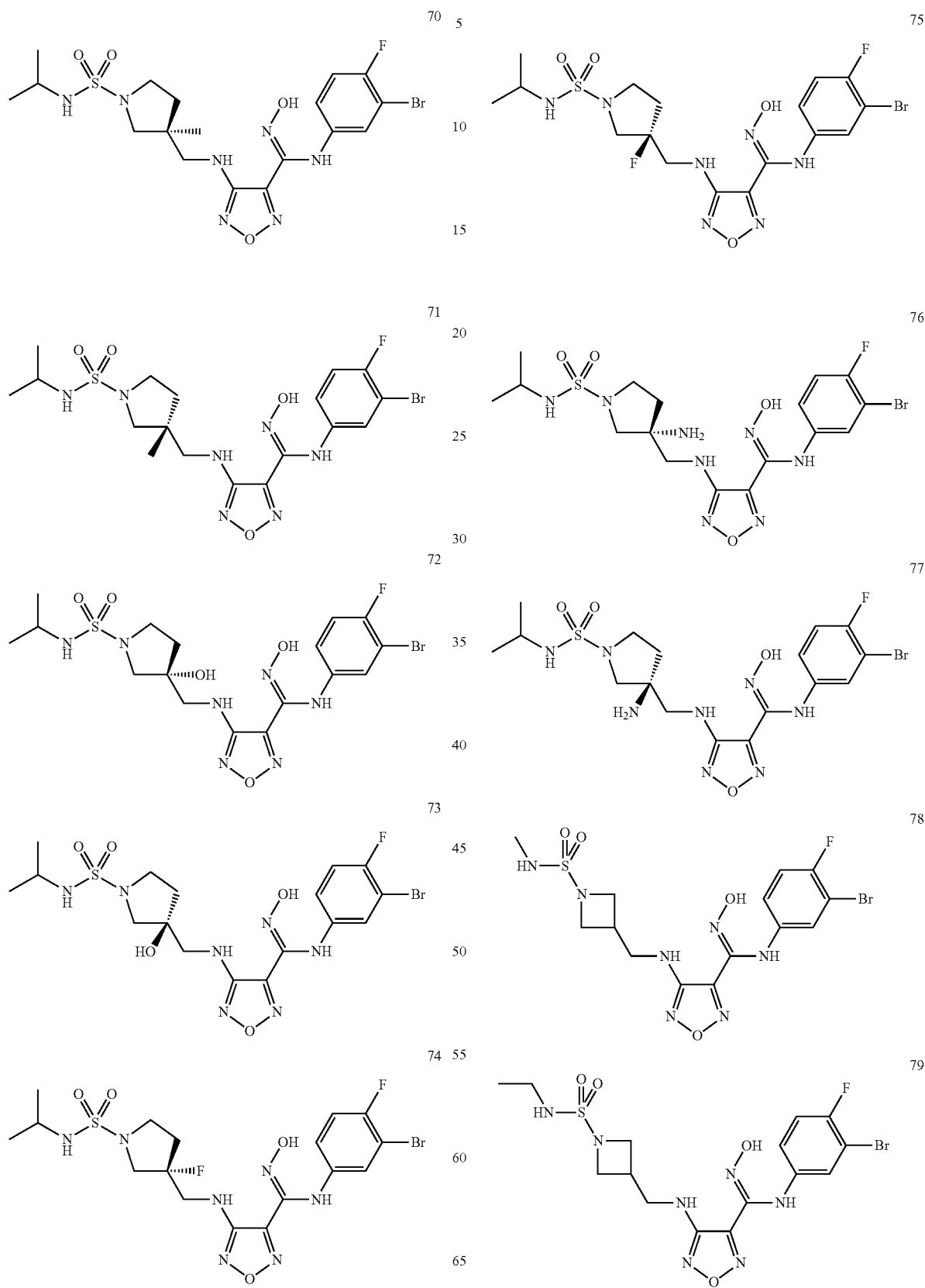

80
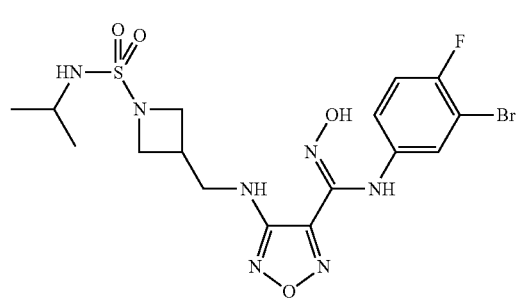
81
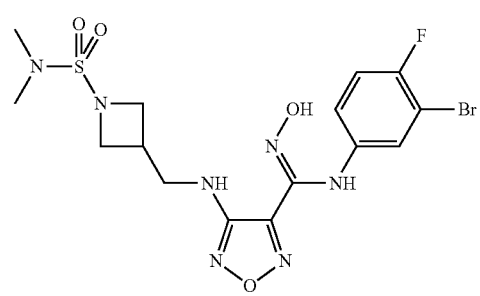
82
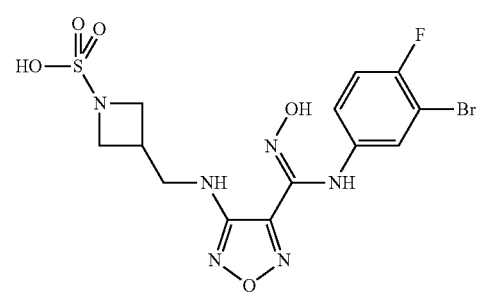
83
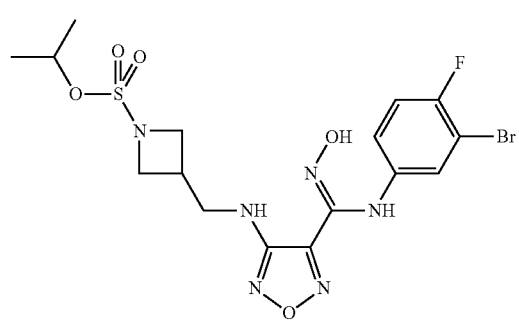
84
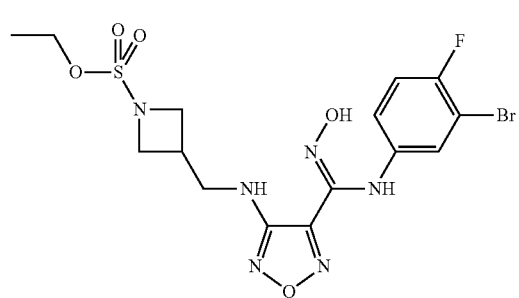
86
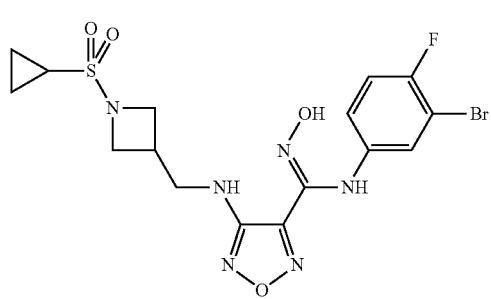
87
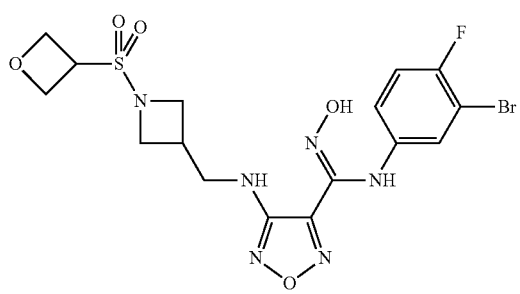
88
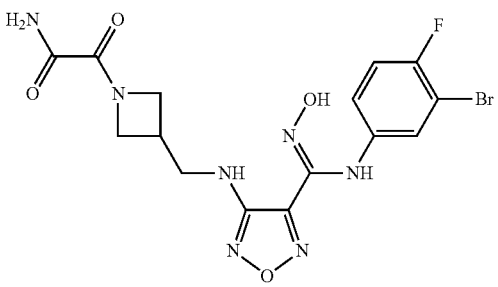
89
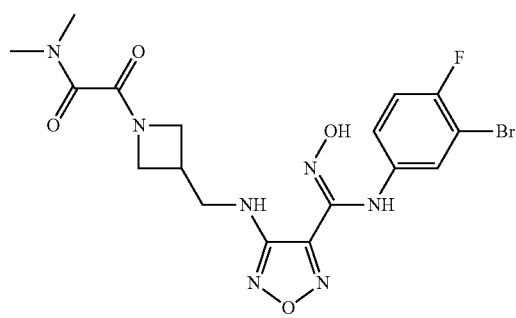
90
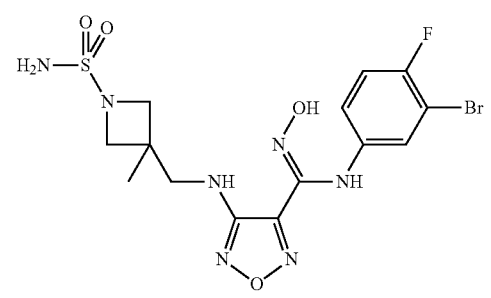

91 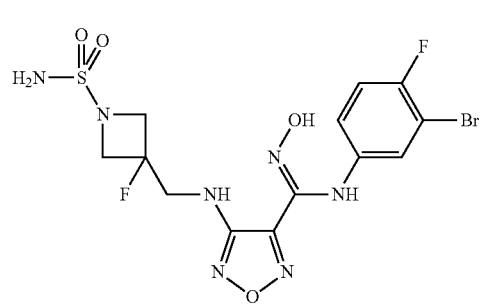
92 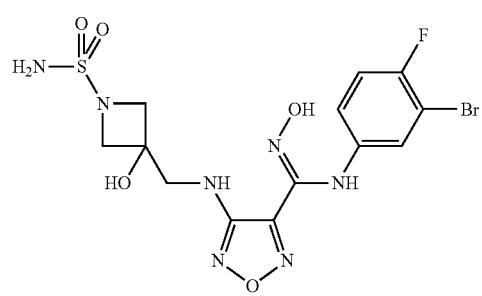
93 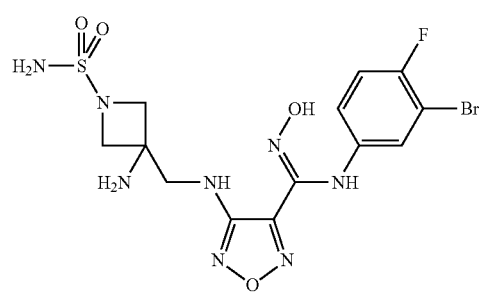
94 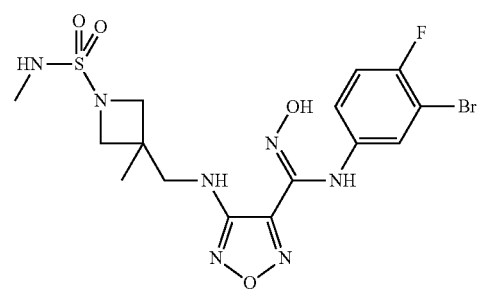
95 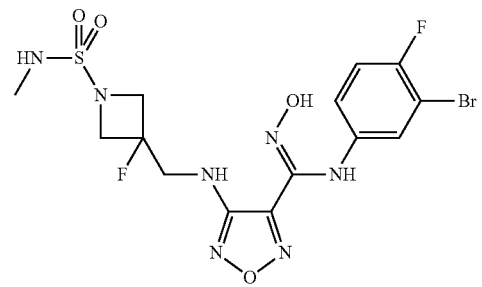
96 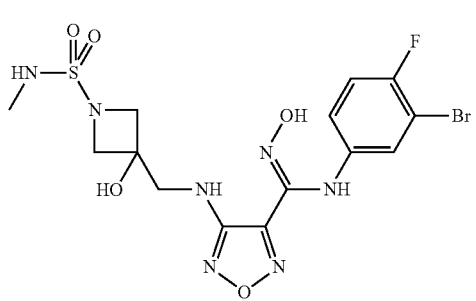
97 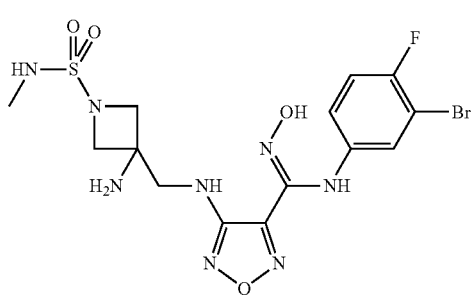
98 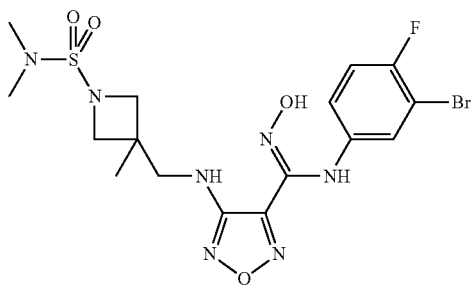
99 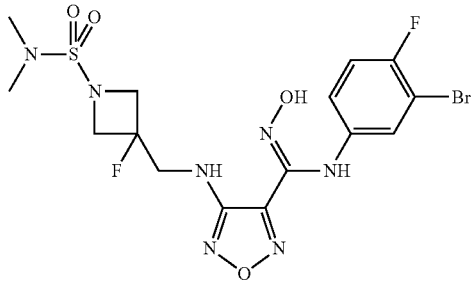
100 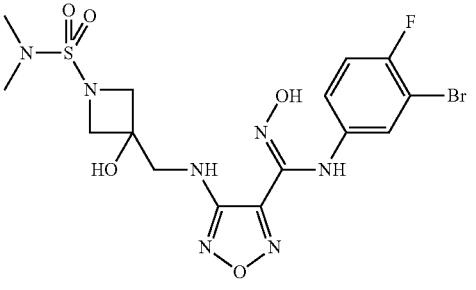

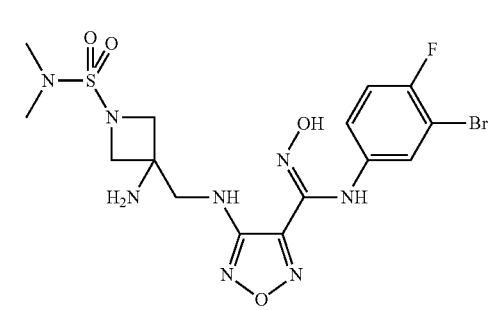
101
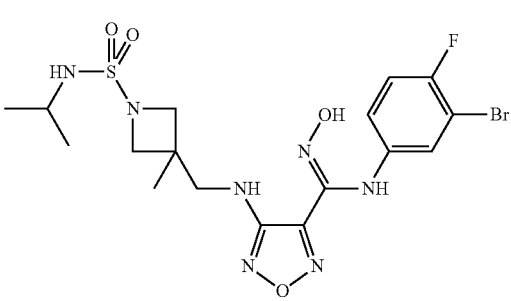
102
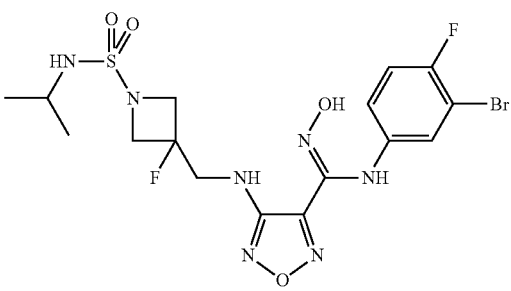
103
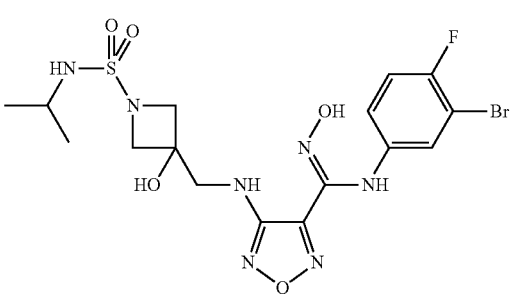
104
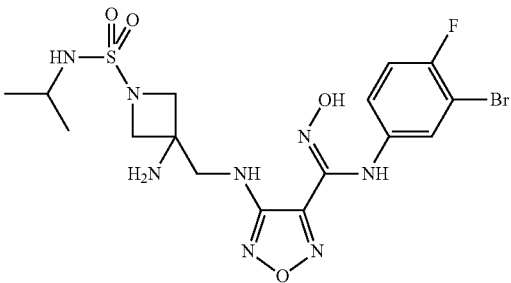
105
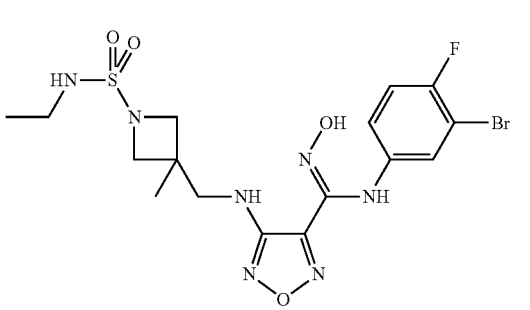
106
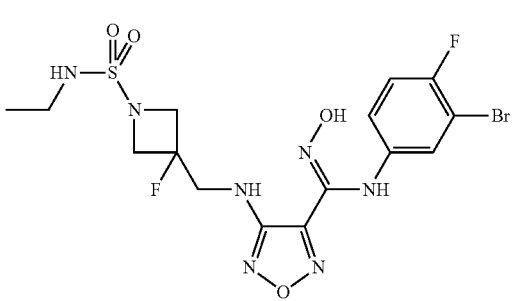
107
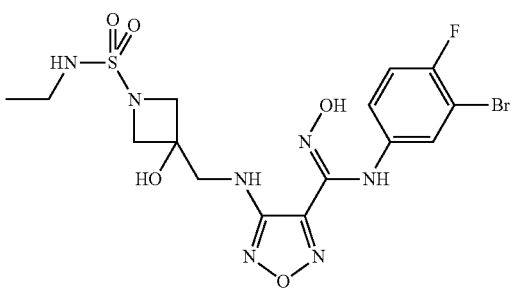
108
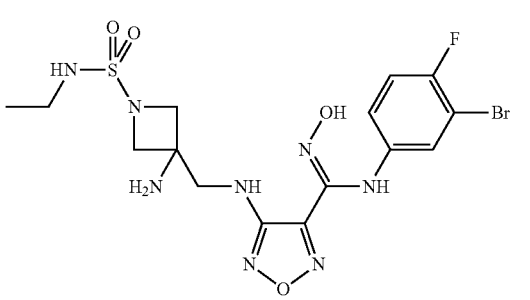
109
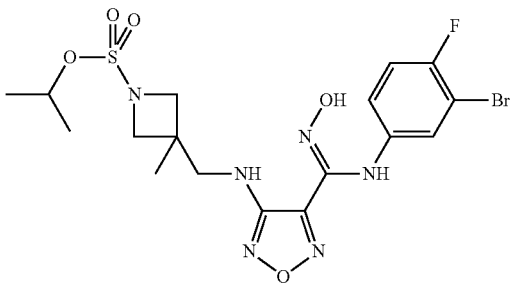
110

111 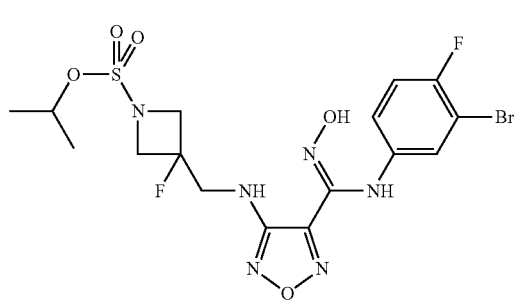
112 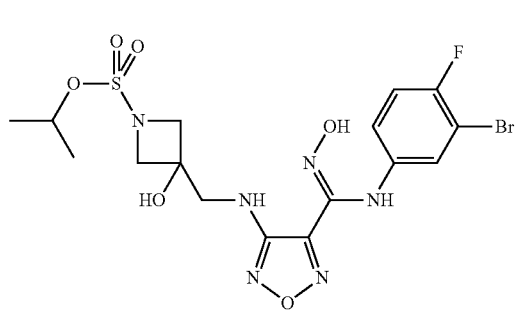
113 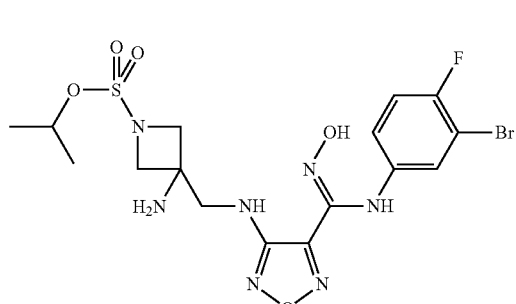
114 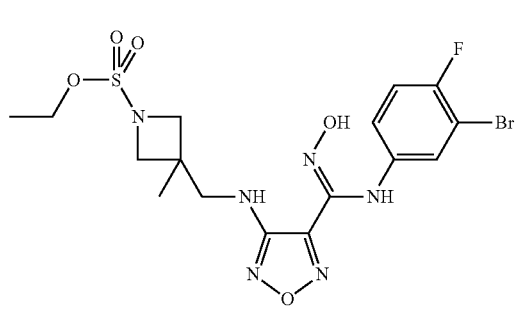
115 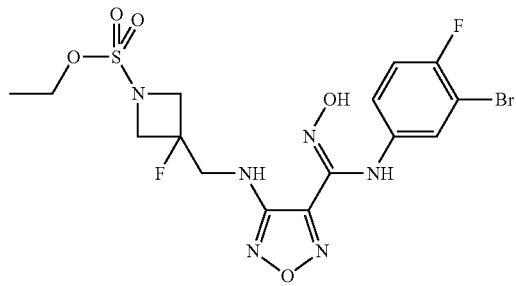
116 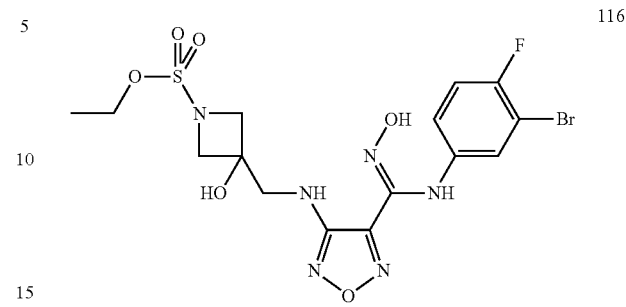
117 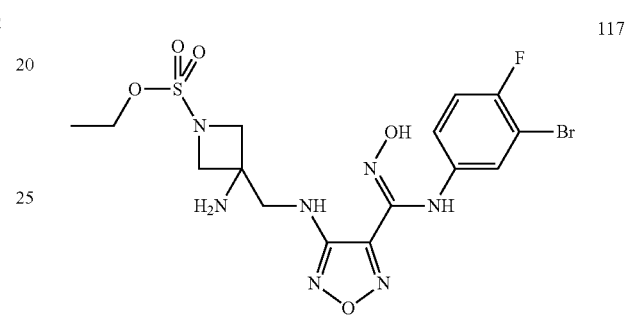
118 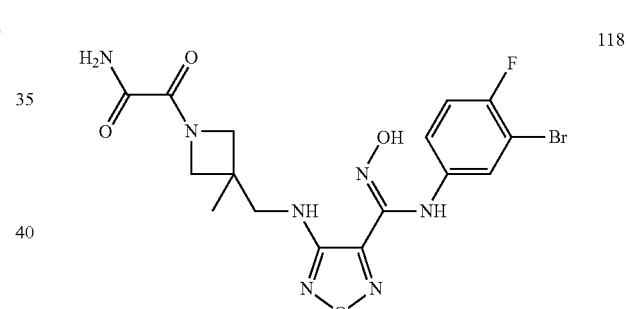
119 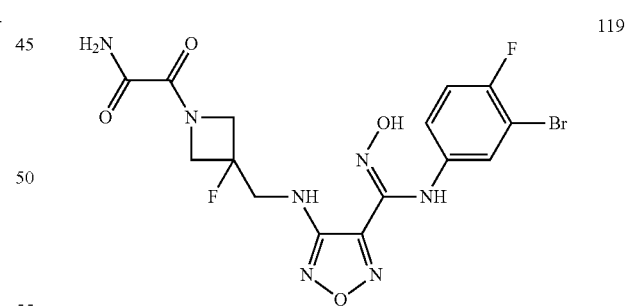
120 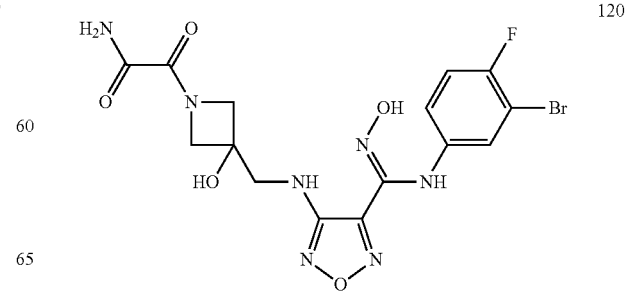

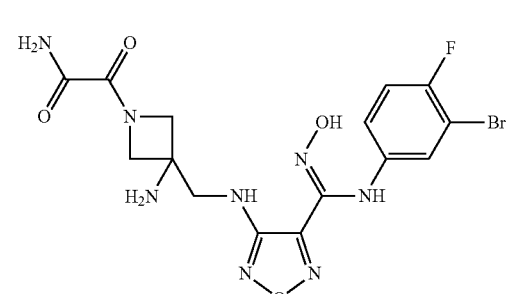
121
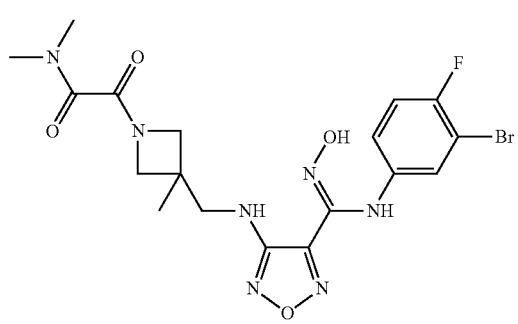
122
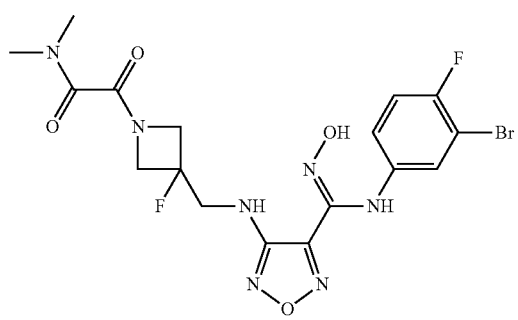
123
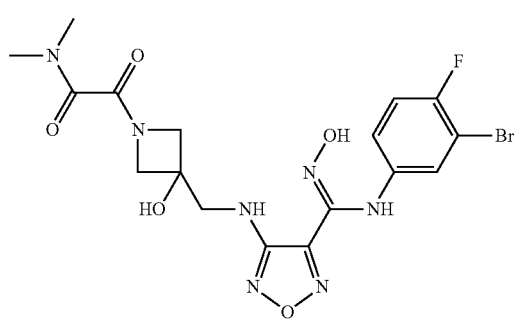
124
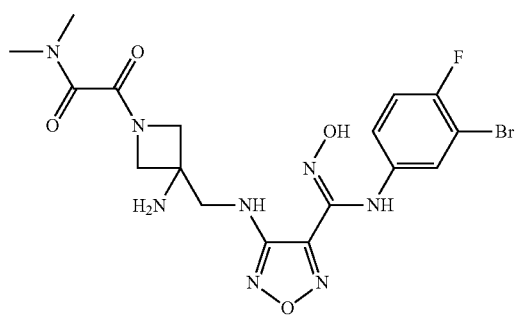
125
126
127
128
129
130

131 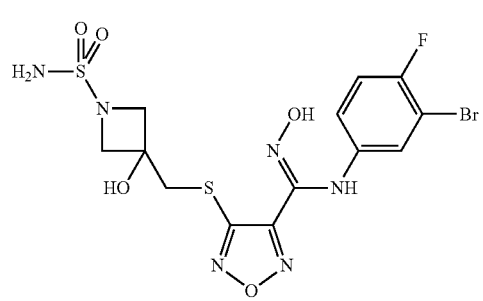
132 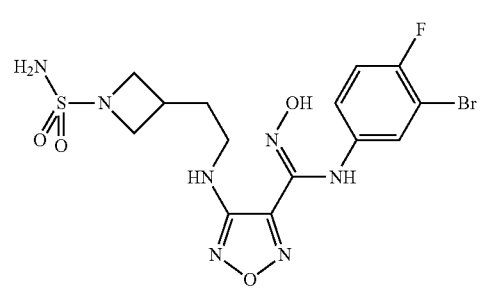
133 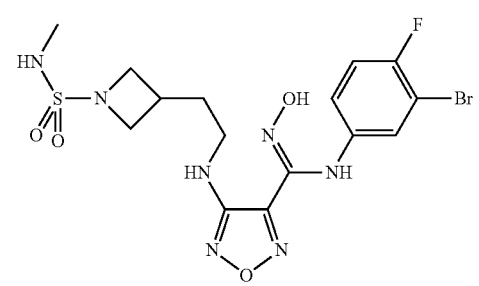
132 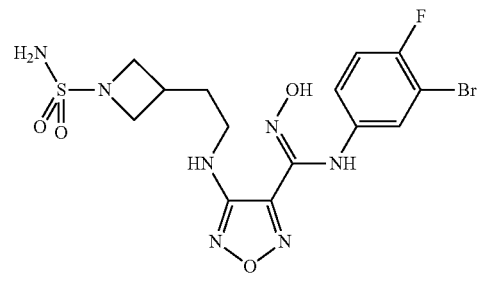
133 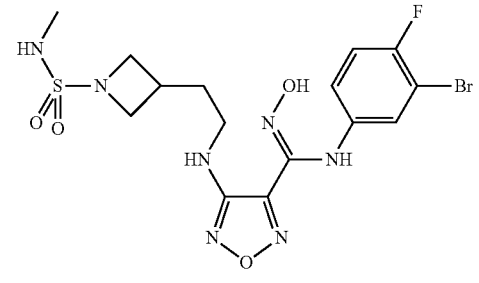
134 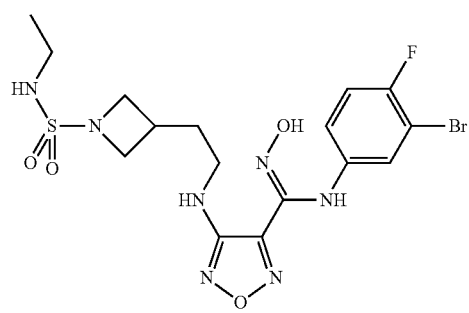
135 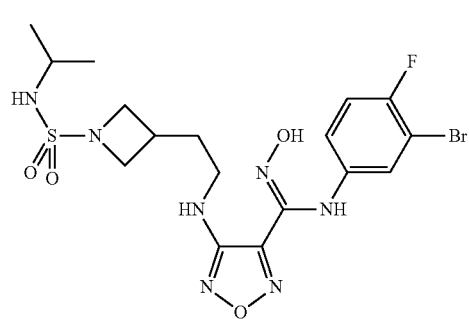
136 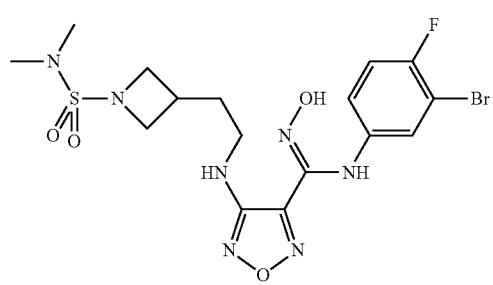
137 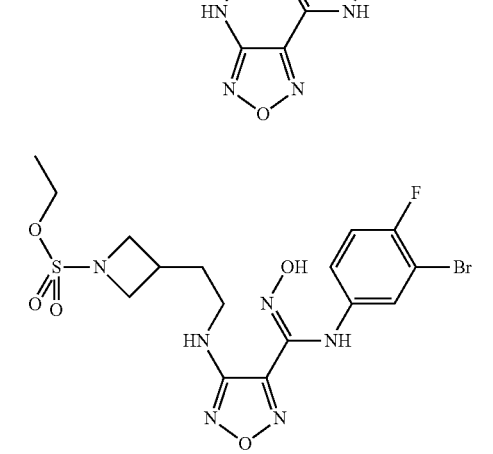
138 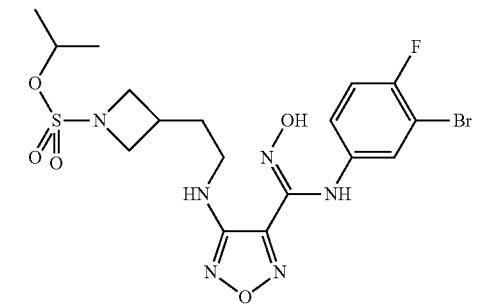

139
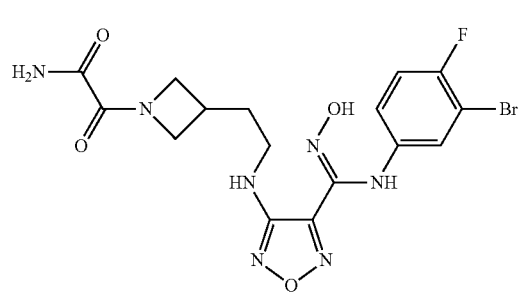
140
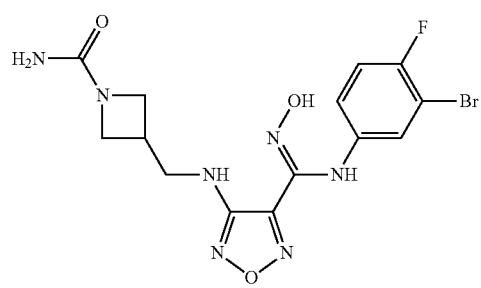
141
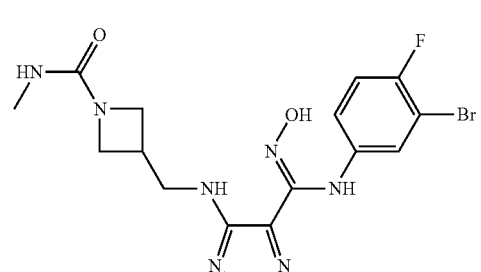
142
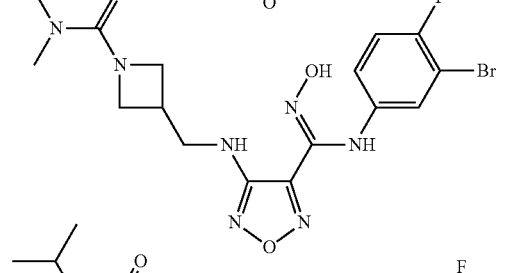
143
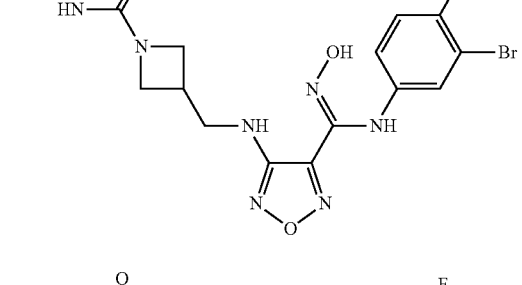
144
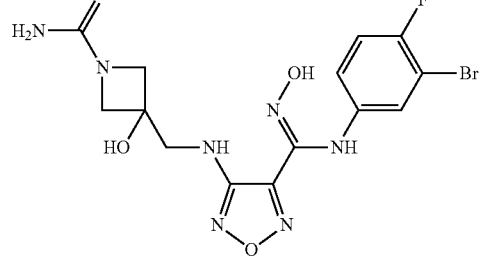
145
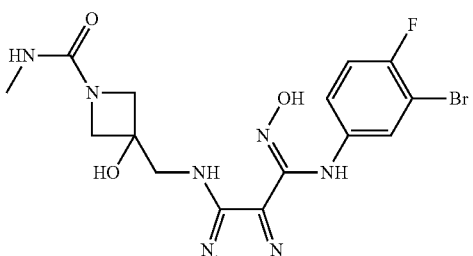
146
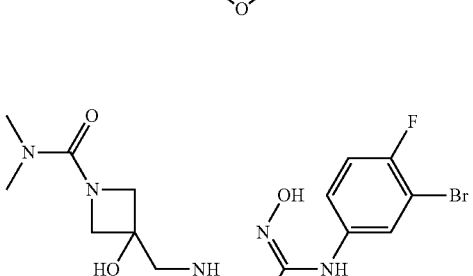
147
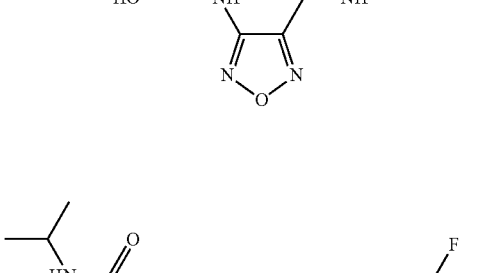
148
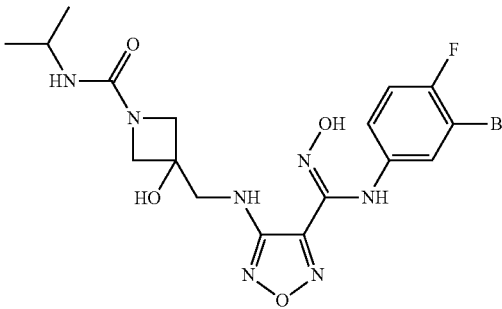
149
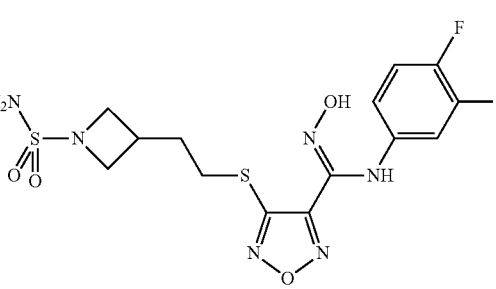

150
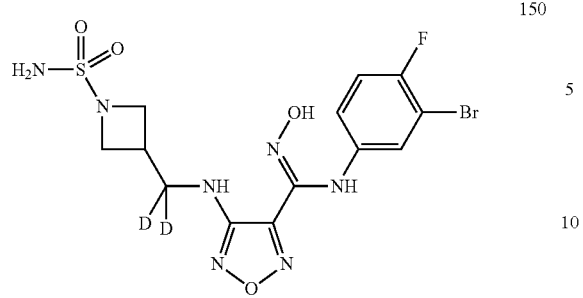
151
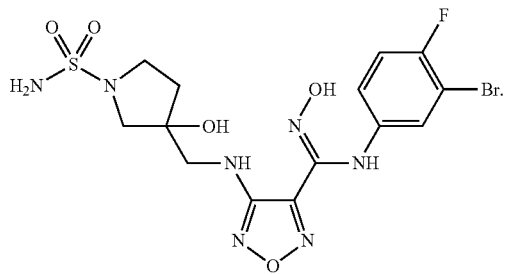
* * * * *